US008652838B2

(12) United States Patent
Shen et al.

(10) Patent No.: US 8,652,838 B2
(45) Date of Patent: Feb. 18, 2014

(54) **PLATENSIMYCIN BIOSYNTHETIC GENE CLUSTER OF *STREPTOMYCES PLATENSIS***

(75) Inventors: Ben Shen, Verona, WI (US); Michael J. Smanski, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 994 days.

(21) Appl. No.: 12/179,406

(22) Filed: Jul. 24, 2008

(65) Prior Publication Data
US 2009/0081673 A1 Mar. 26, 2009

Related U.S. Application Data

(60) Provisional application No. 60/952,564, filed on Jul. 28, 2007.

(51) Int. Cl.
*C12N 15/00* (2006.01)
*C12N 1/20* (2006.01)

(52) U.S. Cl.
USPC ............... 435/320.1; 435/252.3; 435/254.11; 435/257.2

(58) Field of Classification Search
None
See application file for complete search history.

(56) References Cited

PUBLICATIONS

Anderle et al., "Improved mutasynthetic approaches for the production of modified aminocoumarin antibiotics," *Chem. Biol.*, 14:955-967, 2007.
August et al., "Biosynthesis of the ansamycin antibiotic rifamycin: deductions from the molecular analysis of the rif biosynthetic gene cluster of *Amycolatopsis mediterranei* S699," *Chem. Biol.*, 5:69-79, 1998.
Bibb, "Regulation of secondary metabolism in streptomycetes," *Curr. Opinion Microbiol.*, 8:208-215, 2005.
Campbell and Cronan, "Bacterial fatty acid biosynthesis: targets for antibacterial drug discovery," *Annu. Rev. Microbiol.*, 55:305-332, 2001.
Christianson, "Structural biology and chemistry of the terpenoid cyclases," *Chem. Rev.*, 106:3412-3442, 2006.
Cooke et al., "Characterization of NcsB2 as a promiscuous naphthoic acid/coenzyme A ligase integral to the biosynthesis of the enediyne antitumor antibiotic neocarzinostatin," *J. Am. Chem. Soc.*, 129:7728-7729, 2007.
Cundliffe, "Antibiotic production by actinomycetes: the Janus faces of regulation," *J. Ind. Microbiol. Biotechnol.*, 33:500-506, 2006.
Cundliffe, "How antibiotic-producing organisms avoid suicide," *Ann. Rev. Microbiol.*, 43:207-233, 1989.
Cundliffe, In: Self-protection mechanisms in antibiotic producers *in Secondary metabolites: their function and evolution*, Wiley, 199-214, Chichester, 1992.
Dairi, "Studies on biosynthetic genes and enzymes of isoprenoids produced by actinomycetes," *J. Antibioy.* (Tokyo), 58:227-243, 2005.
Davis and Croteau, "Cyclization enzymes in the biosynthesis of monoterpenes, sesquiterpenes, and diterpenes," *Topics Curr. Chem.*, 209:53-95, 2000.
Demain and Vaishnav, "Secondary metabolism in microbes and its control by phosphate and metals," *SIM News*, 54:104-113, 2004.
Du et al., "The biosynthetic gene cluster for the antitumor drug bleomycin from *Streptomyces verticillus* ATCC15003 supporting functional interactions between nonribosomal peptide synthetases and a polyketide synthase," *Chem. Biol.*, 7:623-642, 2000.
Dürr et al., "Biosynthesis of the terpene phenalinolactone in *Streptomyces* sp. Tü6071: analysis of the gene cluster and generation of derivatives," *Chem. Biol.*, 13:365-377, 2006.
El-Mansi et al., "Control of carbon flux through enzymes of central and intermediary metabolism during growth of *Escherichia coli* on acetate," *Curr. Opinion Microbiol.*, 9:173-9, 2006.
Eustaquio et al., "Clorobiocin biosynthesis in *Streptomyces*: identification of the halogenase and generation of structural analogs," *Chem. Biol.*, 10:279-288, 2003.
Eustáquio et al., "Heterologous expression of novobiocin and clorobiocin biosynthetic gene clusters," *Appl. Environ. Microbiol.*, 71:2452-2459, 2005.
Floss and Yu, "Lessons from the rifamycin biosynthetic gene cluster," *Curr. Opinion Chem. Biol.*, 3:592-597, 1999.
Galm et al., "Cloning and analysis of the simocyclinone biosynthetic gene cluster of *Streptomyces* antibioticus Tü 6040," *Arch. Microbiol.*, 178:102-114, 2002.
Gould et al., "3-Amino-4-hydroxybenzoic acid is derived from the tricarboxylic acid cycle rather than the shikimic acid pathway," *J. Am. Chem. Soc.*, 118:9228-9232, 1996.
Hanson, "Steroids: partial synthesis in medicinal chemistry," *Nat. Prod. Rep.*, 23:875-885, 2005.
Hayashi et al., "Identification and functional analysis of bifunctional ent-kaurene synthase from the moss Physcomitrella patens," *FEBS Lett.*, 580:6175-6181, 2006.
Herath et al., "Biosynthetic studies of platecin," *Tetrahedron Letters*, 49:5755-5758, 2008.
Herath et al., "Biosynthetic studies of platensimycin," *J. Am. Chem. Soc.*, 129:15422-15423, 2007.
Herath et al., "Structure and semisynthesis of platensimide A, produced by *Streptomyces* platensis," *Org. Lett.*, 10:1699-1702, 2008.
Hopwood, "Forty years of genetics with *Streptomyces*: from in vivo through in vitro to in silico," *Microbiology*, 145(Pt. 9):2183-202, 1999.
Hornung et al.,"A genomic screening approach to the structure-guided identification of drug candidates from natural sources," *Chem. BioChem.*, 8:757-766, 2007.

(Continued)

*Primary Examiner* — Patricia A Duffy
(74) *Attorney, Agent, or Firm* — Parker Highlander PLLC

(57) ABSTRACT

The present invention relates to the cloning and sequence of a biosynthetic gene cluster from *Streptomyces platensis* that produces platensimycin and platencin. Also provided are engineered micro-organisms for the production of these compounds, and analogs thereto, as well as methods of screening for compounds with anti-bacterial activity.

11 Claims, 24 Drawing Sheets

(56) References Cited

PUBLICATIONS

Hu and Floss, "Further studies on the biosynthesis of the manumycin-type antibiotic, asukamycin, and the chemical synthesis of protoasukamycin," *J. Am. Chem. Soc.*, 126:3837-3844, 2004.

Jayasuriya et al., "Isolation and structure of platencin: a FabH and FabF dual inhibitor with potent broad-spectrum antibiotic activity," *Agnew Chem. Int. Ed. Engl.*, 46:4684-4688, 2007.

Kawasaki et al., "A relationship between the mevalonate pathway and isoprenoid production in actinomycetes," *J. Antibiot.*, 56:957-966, 2003.

Kuzuyama and Seto, "Diversity of the biosynthesis of the isoprene units," *Nat. Prod. Rep.*, 20:171-183, 2003.

Kwon et al., "C—O bond formation by polyketide synthases," *Science*, 297:1327-1330, 2002.

Li and Heide, "New aminocoumarin antibiotics from genetically engineered *Streptomyces* strains," *Curr. Med Chem.*, 12:419-427, 2005.

Manallack et al., "Platensimycin: a promising antimicrobial targeting fatty acid synthesis," *Curr. Med. Chem.*, 15:705-710, 2008.

Mohan et al., "Biosynthesis of cyclic diterpene hydrocarbons in rice cell suspensions: conversion of 9,10-syn-labda-8(17),13-dienyl diphosphate to 9beta-pimara-7,15-diene and stemar-13-ene," *Arch. Biochem. Biophys.*, 330:33-47, 1996.

Nicolaou et al., "Design, synthesis, and biological evaluation of platensimycin analogues with varying degress of molecular complexity," *Journal of the American Chemical Society*, 130:13110-13119, 2008.

Nicolaou et al., "Total synthesis of platencin," *Agnew Chem. Int. Ed. Engl.*, 47:1780-1783, 2008.

Petricek et al., "Occurrence of two 5-aminolevulinate biosynthetic pathways in *Streptomyces nodosus* subsp. asukaensis is linked with the production of asukamycin," *J. Bacteriol.*, 188:5113-23, 2006.

Pojer et al., "Molecular cloning and sequence analysis of the clorobiocin biosynthetic gene cluster: new insights into the biosynthesis of aminocoumarin antibiotics," *Microbiology*, 148:3901-3911, 2002.

Prisic et al., "Probing the role of the DXDD motif in Class II diterpene cyclases," *Chem. BioChem.*, 8:869-874, 2007.

Prisic et al., "Rice contains two disparate ent-copalyl diphosphate synthases with distinct metabolic functions," *Plant Physiol.*, 136:4228-4236, 2004.

Roy et al., "16-Aza-*ent*-beyerane and 16-Aza-*ent*-trachylobane: potent mechanism-based inhibitors of recombinant *ent*-Kaurene synthase from *Arabidopsis thaaliana*," *J. Am. Chem. Soc.*, 129:12453-12460, 2007.

Singh et al., "Isolation, structure, and absolute stereochemistry of platensimycin, a broad spectrum antibiotic discovered using an antisense differential sensitivity strategy," *J. Am. Chem. Soc.*, 128:11916-11920, 2006.

Steffensky et al., "Cloning, overexpression, and purification of novobiocic acid synthetase from *Streptomyces* spheroides NCIMB 11891," *J. Biol. Chem.*, 275:21754-21760, 2000.

Steffensky et al., "Identification of the novobiocin biosynthetic gene cluster of *Streptomyces* spheroides NCIB 11891," *Antimicrob. Agents Chemother.*, 44:1214-1222, 2000.

Suzuki et al., "Novel benzene ring biosynthesis from C(3) and C(4) primary metabolites by two enzymes," *J. Biol. Chem.*, 281:36944-36951, 2006.

Takano, "Gamma-butyrolactones: *Streptomyces* signalling molecules regulating antibiotic production and differentiation," *Curr. Opinion Microbiol.*, 9:287-94, 2006.

Tiefenbacher and Mulzer, "Synthesis of platensimycin," *Angew. Chem. Int. Ed.*, 47:2548-2555, 2008.

Toyomasu et al., "Fusicoccins are biosynthesized by an unusual chimera diterpene synthase in fungi," *Proc. Natl. Acad. Sci. USA*, 104:3084-3088, 2007.

Tudzynski, "Gibberellin biosynthesis in fungi: genes, enzymes, evolution, and impact on biotechnology," *Appl. Microbiol. Biotechnol.*, 66:597-611, 2005.

Walsh et al., "Tailoring enzymes that modify nonribosomal peptides during and after chain elongation on NRPS assembly lines," *Curr. Op. Chem. Biol.*, 5:525-534, 2001.

Wang et al., "Discovery of platencin, a dual FabF and FabH inhibitor with in vivo antibiotic properties," *Proc. Natl. Acad. Sci. USA*, 104:7612-7616, 2007.

Wang et al., "High-level expression of cecropin CMIV in *E. coli* from a fusion construct containing the human tumor necrosis factor," *Biochem. Mol. Biol. Int.*, 41:1051-6, 1997.

Wang et al., "Identification of the coumermycin A(1) biosynthetic gene cluster of *Streptomyces* rishiriensis DSM 40489," *Antimicrob. Agents Chemother.*, 44:3040-3048, 2000.

Wang et al., "Platensimycin is a selective FabF inhibitor with potent antibiotic properties," *Nature*, 441:358-360, 2006.

Wilderman et al., "Identification of syn-pimara-7,15-diene synthase reveals functional clustering of terpene synthases involved in rice phytoalexin/allelochemical biosynthesis," *Plant. Physiol.*, 135:2098-2105, 2004.

Xu et al., "Following evolution's lead to a single residue switch for diterpene synthase product outcome," *Proc. Natl. Acad. Sci. USA*, 104:7397-7401, 2007.

Xu et al., "Functional characterization of the rice kaurene synthase-like gene family," *Phytochemistry*, 68:312-326, 2007.

Xu et al., "Functional identification of rice syn-copalyl diphosphate synthase and its role in initiating biosynthesis of diterpenoid phytoalexin/allelopathic natural products," *Plant J.*, 39:309-318, 2004.

Xu et al., "New aminocoumarin antibiotics formed by a combined mutational and chemoenzymatic approach utilizing the carbamoyltransferase NovN," *Chem. Biol.*, 11:655-662, 2004.

D 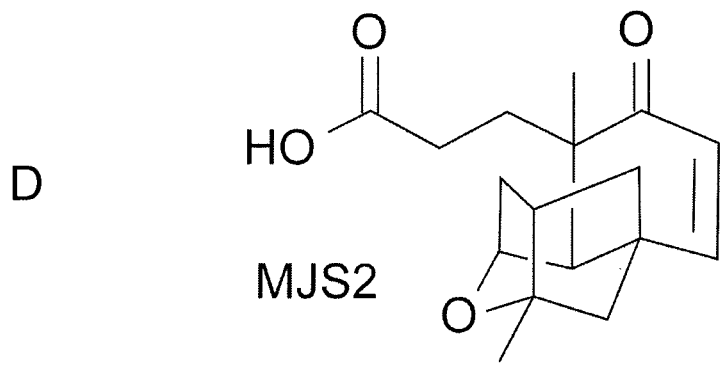
MJS2
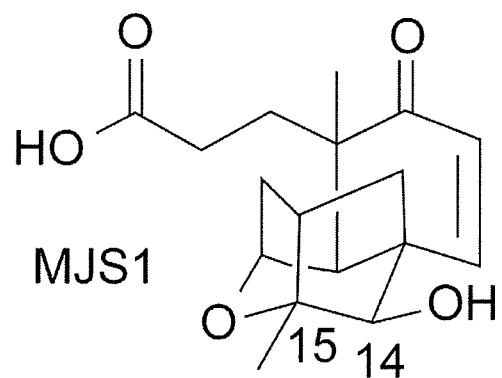
MJS1
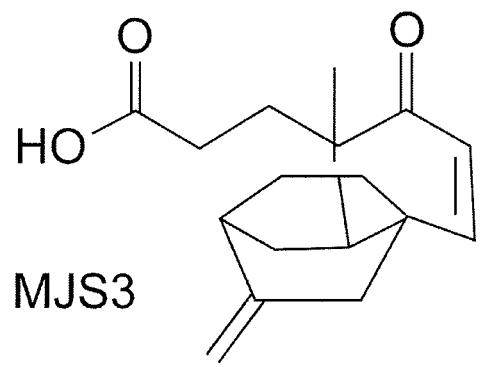
MJS3
FIG. 4

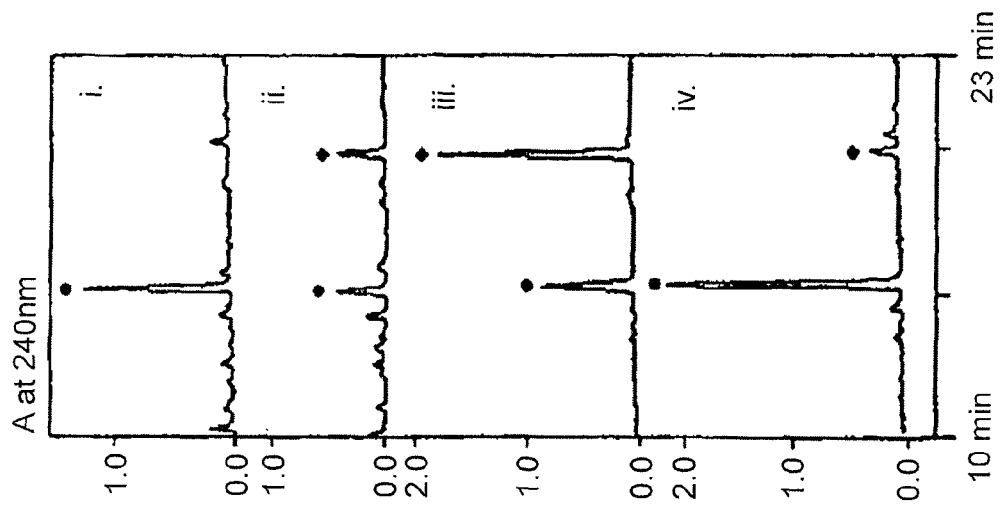
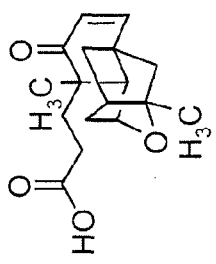
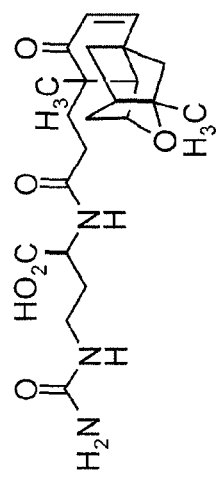
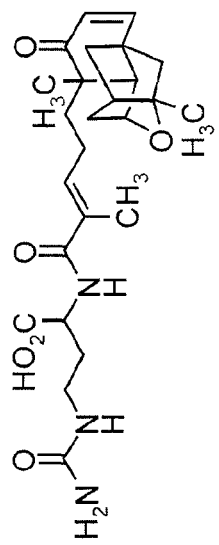
FIG. 6

C
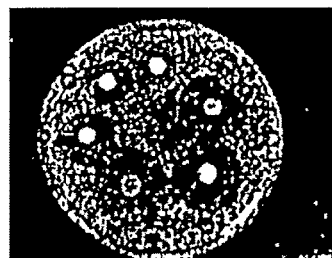
PTM
S. avermitilis
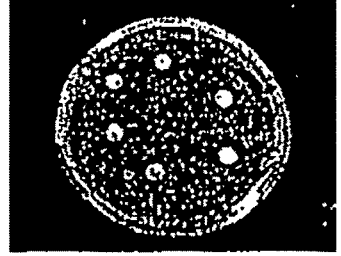
PTM
S. albus J1074
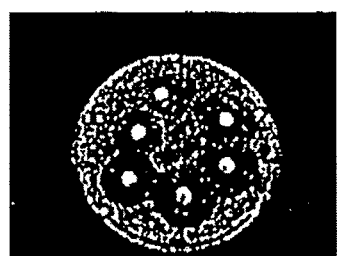
PTN
S. avermitilis
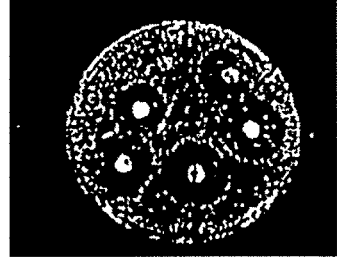
PTN
S. albus J1074
FIG. 6

SEQUENCE LISTING

<160> NUMBER OF SEQ ID NOS: 1

<210> SEQ ID NO 1
<211> LENGTH: 39194
<212> TYPE: DNA
<213> ORGANISM: Streptomyces platensis
<220> FEATURE:
<221> NAME/KEY: misc_feature
<222> LOCATION: (26962)..(26962)
<223> OTHER INFORMATION: n is a, c, g, or t
<220> FEATURE:
<221> NAME/KEY: misc_feature
<222> LOCATION: (26966)..(26966)
<223> OTHER INFORMATION: n is a, c, g, or t
<220> FEATURE:
<221> NAME/KEY: misc_feature
<222> LOCATION: (26969)..(26969)
<223> OTHER INFORMATION: n is a, c, g, or t
<220> FEATURE:
<221> NAME/KEY: misc_feature
<222> LOCATION: (26984)..(26984)
<223> OTHER INFORMATION: n is a, c, g, or t
<220> FEATURE:
<221> NAME/KEY: misc_feature
<222> LOCATION: (27111)..(27111)
<223> OTHER INFORMATION: n is a, c, g, or t
<220> FEATURE:
<221> NAME/KEY: misc_feature
<222> LOCATION: (30482)..(30482)
<223> OTHER INFORMATION: n is a, c, g, or t
<220> FEATURE:
<221> NAME/KEY: misc_feature
<222> LOCATION: (30529)..(30529)
<223> OTHER INFORMATION: n is a, c, g, or t
<220> FEATURE:
<221> NAME/KEY: misc_feature
<222> LOCATION: (30551)..(30551)
<223> OTHER INFORMATION: n is a, c, g, or t
<220> FEATURE:
<221> NAME/KEY: misc_feature
<222> LOCATION: (32497)..(32497)
<223> OTHER INFORMATION: n is a, c, g, or t
<220> FEATURE:
<221> NAME/KEY: misc_feature
<222> LOCATION: (32504)..(32504)
<223> OTHER INFORMATION: n is a, c, g, or t
<220> FEATURE:
<221> NAME/KEY: misc_feature
<222> LOCATION: (32540)..(32540)
<223> OTHER INFORMATION: n is a, c, g, or t
<220> FEATURE:
<221> NAME/KEY: misc_feature
<222> LOCATION: (32550)..(32550)
<223> OTHER INFORMATION: n is a, c, g, or t
<220> FEATURE:
<221> NAME/KEY: misc_feature
<222> LOCATION: (34089)..(34089)
<223> OTHER INFORMATION: n is a, c, g, or t
<220> FEATURE:
<221> NAME/KEY: misc_feature
<222> LOCATION: (36487)..(36488)
<223> OTHER INFORMATION: n is a, c, g, or t
<220> FEATURE:
<221> NAME/KEY: misc_feature
<222> LOCATION: (36493)..(36493)
<223> OTHER INFORMATION: n is a, c, g, or t
<220> FEATURE:
<221> NAME/KEY: misc_feature
<222> LOCATION: (37950)..(37950)
<223> OTHER INFORMATION: n is a, c, g, or t
<220> FEATURE:
<221> NAME/KEY: misc_feature
<222> LOCATION: (37957)..(37957)
<223> OTHER INFORMATION: n is a, c, g, or t
<220> FEATURE:
<221> NAME/KEY: misc_feature
<222> LOCATION: (37963)..(37963)

-continued

```
<223> OTHER INFORMATION: n is a, c, g, or t
<220> FEATURE:
<221> NAME/KEY: misc_feature
<222> LOCATION: (37970)..(37970)
<223> OTHER INFORMATION: n is a, c, g, or t
<220> FEATURE:
<221> NAME/KEY: misc_feature
<222> LOCATION: (37983)..(37983)
<223> OTHER INFORMATION: n is a, c, g, or t
<220> FEATURE:
<221> NAME/KEY: misc_feature
<222> LOCATION: (38014)..(38014)
<223> OTHER INFORMATION: n is a, c, g, or t
<220> FEATURE:
<221> NAME/KEY: misc_feature
<222> LOCATION: (38027)..(38027)
<223> OTHER INFORMATION: n is a, c, g, or t
<220> FEATURE:
<221> NAME/KEY: misc_feature
<222> LOCATION: (38035)..(38035)
<223> OTHER INFORMATION: n is a, c, g, or t
<220> FEATURE:
<221> NAME/KEY: misc_feature
<222> LOCATION: (38046)..(38046)
<223> OTHER INFORMATION: n is a, c, g, or t
<220> FEATURE:
<221> NAME/KEY: misc_feature
<222> LOCATION: (38051)..(38051)
<223> OTHER INFORMATION: n is a, c, g, or t
<220> FEATURE:
<221> NAME/KEY: misc_feature
<222> LOCATION: (38575)..(38581)
<223> OTHER INFORMATION: n is a, c, g, or t
<220> FEATURE:
<221> NAME/KEY: misc_feature
<222> LOCATION: (38585)..(38585)
<223> OTHER INFORMATION: n is a, c, g, or t
<220> FEATURE:
<221> NAME/KEY: misc_feature
<222> LOCATION: (38600)..(38600)
<223> OTHER INFORMATION: n is a, c, g, or t
<220> FEATURE:
<221> NAME/KEY: misc_feature
<222> LOCATION: (38614)..(38614)
<223> OTHER INFORMATION: n is a, c, g, or t
<220> FEATURE:
<221> NAME/KEY: misc_feature
<222> LOCATION: (38621)..(38621)
<223> OTHER INFORMATION: n is a, c, g, or t
<220> FEATURE:
<221> NAME/KEY: misc_feature
<222> LOCATION: (38631)..(38631)
<223> OTHER INFORMATION: n is a, c, g, or t
<220> FEATURE:
<221> NAME/KEY: misc_feature
<222> LOCATION: (38633)..(38633)
<223> OTHER INFORMATION: n is a, c, g, or t
<220> FEATURE:
<221> NAME/KEY: misc_feature
<222> LOCATION: (38645)..(38645)
<223> OTHER INFORMATION: n is a, c, g, or t
<220> FEATURE:
<221> NAME/KEY: misc_feature
<222> LOCATION: (38721)..(38721)
<223> OTHER INFORMATION: n is a, c, g, or t
<220> FEATURE:
<221> NAME/KEY: misc_feature
<222> LOCATION: (38748)..(38748)
<223> OTHER INFORMATION: n is a, c, g, or t
<220> FEATURE:
<221> NAME/KEY: misc_feature
<222> LOCATION: (38831)..(38831)
<223> OTHER INFORMATION: n is a, c, g, or t
<220> FEATURE:
<221> NAME/KEY: misc_feature
<222> LOCATION: (38864)..(38864)
<223> OTHER INFORMATION: n is a, c, g, or t
<220> FEATURE:
<221> NAME/KEY: misc_feature
<222> LOCATION: (38869)..(38869)
```

```
<223> OTHER INFORMATION: n is a, c, g, or t
<220> FEATURE:
<221> NAME/KEY: misc_feature
<222> LOCATION: (38878)..(38878)
<223> OTHER INFORMATION: n is a, c, g, or t
<220> FEATURE:
<221> NAME/KEY: misc_feature
<222> LOCATION: (38896)..(38896)
<223> OTHER INFORMATION: n is a, c, g, or t
<220> FEATURE:
<221> NAME/KEY: misc_feature
<222> LOCATION: (38916)..(38916)
<223> OTHER INFORMATION: n is a, c, g, or t
<220> FEATURE:
<221> NAME/KEY: misc_feature
<222> LOCATION: (38924)..(38924)
<223> OTHER INFORMATION: n is a, c, g, or t
<220> FEATURE:
<221> NAME/KEY: misc_feature
<222> LOCATION: (38975)..(38975)
<223> OTHER INFORMATION: n is a, c, g, or t
<220> FEATURE:
<221> NAME/KEY: misc_feature
<222> LOCATION: (39010)..(39010)
<223> OTHER INFORMATION: n is a, c, g, or t
<220> FEATURE:
<221> NAME/KEY: misc_feature
<222> LOCATION: (39014)..(39014)
<223> OTHER INFORMATION: n is a, c, g, or t
<220> FEATURE:
<221> NAME/KEY: misc_feature
<222> LOCATION: (39016)..(39016)
<223> OTHER INFORMATION: n is a, c, g, or t
<220> FEATURE:
<221> NAME/KEY: misc_feature
<222> LOCATION: (39025)..(39025)
<223> OTHER INFORMATION: n is a, c, g, or t
<220> FEATURE:
<221> NAME/KEY: misc_feature
<222> LOCATION: (39061)..(39061)
<223> OTHER INFORMATION: n is a, c, g, or t
<220> FEATURE:
<221> NAME/KEY: misc_feature
<222> LOCATION: (39088)..(39089)
<223> OTHER INFORMATION: n is a, c, g, or t
<220> FEATURE:
<221> NAME/KEY: misc_feature
<222> LOCATION: (39095)..(39095)
<223> OTHER INFORMATION: n is a, c, g, or t
<220> FEATURE:
<221> NAME/KEY: misc_feature
<222> LOCATION: (39114)..(39114)
<223> OTHER INFORMATION: n is a, c, g, or t
<220> FEATURE:
<221> NAME/KEY: misc_feature
<222> LOCATION: (39143)..(39143)
<223> OTHER INFORMATION: n is a, c, g, or t
<220> FEATURE:
<221> NAME/KEY: misc_feature
<222> LOCATION: (39166)..(39166)
<223> OTHER INFORMATION: n is a, c, g, or t

<400> SEQUENCE: 1
agggttattg tctcatgagc ggatacatat ttgaatgtat ttagaaaaat aaacaaatag      60
gggttccgcg cacatttccc cgaaaagtgc cacctgacgt ctaagaaacc attattatca    120
tgacattaac ctataaaaat aggcgtatca cgaggcccct tcgtcttcaa gaattcgcgg    180
ccgcaattaa ccctcactaa agggatccgt cccatcagct cgtgctgcgg ctcgtcgggg    240
gagccggggc ggccgcgcca ggtgatcagc agcaggacgg ggagccgcag ggtgtggcac    300
agcgaggtga gcgggttgac cgcgttgccc aggccggagt tctggaggat gacgacgggc    360
agccgcccgg ccagccgggc gccggcggcg atgccacgg  cctcgccctc gttggcagtg    420
gtgaggtagt ccgccgggtg ctcctgctgg aggcagctga tcaccggtcc gaggaacgag    480
```

```
cagggcaccc cgctgaaggg gcccaggccc gccgcgcgga acgtgcggac gatgacggcc      540
ggatcgagcg tgcggggcgc ggcgggcgcg gcggtcacgg ggcgtcccct ccggtcagca      600
cggggaccgg gcgtgcgtgc tccgccggct cgccgtcgcg cccggggggcg ggggccgggg      660
gtgcctccgg cgtgccgccg cggacgaacc gcttctcgtt ctccgtgaac tcgtccatgc      720
cctggaggtc gaagacggtc ttcagcggag cgatgtggtc ctcgatcgcg gtggtacggc      780
cgtccttgag gatcgtctcg aaggtctggc tgacggcctg gatcccggcc cgcagcccgt      840
ggttggcgta gacgaccatc ttggcgccgg ccgcgcccag ttcaccggcc gagatggtgt      900
ggtacgtggt gggcaccacg accaccggct gggggaggtg ccaccgctgg aggaagtcca      960
gcaccggctg cggggagccg gatttggcgt ggatgaggac cgcgtcggca ccggccgcgg     1020
cgtaggcctc gccccggcgg agcgcctcgt ccaggtccca gccggcgatc agggcctcga     1080
tccgggcgat caccatgaag tcggggtcgc gctgggcttc cttggcggct tcgatccggc     1140
cgcagaactc cggtacggac gccagctcct gacggcccgg tatgaagctg ttgaccttgg     1200
ggaagcgctt gtcctcgatg gtgacggcgg cgataccggc ggcttcgtag cgtcgaacca     1260
tgtgcatgac attgttggcg ttgccgtagc cggtgtcgca gtcggcgacc acgggcacgt     1320
tgaccgcgga cgccatcgac ccggcaacgc ccaggagttc ggtcatggtc aggatgtccg     1380
cgtcgggcag gccctgggac gccgagatct ccagaccgct cgaccagatg ccgtcgaacc     1440
ccgcgcgttc cgccaggcgg gcgcccagcg ggttgtgggc gccggcgatg cgcacggtgc     1500
cggggggcgtc gaaaagggcg cgcagttgtg ccgcgccctg gcgcggggcg ggccgggccg     1560
agggctcgcg gtgtgtgctg tggaggtggt ccacggaatt cccctctgct cagctctgtg     1620
cgtgtgccgg aagtgacggc gaagtgtcct gctgcttttc ggattccggg cgccagcccg     1680
gccggccgaa gagataccc atacggtgcc gccaggtgtc ggcgccgcgt acctcccggg     1740
ccatggtggc gaattcatgc acatggatct tccagatgct gtaggtgttg atctgcttcg     1800
tcagcccgta ggtggggcgt cggccctccg gctggaaggt gccgaacatc cggtcccaga     1860
tgatgaggat gctgccgaag ttcttgtcga gatactccgg ttccgtgccg tggtggaccc     1920
ggtggtgtga cgccgtcaca aagatgaatt ccagcgggcg cggcagcttt ccgacctttt     1980
cggtgtgggc gaacagaccg tagatcaggt ggaaggagtg catggtgaag accagtaccg     2040
gcggcacacc cagcagtggc agcggaagcc agaccagctt ttcgaaccac tgcgcccact     2100
tgcgccgcag cgcggtcgag gtattgaagt actcgctgga gtggtggact tggtgaccgg     2160
cccagatgat gcggatcata tgggccgaac ggtgatacca gtacagcagg aattcgacgc     2220
cgaagaagag caccacccag gtccaccagg cgtcggccgg cagatggaac ggggcgaggt     2280
acgtatagac caccgcgtag agcccgagcg cggcggcgcg cagcagcgtg acaccacca     2340
gcgcgcccag cccggtcagc acgctggcgc gggtgtcgcg ggcgttgaag cccttgacgt     2400
ccttgtcgtc gccgaagcgc agggccagca tttcgacggc gaccagcagg acgacgcgg     2460
ggagggcgaa gacgatcgga tctctgagac ggtcgaggat ctgtgacagc acgtatttct     2520
ccaggaaccc ttattcgctg acggtggcga gtgccttcgc cttggtggcg tacatgtcga     2580
cgtactcctg accggagagc accgcgatct cgcgcatgac ctggtcggcc acctgacggc     2640
gcaggcgcgc ctcgccggag cgccctggt gctccgagaa atccatgggg gcgccgaagc     2700
gcagccggaa ccggtgcggg cggaacatca gcgtcccggg cggctggacc ttttcggtgc     2760
cggtcagccc gcacggaatg accggtgccc cggtgagcag ggccagataa ccgacccgg     2820
tgcggccgcg gtagaggcgg ccgtcatggg tgcgggtgcc ttccgggatg aatgccgaag     2880
```

```
atctttccct cgcccagtac ccgctcggcg agctggagcg cggccacgcc gccgtgaccg    2940
ccgtcgcgct cgaccggaac cagcccgatg gcccggaaga agcaggcggc gagccggcct    3000
ttgacgcctt tcccggtcag ccgctcggcc ttcccgatga agacgacggg gcgcttgacg    3060
gccagcgcga tgaagacatg gtcggagaac gacaggtgat tcgccgcgat gatgcaggga    3120
cctgtggtgg gaatgttttt ggtgccgtcg atatgcggcc ggaagacgat tcgcatcagc    3180
gccgcaagga cgactctgag cgctctgaaa aacactgtcc gcctccaatc tgcaaaggaa    3240
cgtgcgggtg tgccgacgcc ggtacgcgag tgggtaccgg gaacggttct gggggaggga    3300
ggggcggcgc ctcagtgcac gatcgtgcgg ccgccttcga ggacgagggt ggcgccggtg    3360
aggtagcgca tcccgtcgtc ggccagcgcc accacggccc ggccgatgtc ctgctcggcg    3420
tccccgagcc ggccgagcgg aatctcggac agcacctcgg tgtgcttctc ggggtgcgcc    3480
tcgaagtacg cggccgcgcc ggggctgagc gagaccgggc agatcgcgtt gacccggatg    3540
ccgtacgggc cccactcccg gcggcgacc cgggtgagcc cgcggatcgc ctccttcgcc    3600
atcgcgtagg aggcgaagcc ctcctggccg atgagcgccg cggaggaggc gaggttgacg    3660
atgctgccgc cgcgccgcca caggtacgga agggccgcac gcatcgcgtg aaggtgccc    3720 aacgggccgc tgcggtagga gagttcgagg tcctcgtagc tggtttccgc cagcggccgc    3780
tggacgaccg actgggcgtt gttgacgagg atgtccagcc cgccgaaggt ccgggcggtc    3840
tcctcgacca tgcggtcgac gtcgtcgcgc tgccccacgt caccgacgac ggcgtgcccg    3900
gcggcccctc gctcctcgat ctcggtgacc acggcccgca gcgttttctc ggtgcgtccc    3960
gtgacgacga cgtcggcgcc ctcggcggcc agcgccaggc gatgccccg gccgatgccc    4020 tgaccgccgc cggtgaccag agccgtcgtc ccggccagac gctggtggga agtcatggag    4080
tggtgtgccc tttcgcgtgc ggtacggggg cgtcgtcgcc ccagaaggtc tgccaggtgg    4140
ggaaggagtg cgggagggcg gggcgtcccg cgggcggcca gtccgcaaag ccgacggcct    4200
gcgggcggtc cgtcacatcg gcggcgtacc agtgccgttc ccggcgccgg gtgaagagcc    4260
attcgccctc cacgcacgcg tagtcgtcga agtagcagat cgccatgacg atccagcggt    4320
cgtccacctc gtgctcggcg cggcagtaga ccgtcccggt cgcccgctgc gccccctgcc    4380
actcgatgcg gtggccggtg atgtggtgca ccgaccggtg gaaggtgcgc agcatcggtg    4440
cgatgtggcg gcgcagcacc tcgccggccg ggccggcccg ccccatgtcc acgtcggggt    4500
ggaagcaccc cacccacgcg tccaggtcgc gtgcgtcgac ggcgagcgca tagcggaacg    4560
cgagctgctg gatcgccagg tgcgcttcca cccgcgccag acgccgctcg atctccgggc    4620
cggtcactgc gtccaccctc ccaccaccac cctcaaagga ctatattagt taactaatat    4680
agcgggttag gtacctgaag gtaagggaga gccatgcccg acagagagtt cttcgatccg    4740
gaggcagaga ccctgcccag ggagcggctg ctggcccggc aggaagcgcg catcctcgaa    4800
ctcgtcccgc acgtcttcga acactccgcg ttctaccggg agttgtggag cgcacacggt    4860
gtccacccgc gcgacgtccg ctcgttggag gacttccgcc ggcgcatccc gacgatcacc    4920
aaggacatgt tccgcgcgta ccgggcccgg accggcgacc ccttcggcgg actgctgtgc    4980
acggacgtct cggagctgac ctcggtctcc tccagctccg gcaccaccgg ccggccgacg    5040
ttcttcgccg aacagtggga ccggtgcccg ccgctgcccg ccgcgatgct gcgcgacctg    5100
tgggggctgg gactgcggcc cggcgaccgg gtgctcagcc agcccggcac catacgcaat    5160
ctgctcgact acgtcttcca cgcgctgggc accaccgtcg tctgcgtgga gtccggcccc    5220
gggcagatgg ccggggtggt cgaggcggcc cggcgctacc ggcccgcctt cttgcagctc    5280
```

```
acctacgccc aggtcgtcga gctgacccgg ctcgcggacc ggctcgatct gcgcgaggcg    5340
ttctcctccc tgaaggccgc cgccttcgcc ggggcgccca tgagccgccg gatgcgggag    5400
atggtccaac aggactgggg tatcgagctg ttcgagtaca ccagcgccgc cgacaccggg    5460
atggcgtggg agtgcgaccg gcacgacggc ttccatctgt gggaggacac ggtcttcgcc    5520
gagtgcctcg atccgcggag cctcgccgag gtccccgagg gggagctcgg cgagctggtc    5580
gccaccgacc tcgacaaccc cacgcgcgcc ctgatccgct accgcagcga cgacctcgtc    5640
cggctgagcc ggaagccgtg cggctgcggg cgcacccacg gccggatgtg gctgcggggc    5700
cggtgcggcg acgagaccct ggtcggcggg gtgcccgtca tgctgcgcga catcggactc    5760
gcggtcgagg accagccgga gtgcgccggc ggggtgttcc agatggtccg gccgcagcgc    5820
gaactgagcg cgctcacggt ccgggtcggc tatgagaccg ccggggccgg cacgccgccc    5880
ccggatctgg cggagcggct gcgcaaggcg attcatgcgc gcaccggggt gactccggtg    5940
ctggaactgc gtacggagca cgagctgctg gcgggttcca gcggcgtggg caagctgaca    6000
cgagtggtga ggtcatgatg gtacgaacgg aatccctggc acgcgccaag tccctggccc    6060
ggcccgaaat cgcctacgtg gccaggttca ccgccgccga cggtgccggc gaggagttca    6120
aggtcacctg gtccgacatc gcccgggaca ccatgtggct ccagaagcgc ttcacggcat    6180
gggggatggg gcggggcaag caggtcctgc tctcgacctc gggccacgag ggcgcatggt    6240
ttctgccggt gatcaacgcg ctgaaggcga tcggctgcac ctatgcgata ccgaggcga    6300
tggcctggga ctggcgccgg tcgctggtct ccacgaggga gctggagctc tacgcgatgc    6360
tggggctgtc cggcgagatc gtggcggaac agaccaagtg ccgcaaggcg gccgacctct    6420
tcggcgacgt tccggtgctc ctggcgcggc ccgccgccgt ccggcagctg gcggccggcg    6480
gggtcggcgc gggcgtgctg acgccgctgg ggcccgcgct ggccgtgcag tgtcccgagt    6540
cccccggggc ccatatcgat ctcggtgcgg tggtgggtgg cggagcgccg gggccggatc    6600
cacctcgccg cgcgctccgg cggcggggc cgcggcgcgg cggagaccgg gctgggcatc    6660
gagggcgtgg tgctgggcgg acggtgcggc tgcggcagcg acgaccccgg ggtgctgctg    6720
agctgaccgg ggctgccgcg ccccggtacc ggcggggcgc ggcagcggcg gtcaggggt    6780
gccgtccggc acgaagtacg gcaggctgat ctcgtcgctg acgggccgga agctgacccg    6840
gaccggcatc ccgatcacga cctgctcgac gggcacgtcg accacatggc tgagcagggt    6900
gccgccgtcc tccagatcga cggcggccag ggcgaagggc acctcgaagc ccggcccggg    6960
tgcacggtgc accacggtca ccgcgtacac cgtgccgcgg cccgtgctgg gctcccaggt    7020
ccagtcctgc gaccagcaca cggggcagac cggttcggga gcgaagaagc ggtggccgca    7080
ggggagcag gccggaacga ccagccgcc gtgccgcgcg gacgcccaga agggccgggt    7140
cagctccgtc ggtacgggaa cggggcgggc catcaccggc tccttcccag caggcacatc    7200
tcgtagtgct gcgcgccgga gcccgcattg gcgaccagcg ccagctcggc gccggggatc    7260
tggtgtacgg cgctgccgcg cagctgccgt acggcctcca cgacccgcag ggtcatctgc    7320
tgggtgccgt tccacgcgta ggacagacag ccgccgtcag ggttgaccgg gtgcttgccg    7380
tccggggcga tcgcgccgtc ggccgcgagc gggccgccct cgccctccgc gcacagcccc    7440
agcacctcca gctgccggat cacctcgaag gagttcgggt cgtagaagga gaaaacgtcg    7500
atgtcgtggg cggtgagccc ggcccgtgcg tagcagcggg cggcggaagc ggcgccaatc    7560
cgcccgaact cacgtcccag cgccggattc acatacgccg catggtggta ctccatcgat    7620
ccggcgagca ccgcgaccgg cagccgcggc agatcgcggg cccgttcggc cgtggtgacc    7680
```

```
acgaaggcgg cgccgccctc accgacgatg cagcagtcca ggaggtgcag cgggctacag   7740
atcatccgcg aggccaggac gtcctcggcg gtgtacgggc cgcgtccgta catcatcgcc   7800
tcggggttgg tgctgccgtt gttccgcagg gtggccgcga cctgcgccaa ctgcgcctcg   7860
gtggtgccga attcatgcat gtggcggag gcgaccaggg cgaactgggc caccacgtac    7920
gcgccccaca cctcggtgaa ctccagcggc cgtcccgccc cgaccggtgc gcggtccgcg   7980
ccccgggaga ccagcttgca gccgcccacc acgatggtgt cggcgtaccc ggcgcgcacc   8040
gcggcggacg ccttcagcag cccgcggacc ccggcgttgt ccatgaagga gtcgctcgtc   8100
cagtgcagcc ggccgccgaa cagccgggcc caggaggcac cgtcgtccgg cgcgcccccc   8160
ggccccggcc agtccagctg cacaccgtcc acgtccgcgg gacgcaggcc cgcgtcggcc   8220
accgcctccc gcgccgcctc cagcgccagg tccatcgcac tgcggtgggg gagggacagc   8280
gcctgttcgg tcgcgtgaat gcccacgatc acgggctgcc ggtcactcat ctcagcgccc   8340
ggggccgagc gtcgccgcgc ccgggtagcc gccccgccg tactccttgt cgagcgcgtc    8400
gtagtcccgt gcgcccgaca cggtccgggg cagcgccgcg gcgaactcca ccgacttggg   8460
cttcttgtac gaggcgatcc gcggccggca gtggtcgatg atctcctgtt cgctcacccc   8520
ggcgtccggc tccaggacca cgatcgcctt gacgtcctgc gcccagcggg tgttcggcac   8580
gccgatgacg gccgcctcac ggaccgcggg gtgctgctcg atgcagttct ccacctcggc   8640
agggaagatg ttctccgccg ccgacttgag catccgggtc gtggtgccga ggaaggtgat   8700
cgagccgtcc ggttcccgcc ggccgagatc ggtggtgtgc caccagccgg agcggaagcg   8760
gtgcgcattg acctcgtccc ggttccagta gccccggtgg acgacggtgc cgcgggcaca   8820
gatctcaccg gcctcgccca ccgcgcactc ccggcccgcg gtgtcgagaa tgcggaccgt   8880
cagaccgggg cccggccgtc ccgcgttgcc ggcggccggt cctccgtacg cggccgtgac   8940
cgagaagccg gacagctccg tctggccgta gccgcggccg gccgcaccgc cgctgcgggt   9000
gaaccggctg gtgtcggtgg tggccatgcc ctcccacaga tggggcgcca cggtcgcccg   9060
cagccgggag aggtcgtgcc ccgtaccgcg gttgagccgg acgatctccg cgaccgtggg   9120
cggcatgagg aacgcgtggg tgcactcctc ggcgacgagc aggtcccgca cctcctcggc   9180
caccactcgc cgcacgatga cgttcttgcc ggccatcagc agcgtcggca tccccccagaa  9240
ctggtagtta ccgatgtgga acatggggcc ggagttgagg aacgccgtgg tgtggtcgat   9300
atcgcccagc caggccgccg cggtggccat cgcgatcaga ttggtgtggg agagcagcga   9360
accgcactgc cgcccgctca tcgcggcggt gtacaggacc aggacgggag agtccgggtc   9420
gatgtccagg tccgggtcgg cgagcccgcc cgcggcgaga aaggcctcgt acccgtcggg   9480
gtcctgtggc gcgctgtcat ggcgcagcca ccgcgcggtg tcgtcggccc ccagcgcctc   9540
ccgggtccgg gcgacggtct cgtggatctc ctggtgctgc cagaccacga ggtgcgggtc   9600
gaagtcccgc agggcgaact ccatttccgg cggcgcccag cgccagtagc cgacgcagac   9660
catcgcgccg agtttgccgg ccgcggcgat cagttcgtag accggaacg agttctgtcc    9720
cagccacatg atccggtcgc gcgcggccgat ccccgaagcc gccagggagc cggccagccg   9780
gttgacccgg tcgtccagct cgggccaggt gagccggaag gggccgtcga ccagggcggt   9840
acgcccgg tgcgaccggc ggtgttcgcg caggacgtcg ccgatggtcg tgtgctgcaa     9900
ggtggctcct aggcggtcgg ggacccggtc agaccgtggc cggcagggcg gcacggtga    9960
acagatcggt gaagttgcgc cgcgtgatca ggtcgcggac cccggggtcc accccggcga   10020
acagctcggt caccacttcc tgggtgcgcg ggaaggtgcc ctccaggtgc gggtagtcgc   10080
```

```
tgccccacag cacgttggtg tagttcatcg ccgtgaccgc gccgatcgcc gtctcgtcgt    10140
gctggaagga cgcgtacacc tggcggcgta ccagctcgcc ggggagcatc gagagcttgg    10200
gccgtacgaa catgccgtgc tggcggtagg cctcgtccat ccggtcggcg agggcgggca    10260
cccaggcgca gcccgcctcg gcgatgagga cgcgcagccc cggatggcgg tcgagcgctc    10320
ccgaggcgac cagctgtgcc acggcccgct gcgcggggaa cagggtctcc acgtagttga    10380
tgaccgcgcc gccggggccc cgcgcgacca cggtgtcggc tccggtgccg atgtggatgc    10440
tcaccgtcat gcccgcctct cggcggcgg cccacagagg ctcccacacg tccatgttga     10500
actcccggcc cggcggggga gtcgcggcga ggaagaccgt ctggtagccc atgtccgcgg    10560
cccgccgcag ttcggcgacc gcgtcgtcgg tgtccagcat ggacaccatc gcggcgccga    10620
ccagccgcgc cgacagggag aggaagtccg acttcagcca gtcgttgtag accttgatgc    10680
actcatgggc cagcaccggg tcggtcatca cggcggtcca caggccccgg gagggaaga    10740 ccacctcgcc ccagatgccc tggtcgtcga ggtccttgag ccggatgtgg tggtccagcg    10800
caccgggcgg gcgcatggcg tcggcgaagt cgagcgggtc gcgccgcacg acctggccgt    10860
cgacgtagac cgtctcgcgg ccgttgtcgc gcacacagcg cggcgcccgg tcgcgcagcg    10920
ccgcgggcag ggcgcgctcc cagaggtcgt cgggctccag gacgtgggag tcggcggagt    10980
tgagccagag cttttccatg gaattctcca gacgtgatct gttcggtggg cccgggacgg    11040
cgggcggatc gggacgaggg cgcggcgccg ggcggggcc gtgcggcggg tgtcagcgca     11100
cggtgagcca ggtgtcggcc aggacgggcg cgtccgcgcg gtcggcggcg gtggccagga    11160
cgcggatctc ccccgcttcc tgccaggtgc ggacgcacac ggtcccgccc ggataaagga    11220
cgccggcgaa ccgggtgccg tacgcggcga cgcgggtgac ctcgccgccg aggtgcgcgt    11280
ccaccacggc cttcagcacc atgccgtagg tgcacagacc gtgcaggatg ggccgctcga    11340
agcccgccgc cgcggccacc gccggatccg cgtagcagtc gacctgaagt cgcatgcaca    11400
gcctgagtat gagcagtgcc tggtcctcgc gggtggccag gtgcaggacg cggtccggcg    11460
cccggtccgg ggcgggccgc cgccggtcag ggcggggcc gccgcgaaa ccgccctccc      11520 cgcgcagatg ggcgtccccc tcggcggtcc acaacggccc gtccccgtcg cgacttcgg    11580 agcgcagcac caccaccgcg gcccggcccc ggtccagcac ctccgtcacc cgggtggtct    11640
gaacggcctt cccacacgcc ggcagcggac ggtgcagcgt gatgcgctgc gcgctgtgca    11700
gcatcgccgc ggggtccacg tcgatgccgg gcagggcgaa gccgccgccc gcggcctgcc    11760
cgccgcccgc cacggtcgcg aaggagggca gcacctggag cgcgctctcc agcgtgtagc    11820
gcagctcgcc ggggtcggtg gcgggccgtc ccgcgccgat cgccaggtgg tagaggagga    11880
cgtcgcggtg gtcccaggcg aggtcggtga cgtgggtgc ggccgcgagg acggccggga     11940
catcgagggg catgggaagg ccttctgccg gtggatgagg acggccggcg ggcggtgcgc    12000
gcggggccgg cgggcggtca gagcgcgagc agcgggatgg cgcagagcag gaggtccccg    12060
cccatcgcca gcgagaggct gtgcttgcgc atcgtggact cgtgcgggag gttctcccgc    12120
gagatgctcc gcagcagttt gatcttgtcc acgaggaagg cggcgctcgc caggatgccg    12180
agcagcgccc agaagacgcc gtacggccac agcccggcgc cgatgaacag cagcccgagc    12240
gcggtccaca gcacgccac caccagcgca tggcgcgggc cgtgctgtac ggcgggcgta     12300
cggtcccccg ccttggcgtc accgatcaga tccgggatgc accaccacag ggagcggccg    12360
aacagcagga tgccgagccc ggtgaggaac agccacgcgc tgggcggtac gtccgcccgc    12420
accgccgcat acgtcgacag cgacggcagg aaggcgaacg tcgccccgaa gtaggcgggg    12480
```

```
ttggcgtagc cgcgccgctt gagccggacc ggctccaggt tgtaggcgag gtggagcacg   12540
atcgacagcg ccaccccac cgcgacgagc ggccggccga gccagagcgc gacccagacc    12600
gacagcccga gggcgagcgc catctccagt gccgcgcagg tgaacgcggt gcggacgctg   12660
aggtgctggg tggcgcgggc gatgctctcc ttgccgctgg tgtgggtgtc cgcccggatg   12720
tccagcccgg cgttgagcgg gttctggag atgatcgcga cgatgttggc gaacagcgtg    12780
atgaggacgg gaggggcggt cagactgccc ggacccgtcg ccgcgaggca ggcgccccac   12840
aggacatggc agagatagat gaccggaaag ggatattcca gccggtggat gcggaggagg   12900
ctccgcagcc cttcgccgcg cgcggcgggc agttccgacg tcatgctgga cactcggtca   12960
ccgtcattct caggtcttcg ctcggaccca tcgccggacc gcgcagctgc ggtaccccgg   13020
tctccggatt gacgcacttc agttcccgcc ggcgcagcac cgccgccacc accatccgca   13080
tctccagcat cgccaggtcg gcaccgagac agcggcgggt gccgccgccg aacggcaggt   13140
actcctgggc ggacttgcgc ttgcccagga agcggtgcgg gtcgaagcgt cccggctgcg   13200
ggtagagatc cggctgctgg tgcgccagat agatgcacgg cgtcagccgg gtgcccgcgt   13260
cgtgcggcac cccgtcgatc tcctggccct cgttgagcac gcggttgccg gccaccacgg   13320
cgggcggcga gatccgcagc acctcccggc aggccgcgtc cagcagcggt acgtcctccg   13380
ccgccgcacc gctggaggag gtggccttca gctcgtcgat gatgtcgcgg cgcacctcgt   13440
cgtgctccgc gagccagaac agcgcccagg agattgccga ggcggtcgtc tcgtggcccg   13500
cgaagagcaa cgagacgatc tggtcgcgca gttcgccgtc gcccagcggg ccgagcggct   13560
cctcaccgct gcgcagcacc tcggcgaggg tggccggcga cggctccggc gcaccggaac   13620
ccccgccgcc ggcgctcttg ccgctcaccg ggcacagcag ctccttgtcc aggctctcgc   13680
gctgccgcac aaaggtgcgc cagggagacg gcagggcgtg cggcagccgc agatagcggt   13740
aggcgagggt gcggccgcgc gagcccagca cccctcgat ccaggaggtg aagcggtgca    13800
gcagaccgtg gtccaccggg ccgaggatga tctggctgac gatctgaagg gtgagcctgc   13860
gggtccagtc gggcacctgg aagacggtgc ccggccgcag ttcgtcgatc gccgcccggg   13920
tggcctcggc gatcagctcc tcgtagccgc gcagcgggcg gccgcgcagc cgtgggccga   13980
tcacctggcg gtacgcggcg tgccgcggcc cgttggcgaa cagcagcgag gtgtcgccga   14040
ccagcgggcc gagcgtgtcg gagccctcca gcgtcatgtt ccggtcgccg cggaagacct   14100
ggctgatgat ctccggcttc cacaccagca gggcccggcc gggcggtccg ctcagctcgg   14160
ccacaccgga gcggtcgtcc ttgtgggcgt ccaggaagga gagggtgcgg aaggcgaagc   14220
ggtacttgtt gccgcgcggg gcggtcgtgg ggcgggtggt catcaagcac ctccggaagc   14280
ggcggactcg gcgccgccga gcgccagtgc cgcgagccgc gccgcccgga tgacggtcac   14340
cggcgcgtag atgtccttgt cgtgccagag cccggggtag gaggccgggt cgtcgtgggc   14400
cagcagcgcg tcgcagccgc gggccgccga ccgggcgacg gtccccgggc tccccggggt   14460
acgggtacgc atcaggagct gcaccatgta cgcggtctcc tccgtggtgc cctgccagcg   14520
tccccaggag ccgtcggcgc gctgggtctc cagcgcccac gcggcggccc ggtcgaccgc   14580
ggcccgtgcg gacgggccgc cgaactcggc gagcgcgagc gcacagcagg ccgtggcgta   14640
gtacggcgag gcgtgccact tgtccatcca gctgccgtcg ggcagctggt tgtccagcag   14700
ccagtcgctg atcatccgga tctccgcgcc atagcgtccc gcgtcgtcgg ggcgcaccgt   14760
gacgtgatgg ccgagggctt cgaggatgtg tgcgttggtg ctggtggaag gggtgcgctc   14820
gacgccgaag caggagaagt agccgtcccg gcggaagtgc atcaggctgt cggggcggtg   14880
```

```
cgtcctgccg tgctgcgcca gggcgaagag gacggcggcg gtgtcgtcgg agtcgctcgg   14940
cagaccgggg gcggcggcta tgccctcgtc cgtgagaccc gcttcgaggc tgtcgaggag   15000
cgcggccggg gcctcgtagc gcaggccgga ggcggccagc gagttgagga cccacgcctg   15060
ctcgaagtag acgatcgggg tgatggaggg caccggaccg ccgaaccgcg cctggacgtc   15120
acggaggtag gcgacgcccg gtgcggccgg atcgggcgag gcgcccagcc aggcggcggt   15180
ggcggcgggg gagcagccga ccgagccgtt gtgcggcggt gcgccctcgt gcggccgggc   15240
gccgcggggtg ccgtcgcggg tgatggcctc caggggtgtgc cacagcttct ccggcagcgg   15300
cgcctgctcg gtcatctccc ggacgccggc cagcagcgca ccgtccaggt cgggcgccgg   15360
tgacgtcagg gtggtgccgg accacgcccc gagcttgccg ggcgcctgct cggtcagcgc   15420
ggccagccgg gtgttgatgt ccgcgagcag ggacggggcg acgaactcga cgccgatggt   15480
gtcgggtacc ggaccggcga gcagaccgtc ctggagggcg cccagaccgc cggcgcaggc   15540
cgccgcgagg tcgtcgtggg gcgggtgcgg cgcgccggaa tccgtccggg cgagttcggt   15600
cagcagcgcc tcgaccgcac tgagcgtggg caccagcccg tacccgtcgg gagcgcccca   15660
actgccgtcc tggttctgct ccttgaccag gtagccgagg cgttcccggt ggccgtcgag   15720
ccacggggcg agggagacca gccgggcggt gtcgtacacc gacggagcga ccaggcccca   15780
ggggtctgcg acgtcgccg cgagcagcgc ggccgcctcg gcctcgcggg gggcgggcgt   15840
gggctgagcg ggaacttcga gcacggctct cccttggtcg agcggcggcc tggcggacga   15900
cgcggcgatc gatgaatcat ttatataatc caacttagag tgctagtctc gcaactgttg   15960
ttgtcgttcg tggtgttggg ggctggctgg tggctgggct ggtgtgggag ccgacgtctg   16020
cggggtgggg tgcgcgggtc gaggggttgg atctgcgggc gccgttgggt gcggagtgtg   16080
cggcggcgtt ggtggagctg ttccgtgcgc ggcatctgct ggtgttttcg ggtcagggct   16140
tctcgttgga ggagcagatc cggttcatgg ggcatttggg gccggtgctg catgaggagg   16200
gttcggggat cgggtttgtt tcgaatgtga aggaggggc tgctctgggg acgagtgagc   16260
tgtcttttcca ttcggatacg gggcattgtg cggtgccgtt ggaggcggtg tcgctttttg   16320
ctgaggatgt tgagggggtgt gtgacgtcga cgcggttttgc gaatgtggcg gcggcgtatg   16380
gtcgtttgcc ggcggatttg cggtcgcggg ttgcgtcttt ggtgtgtgag aacgcgatgc   16440
cggtgtcgtt ggacgccggg aatgtggggt tgtcggtggc ggaggggatg ccgccgggcg   16500
gagcatccgg tggtgtggcg tcatccggtg tcggggagc cggggctgat ggtgaatgcg   16560
aatcagacga cgcggattgt gggtcttgag gacgcggaga ccgggagct gctgaggag   16620
ttgttctcgg tgatgtatgc cgaggatgcg gtgtatgagc attcctggca gcaggggat   16680
gtggtgatct ggcacaacct ggcggttcaa cacgcccggg gtggcctgga agggaatggg   16740
cggcggactc tgcgccgggt ggcgttgggt gagaaggggtt tttgggagca gtgcccgacc   16800
ctgcgttacg ccgatttcaa aaaccaccgg aacaccaccg aggacaaggc caccgcgtaa   16860
tgaggcgcac gctcttcacc cccgagcacg agcagttccg ggagaccgcc cgtgcctact   16920
acctcaggga gtgcgtgccc cacgcggagg aatgggagca ggccggaatc gtcagccgcg   16980
aggcctggag cgcggccggt gcggccggtc tcatcgggtg ggaattcccc gaggagttcg   17040
gcggacaggc catccgagac ttccgctaca acgccatcat ggccgaggag atggcggcca   17100
ccggcacggt gggcatcggc ctcgggctcc agaacgacgt cctgccctcc tacctgtcgc   17160
acctcaccga ggagcagcag caccgctggc tccccgggat cgtctccggg cggaccatct   17220
gcgccctggc cctgtccgag ccggacgccg ggtcggacct ggcggcgatg cgcaccaccg   17280
```

```
cccgccgcga gggcgaccac tatgtgctca gcggccagaa gaccttcatc accaacggca      17340
tcctcgccga cttcgtgatc gtcgcctgca agaccgaccc ggacgcccgc cacaagggca      17400
tcagcctgct ggtcgtcgag cgcgggatgc ccggcttcga gcgcggccgc cggctggaca      17460
aggtcggcct caaggcccag gacaccgcgg agctcttctt ccacgacgta cgggtgccgg      17520
cggcgaacct cctcggcgcg gagggccgcg gcttcgcgta catgatggag aacctgccca      17580
ccgagcggat cgccatcgcg gtgagcgcgc tgggcggcgc gcagcgcgcc ttcgagctgg      17640
cgctggagta cgccaagacc ccgcacggcg tttcgggcag cccatcggca cctttccagg      17700
ccaaccgctt cgcgctggcc gacatgcggg ccaagctcga cgcggcgcgc acctatgtcg      17760
acggctgcat catggcgctc gtcgagggcc atctcacggc ggtcgacgcc gccgcggcga      17820
agtactggac caccgagacc gcctggcaga tcatcgaccg ctgcgtccag ctgttcggcg      17880
gatacggata catcaacgag tacgaaatcg cgcgcatctg gcgcgacaac cgcattgagc      17940
ggatcttcgg cggcacctcg gagatcatgc aggagatcgt ggggcgctcg ctggggctga      18000
catcggcgac cgtgaggaag caggaatgaa caacaagctc gtctcccact tactggacag      18060
cgcggacccg gcggtgcggg ccaaggccat cgaggccgcg gcactggcgc gccaatgggc      18120
gagacccgtc cagcaggagc tgagcgacaa ggtgtacgac acgctcgccg ccacggtgtg      18180
tgtgatcgcg cccgaactgg acgtcgccga ccatgcgttg ctcgtcgagt acagcctgtg      18240
gctctatctg ctcgacggca ggctcgacga cttcgagcac tacggcaccc ggcccgagga      18300
cgtcggccgg cgggtgatcg ccgtactccg cggcggccgt gccgaggcgc gagccgacga      18360
cttcttcgag acctcgctcg ccgcactggt cgaggagctg cggacccggg acggctgctg      18420
cgggctgctg gagcggttcg tgctgcggct ggtggacggg gtccgtgcgg gggtgcgcca      18480
ggcggtgctc agtcggcgga tcgccgaggg cgcggagccg ctgcccacca tggaggactt      18540
cctcgaactg gcctaccggc acgtcaacta ccgcagtgtg gccctggcac tgctgatcac      18600
cgtgggcgag cgtccggaca gcgcggcgca ggagcggctc gacgcggccc tcgtcccggc      18660
gtcgagggcg gtccggctcg ccaacgatct gcggacctgg gccaaggacg ccgaagaggg      18720
caccttgaac gtcgtccagc tggtcgccgg cgacggcacc cccatgacgc cgcacgccgt      18780
acgcgaccgc atccaggcct accgcgacga gcaggcccac ctcctggacg agctgcaccg      18840
cagcgccccg gcctccgccg ccgcgctgga gaacaacctc agggtcgcca tcgacctgta      18900
caccgtcgac gacctccaat tcgacctgcc ggacgccgaa caggccgtcg gctagggcgg      18960
gttcgcgccg tcccgtccgg ctcgcgacgc ctgccgtgag cccccgccc tccggggcgg      19020 gcgacgggac gtcgtgcgca ccccggccgc cgtccggccc cctcccgatc aaaggacgcg      19080
atgtgaccga cgcttcctcg caccccgcgc cgctgccccg cgcgccgc tgcccgctgg      19140 acccgcccga ggagtacgcc gcgctgcgcc ggaccgatcc ggtcagccgg ctcgccttcc      19200 ccgacgctc ggccggctgg ctcgtcaccc ggtacgacga cgtccgcacc gtgctgacgg      19260
acccgcgctt cagcgcccgc ggcgacctgg tgacctcccc cgtcgccagc cagctgcgcc      19320
gccgcgacgc cccggcgccg gggatgttcg cgcggatgga cccgcccgac cacacccgct      19380
accggcggct gctggcccgg cacttccacg tgcgccgggt gcgcgccctg gtaccggcca      19440
tcgagcgcat cgtcgccgac cggctggacg ccctccgccg cgccgggccg ccggccgacc      19500
tggtggagat cttcgcgctg cccgtgccga ccctggtgat ctgcgaactg ctgggggtgc      19560
cctacgagga ccgggcggcg ttccagagct ggaccgcgag catggtgtcg gtggacagca      19620
cccgcgagga gtcggacgcc gcggtcgccg ccctggccgg gtacgtccgg agcctcgtcg      19680
```

-continued

```
tggccaaacg cggcgtaccc gcccacgacc tgctggccga cctggcggcg gacggggagc    19740
tgacggacga ggagacggcg aacatcgggc tgagcgtcct ggtggcgggg cacgagacca    19800
ccgccaacat gctctccctc ggcgccttcg ccctgctgcg gcaccccgag gagctggccg    19860
ccttccgggc ggatcccggt ctcacggagc aggccgtcga agagctcctg cgctacctca    19920
ccatcccgca gttcggccgg gagcgcgccg ccctggagga cgtcgtgctc ggcgggcgca    19980
ccctcgcggc cggcgaggtg gtcgtcgcct cgctgctctc cgcgaaccgc gacccggggc    20040
gcttcgacga ccccgacacc ctggacctcc gccgcccgtc ggccgggcat ctggccttcg    20100
ggcacggcat ccaccagtgc atcggccagc agctggcgcg cgagcagctg cgggccggcc    20160
tccgggcgct gttcacgcaa ggtcccacgc tccggctcgc ggtgccgccg gaagaggtgc    20220
cgatgtgcga ggactccctg aactacgggg tgccgcaggc tgccggtcacc tggggcaccg    20280 gccggtgacc gccgccgagg tgccgcgcgt ccgcgccgat ctcgacgcgg ggtggctgga    20340
ggcggcgctg cgcggggcgg gccaccgggt ccgggtgacc ggcctgcggg tggcgccgac    20400
cgaccagggc acctccaccc gtatcccgct ggccgcccgc ttctcgggtc cggacgccgc    20460
ggcgctgccg gaccggctgt tcgtcaagac ctcgctctcc catccgctgc acgaggtcat    20520
ggcggccgcg ggcatctacg tcaccgaggt acggatgtac caggaggtgc tgccggcggc    20580
tcccgtggcg gtgcccgccg tgtacgcgtc cgggtacagc cccgacgacg ggcgcttctt    20640
cctcctgatg gaggacctga cggcgcgcgg ctgcgactgg ggggcggcgg ggcagctgct    20700
cacgcccgac gcggtggccg gtgtgctgtc cgaactcgcc gcgttgcacg ccaggttccg    20760
tgatccggtg cggcggggcg ggctgtcgtg ggtgcggcgc tgtgcggccc cggcggggtc    20820
gacgacgtac gcctatgcgc ggcgcggggc cgaggcggtc tgtgcggcgg cggaccgcgc    20880
cggcccggcc ggggaggagg ccgggccgga gtcctggatg gccgccttcg cgcggctgac    20940
ggccttcgac gacgcggtgc ggcccaccct gctgcacggc gatccgcacc cgggcaatct    21000
ggcgttcgtg cccgggggc ggcccgtgct ggcggactgg caggccgcgc gccgcgggca    21060
ctgggcgcac gatgtggcct acctcctcgc ctcggcgctg agccccgggg accgggcggc    21120
gcacgaacgg gacctgctgg ccggctatct ggacgaggtc gcggcccggg cgccgcggt    21180 gccgtccttc gccggggcgt gggacgccta ccgggcgcag atggtctacg gcctgctgat    21240
gtgggcggcc accccggagg gctcccaccc ggcgaaggtg ctggccgccg tcacccagcg    21300
gttccgcacc gcctgcacgg agctggagag cctcaccgca ctgggtcgct aaatcattta    21360
tataatccaa cttagagtgc tagtctcgca actgttgttg tcgttcgtgg tgttgggggg    21420
ctggctggtg gctgggctgg tgtgggagcc gacgtctgcg gggtggggtg cgcgggtcga    21480
ggggttggat ctgcgggcgc cgttgggtgc ggagtgtgcg gcggcgttgg tggagctgtt    21540
ccgtgcgcgg catctgctgg tgttttcggg tcagggcttc tcgttggagg agcagatccg    21600
gttcatgggg catttgggc cggtgctgca tgaggagggt tcggggatcg ggtttgtttc    21660
gaatgtgaag gaggggggctg ctctgggggac gagtgagctg tctttccatt cggatacggg    21720
gcattgtgcg gtgccgttgg aggcggtgtc gcttttttgct gaggatgttg agggtgtgt    21780 gacgtcgacg cggtttgcga atgtggcggc ggcgtatggt cgtttgccgg cggatttgcg    21840 gtcgcggggtt gcgtctttgg tgtgtgagaa cgcgatgccg gtgtcgttgg acggccggaa    21900
tgtggggttg tcggtggcgg aggggatgcc gcgggcggag catccggtgg tgtggcgtca    21960
tccggtgtcg ggggagccgg ggctgatggt gaatgcgaat cagacgacgc ggattgtggg    22020
tcttgaggac gcggagagcc gggagctgct ggaggagttg ttctcggtga tgtatgccga    22080
```

```
ggatgcggtg tatgagcatt cctggcagca gggggatgtg gtgatctggc acaacctggc    22140
ggttcaacac gcccggggtg gcctggaagg gaatgggcgg cggactcggc gccgggtggc    22200
gttgggtgag aagggttttt gggagcagtg cccgaccctg cgttacgccg atttcaaaaa    22260
ccaccggaac accgccgcgg agaccgcgtc gcgctgtcgc acacctttct gtcggaccga    22320
accaagagga agagttcagt gcacgctgac acagtccagc ccctcgagag cagtgtcgac    22380
ctggcccacc gcaacgcctc gcgggccgcc ggcctcgtca cgcccgccct gcgggccacc    22440
gtcgacacct tcgacaaccg catccgcccg atcgtcgcct accacttcgg ctggatggac    22500
accagcggac gtcccacggc gaacagcggc ggcaagatga tccgggcggc actgaccatc    22560
cttgccgccg aggcctgcgg cggcgacgcc cggcaagccg tacccggcgc cgcggccgtc    22620
gaactggtcc acaacttctc gctgttgcac gacgacgtca tggaccgcga cctggagcgg    22680
cgcggccggc ccacggtctg gagcaagttc ggcaccccg cggcgatcct ggcgggcgac    22740
atcctgctgg cgcgcgcctg cggaatgttc gacgaggcct ccggccacca gggctgggcg    22800
accaaggccc tcatcgacgc gatcgccgag ctggccgcgg gccagatggc ggacctcgcg    22860
ctggagcgcc gcgccacggt caccctggaa gaggccctca ccgtctccga gcagaagacc    22920
gcggcgctgc tgcgctgcgc ctgcacgctg ggcgcgggac tcgtcggcgc gcccgacggg    22980
accagccgcc gcttcggcgc cttcggtatg cacctgggca tggcgttcca gttggtcgac    23040
gacgtgctcg gcatctgggg cgacccggcc gtcaccggca agccggtccg ctcggacctg    23100
cacaacaaga agaagagcat ccccgtcgtc gccgccctcc acagcggccg gcccggctcc    23160
gcggaactgg ccgcgctcta cgccgacacc gaccccatga ccgaggacgg cgcccggcgc    23220
gccgccgaac tcgtcgagct ggccggcggc gcgcctgga ccgagagcga gatcgagcgg    23280
caccgcggcc tcgccgtggc gcagctcgac gccctcggac tgacggaggc gcagcgcgca    23340
cccctgctcg ccctcgccga ctacgtcgcc ttcaggaagc actgatgacc gccgccatcg    23400
tgagtgtcgc cgcgcgcccg ctgagcacgg cggtgcgcca cggcgacgtg gtgctcgccg    23460
accggctgca cctggcgtcg ggcgcccgcg agggccgggt ctaccggctg ctcgccgggg    23520
ccctcagggc ccagggggctg acggtccaca ccggcggggc cgccgtcgcc ggagccgagg    23580
caccccaggg caccgaggca ccgctggtgg aggtcggcac gccggaccag ctcccggaag    23640
cggacggtga cgcgctgctg tgcctggtgc gcgacgacgt gggttcggcc gctgtcgacc    23700
gcgccgagga ggccctggcc cgggtcctgg gcgactggga agcggcgaag ggggaccgtg    23760
cggtggcact ggccgccccc cggtcgttct gtgccggtgt cgaccgcgcc atcgagatcg    23820
tcgaacgcgc cctcgaccag tacggcgccc cggtctacgt acgcaagcag atcgtccaca    23880
accggcatgt cgtcgaggac ctcgcccgcc gggcgcggtt cttcgtcgag gaactcgacg    23940
aggtgccgga gggcgagctg gtcgtcttct ccgcccacgg ggtcgccccg gcggtacgtg    24000
acgcggcggg cgagcgcgat ctgcgggtga tcgacgcgac ctgcccgctg gtgaccaagg    24060
tccatgccga ggcgaagcgg ttcgcggacc gcggcgacac cgtcgtcctg atcgggcacg    24120
ccggtcacga ggaggtcgag ggcacgctgg gcgaggcgcc cgaccgcacg gtgctggtgc    24180
agaacgcggt ggaggcggcg cgcctggagg tcgaggaccc cgaggcggtc tccttcctca    24240
tgcagaccac gctggcgatg tccgaggcca ccgaggtggc cgaggccctg gccggccgtt    24300
tcccgtcgat caaggcaccg cagtccgagg acatctgcta cgcctcgacc aatcgccagc    24360
gcgccgtcga ggagatcgcc ggccgggtcg atctgctgct ggtggtcgga tcgcccaact    24420
cctccaactc cgtacgcctg aaggagctcg cggagcggat gggcacccc gcccaactcg    24480
```

```
tggacgacgc ctcggacgtc gtcctggagc agctgcacgg ggcccggcgg atcggcctga   24540
cggccggtgc ctcggccccg gacgccctcg tccaggaaat cgtcgccaat ctccgcgccc   24600
tcggcaccgt cacggtcacc gagcaccaag tcgcgacgga gaacgtcacc ttccagcttc   24660
ccaaagagct gaggagcgcc cggaaagacc gcgcccgcaa agacttggag aagaccgttg   24720
acagctgttg accttgccgt gccgacgaca ccgctgcgtc gtcccacccg gcagctgatg   24780
ctcggcgggt gggcgtcgg cagccgccac cccgtctcgg tccagtcgat gacgaccacc   24840
gtgacggccg atgcccaggc caccctccag cagatagccg aactcaccgc ggcgggctgc   24900
gacatcgtcc gggtcgcctg ccccagccgg gatgacgccg aggccctcgc ggagatcgcc   24960
cagaagtcga agatccccgt catcgcggac atccacttcc agccgcgcta tgtcttcgcc   25020
gcgatcgagg cgggctgcgc cggtgtccgg gtcaacccgg gcaacatcaa ggaattcgag   25080
ctcggtacac ggagatcctc aaggagatcg acctgcaggc cgcgaaggag accggcaccc   25140
cgatccgcat cggggtcaac gcgggctcgc tcgacccgag gatcctgcgg aagttcggca   25200
aggcgacccc cgaggcgctg ccgaatcgg cgctgcgcga ggcggagctc ttcgcggagc   25260
acgacttcca cgacttcaag atctcggtga agcaccacga cccgatggtg atgatccggg   25320
cgtacgagct gctggccgcg cagtgcgact acccgctcca cctcggcgtc accgaggcgg   25380
gaccggcctt ccagggcacg gtcaagtcct cggtggcctt cggcgcgctg ctgcgccagg   25440
gcatcggcga caccatccgc gtctcgctgt ccgcgccgcc cgtggaggag gtcaaggtcg   25500
gcatccagat cctccagtcg ctcggcctgc gccccggcg cctggagatc gtctcctgcc   25560
cgtcctgcgg ccgcgcccag gtggacgtct acaagctcgc cgaagaggtg agcgccgggc   25620
tcgaagggct tccggtgccg ctgcgggtcg ccgtcatggg ctgtgtcgtc aacggtcccg   25680
gcgaggcccg cgaggccgac ctcggtgtcg cctccggcaa cggcaagggg cagatcttcg   25740
tcaagggcga ggtcgtcaag accgtccccg agtcgaagat cgtcgagacc ctcatcgaag   25800
aggcgctgcg cctcgcggac gagatgggag tggatctcga tgagactggc tgacctcacc   25860
ggcccggccg acctgctgtc cctgacggac ggccaactcg acgcgctggc cgcggacatc   25920
cgctccttcc tcgtggaatc cgtctcgaag gtcggcggcc atctgggccc caacctcggc   25980
gtcgtcgagc tcaccctcgc cctgcaccgg gtcttcgagt cccccaagga cacgctgctc   26040
ttcgacaccg gccaccaggc ctacgtccac aagctgctca ccggccggat gaaggccttc   26100
tcgacgctgc gccaggaggg cgggctctcc ggttatcccg accgcagcga gtccgagcac   26160
gacgtcatcg agaactccca tgcctccacg gccctctcgt acgcggacgg catcgccaag   26220
ggcttcggtc tggccggcgc cgcacaccgc agggtggtcg ccgtcgtcgg cgacggcgcc   26280
ctgaccggcg ggatgagctg ggaggcactc aacaacatcg gcggcgcccc ggaccggccg   26340
gtgatcatcg tcctgaacga caacggccgt tcctacgccc ccaccgccgg cgccctcgcc   26400
acccacctcg gcgagctccg gcgggccgc ggcggggccg gtctcttcga gaacctgggc   26460
ctggcctacc tgggcccggt cgacggccac gaccgcacgg cactcgagcg cgcactgcgc   26520
cgggcggccc cactcgaccg ccccgtggtg gtgcactgcg tgacgcggaa gggccacggt   26580
tacgcaccgg ccgccgagga cgccgacgac tgctggcacg cggtgggcac cttcgacccc   26640
gagaccggcg gcaagtccgc ttccggcggc cgctcctgga ccgcggtgtt cggcgcggag   26700
atgacggaac tcggtgcgca gcggcccgac gtggtggccc tcaccgccgc gatgctccag   26760
cccgtgggcc tggccggctt cgcccgccgc ttccccgacc gggtcttcga cgtcggcatc   26820
ggcgaacagc atgccgccgt ctccgccgcc gggctggcac acaccggact ccacccgtc   26880
```

```
gtggccgtct actccacctt cctcaaccgc gccttcgacc aggtgctgat ggatgtggcg    26940
ctgcaccggc agccggtgac cngcgnacnc gaccgggccg gcancaccgg ccccgacggc    27000
cccagccatc acgggatctg ggacgcctcc tggctctcgc tggtcccggg gctgcgcctg    27060
gcggtgccgc gcgatgccga ggagctcagg acgctgctgc gggaggcggt ngccgtcacg    27120
gacgggccca ccgtcctccg cttcccgaag gcgcaggccg gcccggccgt gccggcgctc    27180
cgccgcgagg ggggcatgga cgtcctgcac gaggcgcccg gcgcccgggt gctgctggtg    27240
ccgaccggtc cgctcgccga cccgtgcctc caggccgcgg ccgcgctgga cgccctgggc    27300
atcccgtcga cggtggtgga cccgcgctgg tccgtccccg taccggaggg gctgccggag    27360
ctggccgcgc ggcacgaact cgtggtgacc gtcgaggaca acctgagcga cggcgggctc    27420
ggcgcgcgcc tgctgcggca gctgtccgag gccggcgcgc cccccaccgt acggaccgtc    27480
ggactgccga cggagttcct accccacggc agcaggacgg ccctcctgcg ccggcatggg    27540
ctcaccgccg acgcctggt cgcacgggtc ggcggatggc tgccacaagc ggcccccgc     27600 tgacccggga gcccgggcgg ccatccctcg cccacattcg gccacatggc gtcaagccag    27660
cctgtaagga gtcgtatccc atgccttcgc accttccttt cgcacgtcag ctcaggctgc    27720
ggcggcttca ccggcacgat gacgacagac tcgtgatcgt gccgctcgac cactccgtca    27780
ccgacggtcc gatcaccggc gggcgccatg tcgaccggct cgtcggggag ttggcggtca    27840
gcggcgtcga cgcggccatc gtccacaagg ggacgctgcg ctgtatcgac ccgatgcgct    27900
tcacgcagat gtcgctcatc gtgcacatga gcgcgagcac cgtgcacgcc cccgacccca    27960
acgccaagta cctcgtcgcc ggcgtcgagg aagccgtacg ccacggtgcc gacgcggtca    28020
gcgtgcacgt caacatcggc tccgacgagg agaagcagca gatccccgac ctggccgcgg    28080
tggccgaggc ctgcgaccgg tggaacgtgc cgctgctcgc gatgatgtac ccgcgcggcc    28140
cccgtatcga caaccccgt gaccccgagc tgatcgccca tgccacctcg ctcgccgcgg    28200
acctgggggc cgacctcgtc aagaccctct acacggggtc gcccgacacc atggccgaga    28260
tcacggacat gtccccgctg ccgatcctgg tcgtcggcgg cccgcagcgc agcggcctcg    28320
acgcgaccct gtcgtacgtg gacgaggcgc tgggggcggg cgccgcggga gtggccatgg    28380
gccgcaacat cttccaggcc gacgagccgg gcaaggtcgc ccgcgcggtc gtcgaactcg    28440
tccacggggg ctcctccgcc cggtcccgcc tcgaagcgga catccaggtc cacgagctgt    28500
ccctgcccgt ctgaccgcac gcgtgtgccg tcgaccttgc ctcaccatat tgtggagaa    28560 ataacatgaa gctgagctgg ctggacgtcc gagcggtcgg ggacgcgaag gaagcgatcc    28620
tccaggaggc gctgcaccac cgcatcgagg gcgtcgtcac ggatgacctc gcggacctcg    28680
aagggctgcc gcccaccctc accaaggtgc tgttccccgg ggcgggcgcg gtgcccgagg    28740
agctggggag ggccgacgtg gtgatcgtgg accggtacg ccacggcatc agcccggccg    28800
aactggcgat ccgtcacccc gaggtgacct tcggccgctt cgtggagatc gtggacgcgg    28860
acagccttga gctggcgtgt gagtccgcgc gcagcgagca gctgagcctg ctgctcttcc    28920
gcgacccgac caagatcccg ctggagatcg tgatcgcggc cgccgccaag gccaccggca    28980
gcctgatcac cgtggcgcag gacgccgagg aggccgagat catcttcggt gtcctggagc    29040
acggttcgga cggcgtgatg atggccccca agggcgtcgg cgaagcggcg cacctgaagg    29100
ccgcggccca gctcgacacc ccgaacctga gcctggtcga gctggagatc accgcgacca    29160
gccacgtcgg catgggtgag cgggcctgtg tcgacacctg cacgcacttc cgcgaggacg    29220
aggggatcct cgtcgggtcg cactccaagg gcatgatcct ctgcgtcagc gagacccatc    29280
```

```
cgctgccgta catgcccacc cggccgttcc gcgtcaacgc cggcgccatc cactcgtaca   29340
ccctctccaa ggacgagcgg accaactacc tcagcgagct caagtccggc agcaaggtgc   29400
tggccgtgga cgtcaagggc aacacccggc tggtcaccgt gggccgggtg aagatcgaat   29460
cccgtccgct gatctccatc gacgcggtcg cgcccggcgg ccaggcggtc aatctgatcc   29520
ttcaggacga ctggcacgta cgggtgctcg gccccggtgg cgccgtgctc aacagcaccg   29580
agctcaagcc cggcgaccgc gtcctcggct acctgccgag cgccgaccgc cacgtgggct   29640
acccgattga tgagttctgc ctggagaagt gacaccggtg acgcacataa gcaataaccg   29700
gccccggatc gccgtgatcg gcggcgggat cgccggtctg acggtggccg cgtcgttgtt   29760
gcgggccggc atcgagtgca ccgtgtacga gcaggccacg gtgttcgccg atgccggcgc   29820
ggggatccag atcgcccccca actcggcccg catcctgcac cgcctcgggc tcgccggcgc   29880
actggagagg cgggccaccc gcgcgcacgc catcgagacg cgccgctggc aggacggcgc   29940
gccgctcgcc cgcacggagc tcggcgagcc ctgcgtggag cggtacggcg cgccctacta   30000
cctcatccag cgggccgatc tgcaccgcag cctgctggag ttgctgccgc cggagtcgt   30060 ccggcacagc gccgcatgca ccgccgtcga ggagcgcccg gacggggtca ccctgcgctt   30120
cgccgacggc acgagcgagg aggccggggt cgtcgtcggc gcggacggca tccactcggc   30180
gctccgcaac cacctcgtgg gcgaccgtcc ccggttctcc gggcacacgg tccaccgcgg   30240
cctggtggcg gccgaccggc tgccgtccct cttcgaggtg ccgaaggtgc tcttctggct   30300
gggaccgaac ggccatgtga cgagctatcc gatcgcccag cacggtctgg tccacttcag   30360
cgcggtgatc acctcaccgg agtgggaccc ggaggtgtgg tcggcgccga gccgcccggg   30420
ggaggccgcg gccgccttcg ccggctggaa cgccgaggtc gccgagctga tcggggccgc   30480
gnaacaggct caccactggg ccctgttcga ccgcgactgc gtgggcggnt ggagcaccgg   30540
ccggatgacg ntggcgggcg acgcggcgca cccgatggtg ccgtatctgt cccagggcgc   30600
caaccaggcc atcgaggacg cctgggtgct cgcggatctg ctcggtgccg cggacctcga   30660
tccggggccc gcgctgcggc ggtacgagga gctgcggctg ccccgcgtcc gcgaggtgca   30720
ccggcgctcc cgggagcggg gccatgagtt ccaccttccc gacggccgc agcagcgcct   30780 gcgcgaccgg tcgatgccca cggccgagcg gctggacgac tacgcctgga tttacggctt   30840
cgaggccgcg ccggtcggga gccggtagcc ggcggcggcc gcccgtgagc ccgtagcaac   30900
ctgaggaacg aaggggagag acctcggtgg accagagcac actcgacgcc tatctgcgcc   30960
gcctgggcgt cgagcgtccg cggcgtaccg acgccggagc gctccggctg ctccaggaac   31020
gtcatctcgt gtcggtgccg ttcgagaaca tgcacatccg gtcggggaaa cccaccgcac   31080
tcggccccgc ggtgatcgac aagatcgcgc accgccaccg cggcggcacc tgcatcgaac   31140
tcgccagcgc cttcgagcag ttgctgcgca ccctcggcta cccgcaggtg acggtgctgg   31200
gcgggcgcat cttccacgcc ggccgcttca tggcaccggt ggtgcactac gtgctgaagg   31260
tggagacgcc cgagccgtgg ctggtggacg tgggcttcct gcgcggcagc cgctatccgc   31320
tccggttcga cgtgcgcgag ccccagcagg accccgaggg cgtcttccag ctggccgaca   31380
cggacggcgg cggcatcgaa ctgcgccgcg acggggtgcc ccagtaccgg ctggaccccca   31440 ccccgctgcg cttcgaggac ttcccgccca cctggtgggc ctggacgctc cctgagctgc   31500
ccatgtcgca tctgctggtg gcctcgatcc tggacgccac ggggcggacg acgatggtcg   31560
accagcgccg gctgctggag gtgtcggcg gcggacctc cgagcggctc ctcgacggcg   31620
ccgccgaggt gctggaggtg taccggagcc ggttcgggat cgcgctggac gaggtcccgg   31680
```

-continued

```
cccccgggcc gggccccgag gaggacgatc cggtggtgct ggagcagtac cgtgcgtggt    31740
tccgtgcgca gtacggagac cccgaggtca ctccggtggc gggtggcttc ccgatgcggt    31800
agcggggcgg cccccggaca gcggcagggc gtgcggccgg aaccctccgg ttccggccgc    31860
acgccctcgg cgtctcccgg cggcccctca gcgcacgggc cgtgccttcc agaagtagtt    31920
gtgcacgccg tcggcggtga gcagcctgcg gaaggacatc gtgacccgca tcccggcgtg    31980
cacctcgtcc tcggccgcat cggtgagctc gcaccggaac cggccgccgc cgtcgaactc    32040
gatcaccgcc aggatcagcg gcgggtgcgg ggtgaagccc agatggtcga ccgtgtaggt    32100
gacgacggtc gccggcgtgc cgtcgagccg ctcctcggtc attttgtcga tcgtccggca    32160
gttggtgcac acccgggcgg gaggcagctg ccgggtcccg cagtccgtgc aacggctcgc    32220
cacgaagccg tacttccacc cggctcggcg caacgacggt gcggcggcgg cggttgcgg    32280 cttcggccgg gcggcgggct gccggtcgag gaacccgcgc caggtcagat agtccccgta    32340
cgggagccgg tcgctgccgg ccgccgccgg tgcggcggcc gggaacgcg gcccgccggt    32400 cggtcagtgc ggcgcaggtc cgcaggacga ggacggagac gccgtcaccg atgacgacca    32460
gggcgagggt ctgccccggc tcggcgcggt cgagtgngtc ggcnagcagc aggcccggct    32520
gggcggtgcc cggggttgccn acggccttgn cgaggccgtc cgcgttcccg tccgcggtct    32580
tcccggtacg ggcggacagc cggccggcca cggaccgcag ggcgcgctgg tgcagtccgg    32640
cgacggcgag gtggtcgagc tgctccgccc gcagctccgc ccgctccagc gcgtcgtcga    32700
acgcggcatc ggccagccgg gtgtagacct gctcggtgaa gcgttcctcc gacgtcgtgg    32760
agaccggcgt gtccggtgtg cgccggcggt cgaggatctc ggcggtcacc gaggcgtggg    32820
cgatcacctc ggcgagcggg gggagttcgg ccggccgct gaagaggaag gccgcccccg    32880
catcgccccc gtcgcgttcg tcggcgcttc ccggcagtcc cgtccgtacg tccgcgagca    32940
ccaccagggt gtcctcggcg ctgccgctcg ccaggtgcaa ggcgccggct ccggaccgca    33000
ccgcgccggc catgtcgacg gccatggcct ccggggcgag gccgagcgcc gcatggatcg    33060
ccgcggcatt ggtcttgtcc agatacggcg gggtggcggt ggcgaagagc aggttgcgta    33120
cgctcccgcg ggcttcgggg acggcggcca gtgcggcgcg ggccgcctcg acgcccagcg    33180
tcgtgctgtc ctcgtcgtag gaggcgaccg cacgggttcc cccggcagcc ctcccgccga    33240
gcacggtggc gatcgcgctc cgccggagcc ggaagtacgg cacatacgcg ccgtaggcga    33300
cgagcgaggt caagtgaccc tcccggtaaa agagtgagat ccttatgatt atctaactgt    33360
atcggctcta gggaggggga gaccgtgccg tcacacggca tccgcgacaa ggtcgcgatc    33420
gtcggtatgg ggtgcaccac gttcggggag cactgggacg cctcggcgga cgacctcgta    33480
ctggaggcgg tccgggccgc ctgtgcgtcg ggcggggtca gcgacgtcga ggtcgacgcg    33540
tactggctga gcaccctggc gtcggggaac tccggactcg cgctgtcccg cccgctgcgc    33600
ctgccgtaca agcccgtcac ccgggtggag aactactgcg ccggcggctc ggacgcactg    33660
cgcaacgcct gctacgcggt ggcgagcggc gcgtacgaca cggccatggc cgtcggggtg    33720
gagaagctca aggactccgg catgtccggg ctctcggccc ccgccgtccc cggcgacggc    33780
accgaacccg atctcaccgc gccggccgcc ttcagcctgc tcgcccaggc gtacgggcac    33840
aagtacggcc tggccgacgg gacgctccgt gacgtgctgg accggatcgc gtggaagaac    33900
cacgccaacg gcgcgctgaa cccgcgggcg cacttccgcc gggcggtgtc gagggagacc    33960
ctccgcaaag cgccgcgcgt ggcgggcgag ttggggtct tcgactgctc gggcgtgagc    34020
gatggcgcgg cggcggcact ggtggtacgg gccgaggacg cctaccgcta caccgaccgg    34080
```

```
ccgctgttng tgaaggcgct ggcgctcgcg gtcggcccgg ccaccggcac cgccgacccg   34140
gagtacgact tcacctcatt ccccgaggtc aggcactcgg ccgcggacgc ctaccggcag   34200
gccgggatca ccgaccccgg ggccgaactg gcgctggcgg aggtgcacga ctgcttcacg   34260
gtcaccgagc tggtgctgat ggaggacctc ggtttcgcgc cgccgggcga ggcctggcgc   34320
gcggccctgg acggcgcctt cgaccgggac ggcgccctgc cggtgaatcc ggacggcggg   34380
ctgaaggcct tcgggcatcc gatcgggcc  tcggggctgc ggatgctgtt cgagtgctgg   34440
ctgcaactgc gcggggaagc gccccggag  gcgcccctgt ccgcgtccgc cctcgggcgg   34500
gggctggcgc tcacccacaa cctcggcggc ggtccggggg agtgcctgtc gttcgtgtcc   34560
gtcgtcgggg tcgagccccc ggcgtcggcg aagcgtcatc acaccagcgc cgtcacacgg   34620
acggcatgag ggggaggaac agcatggcga agatctgtgc cggccgggtc gtcgtgatca   34680
cgggcgcggg caacgggatc ggccgcgcgc acgccctggc gttcgccggg gccggagcgc   34740
gggtggtcgt caacgacctc ggcggggcca gggacggggc cggcagctcg accgccgccg   34800
ccgagacggt ggcggccgag atccgggccg ccggcggcga ggccgtggcc aacttcgacg   34860
acatctcgac ctgggacggt gcccggcggc tgatcggcca ggccgtcgag cggttcggca   34920
ggctggacac cgtggtcaac aacgccggga tcctgaggga ccggacgctg gtcggtatga   34980
ccgagcagga ctgggacgcc gtggtcgcg  tccatctcaa gggcaccgcc gccgtgctcc   35040
accacgccgc cacccactgg cggcagcggt cgaaggcggg caaggaggtg gcaggacggg   35100
tcatcaacac cacgtccacc tcagggcttt acggcaatcc ggggcagtcc aactacgcgg   35160
cggcgaaggc cggtatcgcg gccctgacga tcagcgcggg gcaggagctg ggccggtacg   35220
gcgtgaccgt gaacgcggtc gcaccggccg ccctgacgcg gatgaccgag gacctgggcg   35280
tcatgccgga cctggccgca cagcatgatc tggcgccgga gagcgtgccg ccggtcgtcg   35340
tctggctcgg cagcccgctg tccgggcatg tcacgggccg ggtcgtcacg gtcttcggca   35400
gccggctctc ggtggcggag ggctgggtcg acggccccgc cgctgtcggt gcggagcgat   35460
gggagccgga gactgccggc gaggcgctgg acaagctggt cgagcgggcg ccccccaacg   35520
ccgatgcgtt cggtaggcgc tccgagtgac ggtccgggga ccgctcgggc ctggctgacg   35580
ctcagtcgag gagttccaga cgggtattgg cgccgctcgc attcaattcc ttctccatac   35640
gggaaatgtg acggcgccaa tgggcctcgg cctcgtcggc ctcgcccgcc tgaatcagct   35700
tcaccaactt cacgtgctct tcatgatcac gtcgggtgcc ggtctttccg ccggtcgcaa   35760
tatgcggact cttggcctgg tagaagatgc attgcagcgt ctcgtgcagt gccagcatcg   35820
cccggttgcc gttcaattcg accaaagtcg cgtgaaatgc tgccttggcc tcggcgagtg   35880
cggcggggtc gtccttcgcc tcttcctccg tggcgagcgc ctcgtgcagc cggccgatgc   35940
cggacggggt gtgccggctg gcgagctgtc gtacgcaggg cggctcgatc gaggcgacga   36000
gctgaaacat ctcgcccagg gtggtctcgc ggtactccag gatgagcccg aggtagcggg   36060
cggccaccat gggatcgggg gcgttgaccc gggcgccgcc gtgcacgccg cggcggacgc   36120
tgatcagcgc ctcggactcc aggacgcgaa tggcctcgcg cagggtgggg cgggaaatgc   36180
cgaactgctc catcagggcc gattccggcg ggagtgcgtc gcccggctcc agttcgcccc   36240
ggatgatgac gcgcgcagg  ctggccgcga ccaattccgc ggtcttcggg acacgcacac   36300
gaagtgccgc cccgtttcgc ttctggggtc ccttatttac cgctcgggtt gcttcagtca   36360
aggccgcttc ctcctaggtg gcgcgcatcg acgacgcggt gcgagcgaaa ttgcagtgag   36420
cacctttacg ccctgttgag tcgattgcat taaatgaatc aatcaggatt actgagtgta   36480
```

```
gcaaggnnct gcncgccgaa atgtggaccg tctgtgatcg cacggtaact cagctgtgac    36540
cctgggtgga tggggcgggc gcgaatggcc ggatgacagt gcatcagggg gatggtagcg    36600
ttaaatcagt taactaagtt atgccttagg gggtggggtg tgggcaggct tgagggggaag   36660 atagcgatcg tcaccggtgc cgcgtcgggc atcggagcgg tcaccgcgga gcggctcgcc    36720
gcggaggggg cccgggtggc gctcgccgac ctggacgagg ccggcgtgca aagtttggcc    36780
gagaagatcc ggggcgcgga cggcacgcac gcgatcggca tcacagcgga cctggcggac    36840
ccggcatcgg tgcgcgccat ggtggccgcc gccgtcgagg agttcggcgg tctggacatc    36900
ctgcacaaca cgccgcggc gaccactctg cgtcctccc tggacgtgcc ggtggccgac      36960
gccgaccccg aggtgtggga gcggacatgc gggtcaacct cagcggcgcc atggtcgcca    37020
cccaggccgc gctgccccat tcatcgcgc gcggcggcgg ctgcgtcatc aacacctcct    37080
cggccgccgg actctccggc gatctgagcc acccggcgta cgcggcgtcc aaggccgccc    37140
tcatcagcct gacgcgttcc gtggcgaccc aggcggggccg aagcggcgtg cgctgcaacg   37200
cgatcgcgcc cggtctcatc atcaccaggc ccgaacgcga ggccgcctac cgggtgatgc    37260
tgccccacca cctcaccacg cggctgggac ggcccgagga cgtcgcgtcg gccgtcgtct    37320
tcctcgcctc cgacgaagcc tcgttcatca ccggacagac cctcgtcgtg gacggcggac    37380
tgctcgcaca ccagccgtac tacgcggatc ggagggccga gtcgtgagcg gcggcccgga    37440
cctcgcccac cgcaccgccc gcacccggct ccggccctgg ctcggtctgg tccccggccc    37500
ggctgcgggc ccggccaccg cggccgccgg cggtgtcgag atcggtctga cctggcacgg    37560
cggcgcggac atcgatcccg cccggcccgg cagtgagccg gtggtgcagg ccctgtgcgg    37620
gctgatgcac ctccatgggc aagaggcggg acgaccgcgc cggctcgggc tggaagcggc    37680
ctcggccgcg gccggagtgc tggccggcca gggcgtcctc gccgctcacg tggggcgcgc    37740
ccgtggcatc ccggtcgacg ccgtggagac ctccgtactg cgcgccggca cgttactcgc    37800
cggccagtac accgccgagg ccacctcccc cgacccgtgg ggaccctcgg tcaagggga    37860 cggcggcccg ccgccgttcc gcagcgccga cggacccctc ttcgagatcg agaccttcga    37920
cccggcccgg tggctggcgt tctggcgcan cctcggngcg ganaccgccn tactgggccg    37980
tgnctggacc gccttccagc accgctacct caanggccac tgcctgntga ccgcngcact    38040
gcacanggac ncggccggca cgccctggcc ccggatcgtc gcggccgcac aggagcacgg    38100
gctcagcctg tcggcgctgc gcggctaccg cgacgtactg gccgagccgg gctggtcgcc    38160
gggccagccc cggctgacgc cgctgcccac gccctgcggc ggcaggccgg ccgccgcgcc    38220
gcagcgcgcc ggaacggacc gtaccgggga cctcccgctg gccgggatcc gggtggtcga    38280
ggccaccagc cgggtccaag gcccctcgc cggggcagttg ttgaccatgc tcggggccga    38340
cgtgacctgg gtcgagccgc cccagggcga cgcgagcggg atgggctccc tgtaccaccg    38400
cggcaagcgc cgtacgggcc tcgacctcag ccgtccggcc ggccgggacg cgctgcgcga    38460
actcatcgcg gaggcggatg tcttcctgca caactggcgc cccggaaagg ccgccgaatg    38520
gggcttcgcc gccgggaac tggccgtac gaaccccgg ctggtcttcg gcgannnnnn     38580
ngtgnaaata gtactttcn tccgttagaa gccntactca ngacccttta ngnaaagttg    38640
attgngactt cgttggaaca ttcatacgcc ctttactaga ttgcattaac ttgaggccag    38700
tagcagtaac tcttaatgat ntgttggttg aaaattttct gaaatganga caggatggga    38760
cgccgaggac acacaggcga ttcctagccc gtaatagtgg tacctatgga ccaatgccac    38820
gaggaactcc naagggattg cttggaatgc catttaatac aacngtgant tgattgantg    38880
```

```
ctaacctctc gtccangttc tttatttata tccaantgaa gggncaccaa ttatgacctg   38940
cagagtatag atgggctgta ttgtgtcggt gatanttgct ttcctggtca aggagtaatc   39000
gctgtagccn ttanangagt gatgngcgcg caccgagtag ctgcagatat tggtgagcta   39060
nagaccgtgt tttaattttc cagattcnng gagantattt atcaacacag gtantctatc   39120
gcaacaattt tagctcaatc aanacaaaga gatgtacttc tggcanactt taatatctga   39180
acttcttcgt tggt                                                     39194
```

PLATENSIMYCIN BIOSYNTHETIC GENE CLUSTER OF *STREPTOMYCES PLATENSIS*

The present invention claims benefit of priority to U.S. Provisional Application Ser. No. 60/952,564, filed Jul. 28, 2007, the entire contents of which are hereby incorporated by reference.

BACKGROUND OF THE INVENTION

I. Technical Field

The present invention relates generally to the fields of microbiology and bacterial genetics. More particularly, it concerns the cloning of the biosynthetic pathway for platensimycin from *Streptomyces platensis* and uses thereof.

II. Related Art

Antibiotic resistance—the ability of a micro-organism to withstand the effects of an antibiotic—is a growing problem in the medical field. Antibiotic resistance evolves naturally via natural selection through random mutation. Because antibiotic action is an environmental pressure, those bacteria that have mutations allowing them to survive will live on to reproduce and pass the trait to their offspring, resulting in a fully-resistant generation. Studies have demonstrated that patterns of antibiotic usage greatly affect the number of resistant organisms that develop, including overuse of broad-spectrum antibiotics (e.g., second- and third-generation cephalosporins), and greatly hastens the development of methicillin resistance, even in organisms that have never been exposed to the selective pressure of methicillin per se. Other factors contributing to resistance include incorrect diagnosis, unnecessary prescriptions, improper use of antibiotics by patients, and use of antibiotics as livestock food additives for growth promotion.

*Staphylococcus aureus* is one of the major resistant pathogens. Found on the mucous membranes and the skin of around a third of the population, it is extremely adaptable to antibiotic pressure. It was the first bacterium in which penicillin resistance was found—in 1947, just four years after the drug started being mass-produced. Methicillin was then the antibiotic of choice, but has since been replaced by oxacillin due to significant kidney toxicity. MRSA (methicillin-resistant *Staphylococcus aureus*) was first detected in Britain in 1961 and is now quite common in hospitals. MRSA was responsible for 37% of fatal cases of blood poisoning in the UK in 1999, up from 4% in 1991. Half of all *S. aureus* infections in the U.S. are resistant to penicillin, methicillin, tetracycline and erythromycin.

This left vancomycin as the only effective agent available. However, VRSA (vancomycin-resistant *Staphylococcus aureus*) was first identified in Japan in 1996, and has since been found in hospitals in England, France and the U.S. VRSA is also termed GISA (glycopeptide intermediate *Staphylococcus aureus*) or VISA (vancomycin-insensitive *Staphylococcus aureus*), indicating resistance to all glycopeptide antibiotics. A new class of antibiotics, oxazolidinones, became available in the 1990s, and the first commercially available oxazolidinone, linezolid, is comparable to vancomycin in effectiveness against MRSA. Linezolid-resistance in *Staphylococcus aureus* was reported in 2003. Community associated (CA)-MRSA has now emerged as an epidemic that is responsible for rapidly progressive, fatal diseases including necrotizing pneumonia, severe sepsis and necrotizing fasciitis.

*Enterococcus faecium* is another superbug found in hospitals. Penicillin-Resistant *enterococcus* was seen in 1983, vancomycin-resistant *Enterococcus* (VRE) in 1987, and linezolid-resistant *Enterococcus* (LRE) in the late 1990s. *Streptococcus pyogenes* (Group A *Streptococcus*) infections can usually be treated with many different antibiotics. Strains of *S. pyogenes* resistant to macrolide antibiotics have emerged, but all strains remain uniformly sensitive to penicillin. Resistance of *Streptococcus pneumoniae* to penicillin and other β-lactams is increasing worldwide. The major mechanism of resistance involves the introduction of mutations in genes encoding penicillin-binding proteins. By 1993, *Escherichia coli* was resistant to five fluoroquinolone variants. *Mycobacterium tuberculosis* is commonly resistant to isoniazid and rifampin, and sometimes universally resistant to the common treatments. Other pathogens showing resistance include *Salmonella, Campylobacter, Streptococci*, and *Acinetobacter baumannii*.

Clearly then, there remains a need for new antibiotics. Moreover, once new antibiotics are found, there is an equivalent need for methods to produce the antibiotics in sufficient quantities, and a reasonably low cost.

SUMMARY OF THE INVENTION

Thus, in accordance with the present invention, there is provided an isolated polynucleotide encoding a plurality of genes from the *Streptomyces platensis* platencin/platensimycin biosynthetic gene cluster. The polynucleotide may be about 5 kD, 10 kD, 15, kD, 20 kD, 25 kD, 30 kD, 35 kD, 40 kD, 45 kD or 50 kD in length. The plurality of genes may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 of the genes encoded by the biosynthetic gene cluster, all the genes of SEQ ID NO:1, or may comprise 1000, 5000, 10,000, 15,000, 20,000, 25,000, 30,000, 35,000 bases, or all of SEQ ID NO:1, and may optionally further including one or more heterologous sequences, i.e., those not normally part of the platencin/platensimycin biosynthetic gene cluster, such as a tailoring enzyme, such as a methylation enzyme, an acetylation enzyme, a glycosylation enzyme, and a phosphorylation enzyme. The polynucleotide may be comprised in a bacterial artificial chromosome.

In another embodiment, there is provided a host cell comprising a polynucleotide as described in the preceding paragraph, wherein the host cell is not *Streptomyces platensis*. The host cell may be *Escherichia coli* cell. Alternatively, the host cell may comprise a polynucleotide as described in the preceding paragraph, the plurality of genes being located in one or more non-natural vectors. This host cell may be a *Streptomyces platensis* cell, an *Escherichia coli* cell, or other suitable cell. The host cell may comprise an attenuating mutation in the coding region of orf9, orf21 or orf34, a modification resulting in the overexpression of orf16 or orf19, or a mutation that knocks out expression of orf28.

Also provided is a method of producing platencin and/or platensimycin comprising (a) providing (i) a host cell comprising a polynucleotide encoding a *Streptomyces platensis* platencin/platensimycin biosynthetic gene cluster, the host cell not being a *Streptomyces platensis* cell, or (ii) a host cell comprising a polynucleotide encoding a *Streptomyces platensis* platencin/platensimycin biosynthetic gene cluster in a non-natural vector; and (b) culturing the host cell under conditions supporting production of platencin and/or platensimycin. The method may further comprise isolating platencin and/or platensimycin from the culture of claim (b). The polynucleotide may comprise each of the genes encoded by the biosynthetic gene cluster, or SEQ ID NO:1. Isolating may comprise chromatography, distillation and/or crystallization. The polynucleotide may comprise a modification resulting in the overexpression of orf16 or orf19, or an attenuating mutation in the coding region of orf9, orf21 or orf34.

In yet another method, there is provided method of selecting host cell producing a platencin or platensimycin analog comprising (a) providing (i) a host cell comprising a polynucleotide encoding a plurality of genes from the *Streptomyces platensis* platencin/platensimycin biosynthetic gene cluster, the host cell not being a *Streptomyces platensis* cell, or (ii) a host cell comprising a polynucleotide encoding a plurality of genes from the *Streptomyces platensis* platencin/platensimycin biosynthetic gene cluster in a non-natural vector; (b) mutagenizing the host cell; and (c) screening the host cell for the production of the platencin or platensimycin analog. The method may further comprise culturing the host cell under conditions supporting production of the analog.

In still a further embodiment, there is provided a method of preparing a modified *Streptomyces platensis* gene for platencin or platensimycin analog synthesis comprising (a) mutagenizing a gene from the *Streptomyces platensis* platencin/platensimycin biosynthetic gene cluster; (b) transferring the gene into a host cell comprising a polynucleotide encoding a plurality of genes from the *Streptomyces platensis* platencin/platensimycin biosynthetic gene cluster; and (c) screening the host cell for the production of the platencin or platensimycin analog. The method may further comprise culturing the host cell under conditions supporting production of the analog. The host cell may be a non-*Streptomyces platensis* cell, such as *E. coli*, or may be a *Streptomyces platensis* cell.

In still another embodiment, there is provided method of preparing a modified *Streptomyces platensis* gene for platencin or platensimycin analog synthesis comprising (a) introducing a polynucleotide encoding a tailoring enzyme into a host cell comprising a polynucleotide encoding a plurality of genes from the *Streptomyces platensis* platencin/platensimycin biosynthetic gene cluster; and (b) screening the host cell for the production of the a platencin or platensimycin analog. The method may further comprise culturing the host cell under conditions supporting production of the analog. The polynucleotide may comprise each of the genes encoded by SEQ ID NO:1 and/or each of the genes in the biosynthetic gene cluster. Alternatively, the polynucleotide may lack a functional form of at least one of the genes encoded by SEQ ID NO:1.

In yet another embodiment, there is provided a method of selecting a host cell producing a platencin or platensimycin analog comprising (a) providing (i) a host cell comprising a polynucleotide encoding a *Streptomyces platensis* platencin/platensimycin biosynthetic gene cluster, the host cell not being a *Streptomyces platensis* cell, or (ii) a host cell comprising a polynucleotide encoding a *Streptomyces platensis* platencin/platensimycin biosynthetic gene cluster in a non-natural vector; wherein the polynucleotide comprises a mutation that knocks out expression of orf28; and (b) culturing the host cell under conditions supporting production of a platencin and/or platensimycin analog. The host cell may be is a *Streptomyces platensis* cell or a is a non-*Streptomyces platensis* cell. Step (b) may comprise culturing the host cell in the presence of an aromatic compound. The aromatic compound may be a non-natural aromatic compound. The method may further comprise subjecting the analog to a synthetic process that adds one or more aromatic structures to a platencin and/or platensimycin terpene core.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Superposition of PTM (yellow, thicker sticks) on ecFabF, with thiolactomycin (green) and cerulenin (cyan) shown for reference. Side chains of importance are labelled and colored as described above. The side chains from apo ecFabF are coloured magenta. (FIG. 2B) Interactions between the benzoic acid ring of platensimycin (yellow) and ecFabF (C163Q). Side chains of importance are labeled and colored green. (FIG. 2C) Interactions of ecFabF with the amide linker and terpene moiety of PTM. Color scheme same as in FIG. 2B. (FIG. 2D) The solvent-accessible surface area of FabF, colored according to electrostatic potential. PTM is depicted as a stick figure and colored yellow, and is shown to be partly exposed to solvent. PTM buries 345 Å2 of solvent-accessible surface area on ecFabF, as calculated with areaimol. Of that surface area, 122 Å2 is a direct result of the terpene portion of the molecule, highlighting its important contribution to PTM binding. Significant interatomic distances (in angstroms) are marked in FIGS. 2B-C with red dashed lines and numbers. Adapted from Wang et al. (2007).

(FIG. 3A) A 70-kb DNA region from *S. platensis* MA7327 harboring the PTM/PTN biosynthetic locus represented by four overlapping cosmids and (FIG. 3B) genetic organization of the PTM/PTN cluster with boundaries predicted on the basis of bioinformatics analysis. The PCR amplified probe used to clone the PTM/PTN cluster was marked, and the 40-kb sequenced region was highlighted in red.

(FIG. 4A) construction of the Δorf28 mutant and restriction maps of *S. platensis* MA7327 wild-type and Δorf28 mutant strains showing with NcoI (N) digestion, (FIG. 4B) Southern analysis of genomic DNAs from *S. platensis* MA7327 wild-type and Δorf28 mutant strains using the PCR-amplified orf29 fragment as a probe, (FIG. 4C) HPLC chromatograms of (I) PTM (♦) standard, *S. platensis* MA7327 fermentation under conditions optimized for (II) PTM (♦) and (III) PTN (●) production, and *S. platensis* Δorf28 mutant fermentation under conditions optimized for (IV) PTM and (V) PTN production and for (VI) PTM (♦) production in medium supplemented with exogenously added 3,4-AHBA, and (FIG. 4D) structures of MJS1 (∇), MJS2 (◇), and MJS3 (▼), accumulated by the Δorf28 mutant, in comparison with PTM.

(FIG. 5A) 3-amino-2,4-dihydroxybenzoic acid from aspartate semialdehyde (ASA) and dihydroxyacetone phosphate (DHAP), (FIG. 5B) IPP and DMAPP by the MEP pathway, (FIG. 5C) ent-kaurene and ent-atiserene by the first bacterial ent-kaurene synthase, (FIG. 5D) PTM and PTN ketolide acids by selective oxidation and a convergent model for the final steps of PTM and PTN biosynthesis. [OX], oxidoreductases Orf15, Orf17, Orf18, Orf20, Orf22, Orf33; Group I refers to those that are common to both PTM and PTN pathways, whereas group II specifies to those that are unique only to PTM biosynthesis as exemplified by MJS2.

(FIG. 6A) Additional biosynthetic intermediates and shunt metabolites isolated from the wild-type *S. platensis* MA7327 strain. (FIG. 6B) Production of PTM (●) and PTN (♦) by the engineered *S. platensis* SB12002 (iv) and SB12001 (iii) strains with the wild-type *S. platensis* MA7327 as a control under two fermentation conditions for PTM (i) and PTM and PTN (ii) production. (FIG. 6C) Susceptibility of *S. avermitilis* and *S. albus* J1074 to PTM and PTN: 1, negative controls; 2, 4 µg; 3, 4 µg; 4, 2 µg; 5, 1 µg; 6, 0.5 µg of PTM or PTN on each paper disk.

(FIG. 7A) Chemical structures of PMN and PCN, and (FIG. 7B) HPLC traces of the crude extracts from (i) 0.5 ml of MA7237 in SLY, (ii) 3 ml of MA7237 in PCNM, (iii) 30 µl of SB12001 in SLY+resin, and (iv) 30 ul of SB12002 in SLY+resin. The amount of production culture prepared and analyzed by HPLC was adjusted for different strains/media to ensure the final peak areas fell within the linear range for quantitation.

(FIG. 9A) Primary sequence alignment of GriH, the 3,4-AHBA from *Streptomyces griseus* and two highly similar ORFs from the genome sequence of *Frankia* sp. CCI3. Primers (FIG. 9B) "pmnForward" and "pmnreverse" were designed to amplify a ~730 bp internal fragment. (FIG. 9C) PCR amplification of an internal fragment of 3,4-AHBA synthase using annealing temperature to control specificity of primers resulted in a single product with the predicted size of 730 bp.

(FIG. 11A) Restriction maps of the *S. platensis* MA7237 wildtype and SB12001 mutant strains showing predicted fragment sizes upon MluI digestion. (FIG. 11B) Southern analysis of MA7237, and isolated mutants, SB12001 and SB12002, genomic DNAs digested with MluI. Digests were probed with a digoxygenin-labeled nucleotide fragment complementary to the DNA just 3' of orf34 in the orientation depicted above to yield hybridized bands of 3.6 kb for wild-type and 1.3 kb for the mutant strains, as expected.

(FIG. 12A) representatives of ketolide acids, (FIG. 12B) selected 3-aminobenzoates, (FIG. 12C) coupling of the ketolide acid and aminobenzoate building blocks as exemplified between the protected 3-aminobenzoate and PTM ketolide acid, and (FIG. 12D) selected 2- or 4-aminobenzoates.

DETAILED DESCRIPTION OF THE INVENTION

Figure 1:
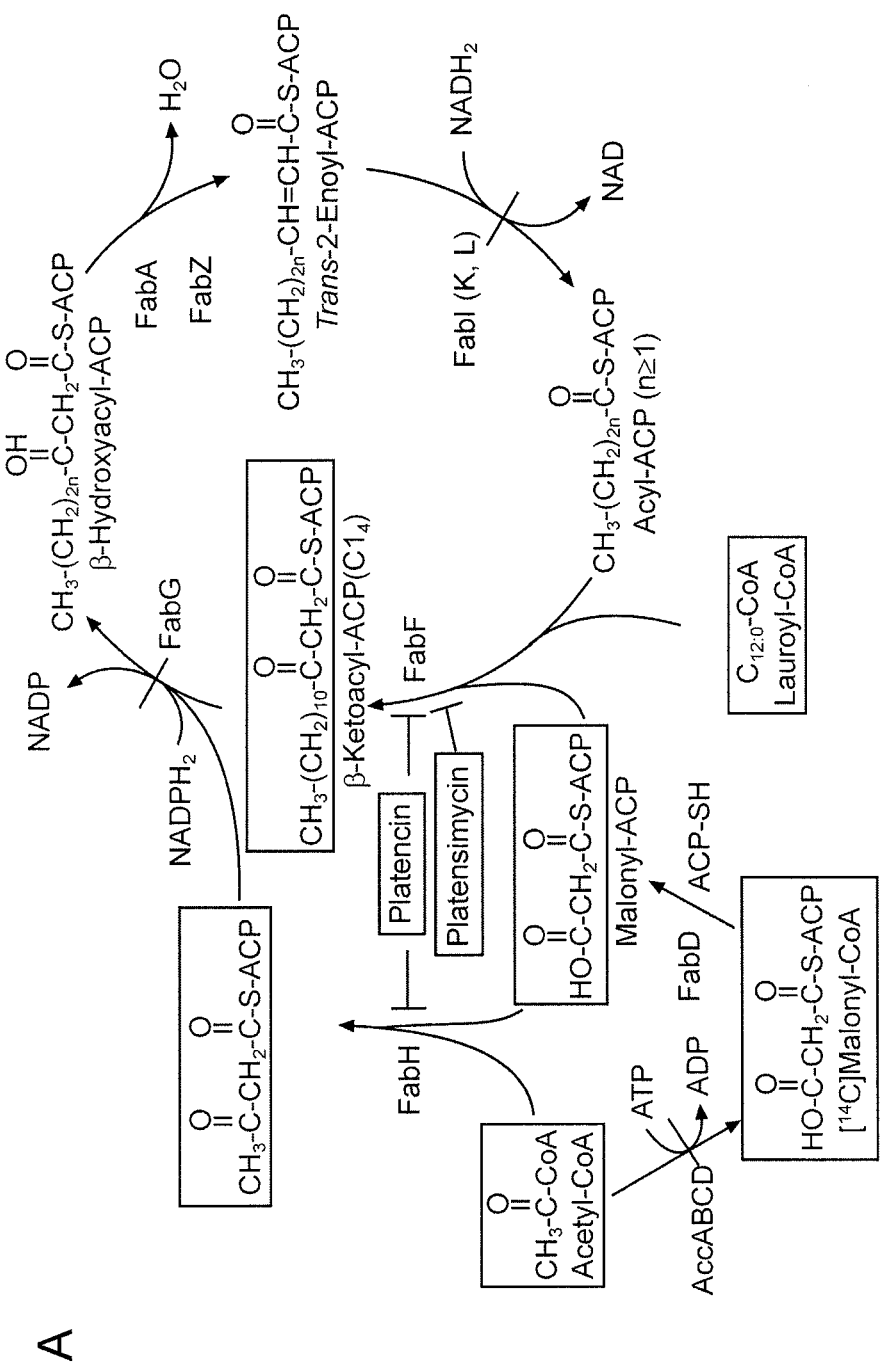
FIG. 1: Schematic of prior fatty acid (FA) synthesis/extension assay to examine FA synthesis inhibition by PTM and platencin. Bacterial FA synthesis initiated with acetyl-CA, which is carboxylated by AccABCD in the presence of ATP to form malonyl-CoA, which is then transferred to ACP by FabD. FA synthesis is initiated by FabH which supplies substrates (acetoacetyl-ACP) to the fatty acid elongation cycle, which includes FabG, FabA/Z, FabI (L/K), and FabF and FabB enzymes. Use of $^{14}$C-radiolabeled malonyl-CoA allows the visualization of Malonyl-ACP (the FabD product), acetoacetyl-ACP (FabH product), and long β-ketoacyl-ACP ($^{14}$C FabF product) via polyacrylamide gel electrophoresis. Using this method, PTM was found to have a 838-fold preference for FabF inhibition relative to FabH inhibition. Adapted from Wang et al. (2007).
Figure 2:
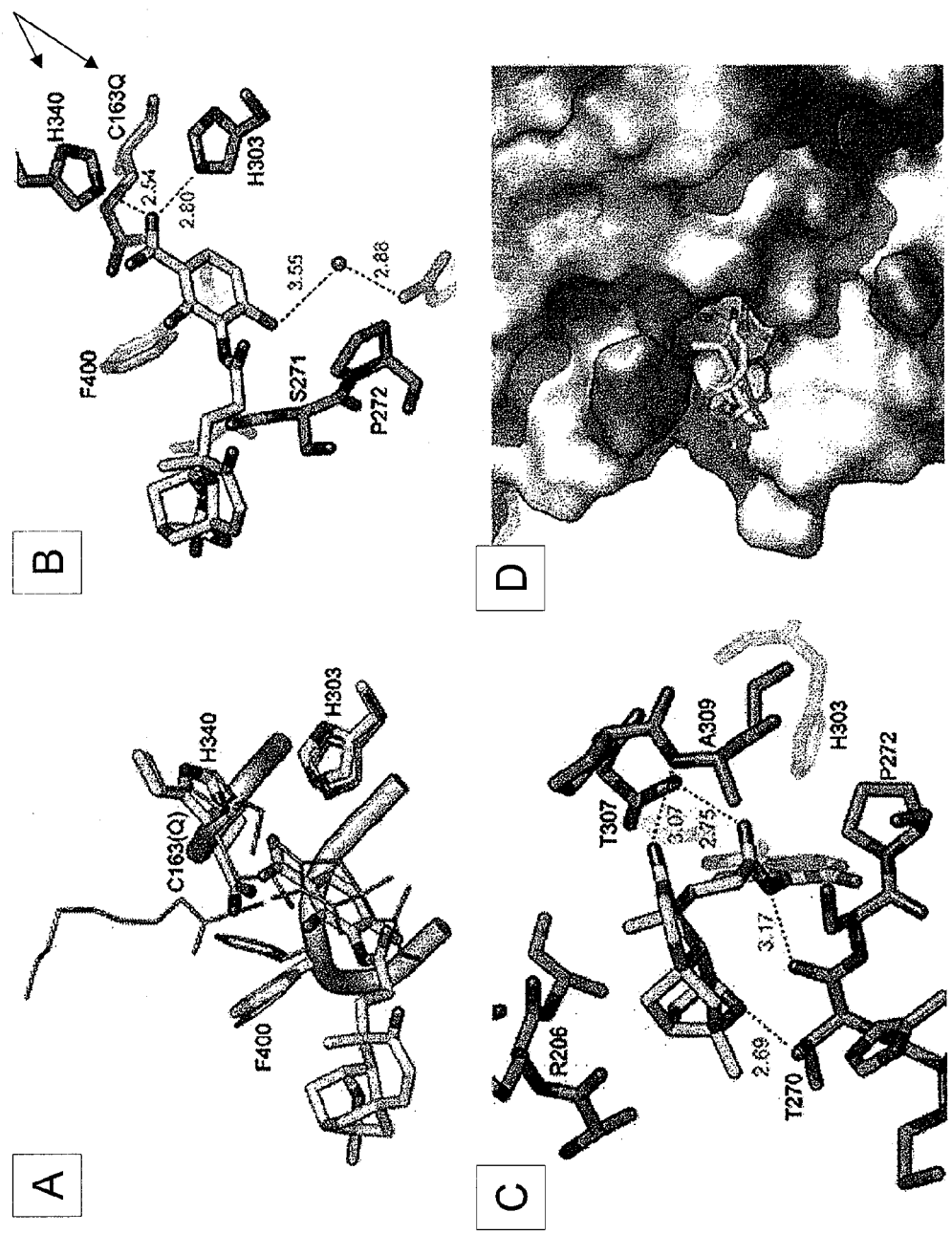
FIGS. 2A-D: Interactions of PTM with a mutant form of FabF in which cysteine 161 was mutated to a less reactive glutamine residue (affording ecFabF) and comparison with the apo enzyme structure.

The discovery and development of antibiotics for the treatment of bacterial infections has been one of the crowning medical achievements of the past 60 years. However, the emergence of bacterial resistance to current antibiotics in clinical use is a major challenge (Walsh and Wright, 2005). The emergence of resistance is inevitable and thus the continued discovery of novel chemotype antibiotics with novel modes of action is vital to overcome drug-resistant organisms. The identification of new chemical scaffolds, or chemotypes is required as resistance continues to effectively disarm currently used antibacterial agents.

One chemotype that is particularly exciting in light of recent natural product screening programs is that of the fatty acid (FA) synthesis inhibitor (Campbell and Cronan, 2001). The enzymes of bacterial FA biosynthesis provide outstanding targets for new antibacterial agents for two reasons. First is the fact that this is an essential pathway in the primary metabolism of all prokaryotes and inhibiting these enzymes is known to produce bacteriacidal results. Second and perhaps most important, is that the enzymes of bacterial FA synthesis (type II) differ significantly from those involved in mammalian fatty acid synthesis (type I) (Campbell and Cronan, 2001). Although chemical mechanisms of FA synthesis in mammals are virtually identical to those of bacteria, the protein sequences and arrangement of enzyme active sites differ markedly between mammals and bacteria thus providing opportunities for designed organism selectivity, as shown by the existence of several selective type II natural product inhibitors of bacterial fatty acid synthesis, including cerulenin, thiolactomycin, triclosan and numerous other compounds (Campbell and Cronan, 2001; Young et al., 2006). That differences in protein sequence and structure allow one to specifically target the enzymes of bacterial FA biosynthesis and NOT mammalian FA synthesis is of paramount concern for the following patent. The sequence, structure and function of target proteins is crucial for understanding why a small molecule displays specificity for one organism over another. However, in the case of FA synthesis inhibitors there is another reason to be concerned with target enzymes.

Organisms producing FA inhibitors often possess a resistant form of the FA synthetic enzyme that is targeted in any organism against which the FA inhibitor is active (Campbell and Cronan, 2001). The producing organism cannot, itself, be susceptible to the effects of the compound it is producing. It has to have some way of either inactivating the compound intracellularly or of exporting the compound to the extracellular matrix. A convenient facet of chromosomal organization in bacteria is that all of the genes involved in the production of a secondary metabolite are grouped together in a discrete locus known as a gene cluster. These clusters include genes that code for proteins responsible for the biosynthesis, regulation and self-resistance. Because of this, finding an antibiotic gene cluster is often the critical step that opens the door to a wealth of information that may prove industrially or medically relevant.

Some scientists have expressed skepticism at the notion of discovering a potent natural product inhibitor of fatty acid synthesis, due to the fact that such compounds would be expected to inhibit polyketide (PK) synthesis (Campbell and Cronan, 2001). This makes sense so long as the FA synthesis inhibitor in question is, in fact, a polyketide. Simply put, a potent FA synthesis inhibitor may very likely target polyketide synthesis as well because of the similarity between FA and polyketide synthases (PKSs). Additionally, by virtue of the similarity between FA biosynthesis and that of PKSs, an organism producing a polyketide inhibitor of FA biosynthesis is very likely to posses a resistant form of the antibiotic producing PK synthase. For example, cerulenin, an inhibitor of FA biosynthesis, is also a powerful inhibitor of PK synthesis in various organisms; cerulenin is a prototypic polyketide. These rationale explain why it is that so few natural inhibitors of fatty acid synthesis have been isolated. *Streptomyces* and *Actinomyces*, the organisms most productive in producing extant antibiotics, are restricted in their ability to produce FA synthesis inhibitors by the close relationship between the synthetic pathways of FAs and PKs (Campbell and Cronan, 2001). Importantly, FA inhibitors do not HAVE to be polyketides. Indeed, a compelling case can be made, using the logic above, that most effective FA inhibitors are not produced via PKS-dependent pathways. Natural product FA inhibitors, regardless of their structural classification, are extremely significant not only because of the uniqueness of their targets and how this uniqueness might allow for pathogen selectivity but also because of their close association with resistance proteins within the producing organism. Such proteins are likely to share significant homology with proteins responsible for resistance within clinical populations. FA synthesis inhibitors therefore represent ideal lead compounds for combinatorial biosynthesis and other methods of analog production.

Antibiotic resistance has been a problem for nearly as long as we've been using antibiotics (Walsh and Wright, 2005). Natural selection of penicillin-resistant strains in *Staphylococcus aureus* began soon after penicillin was introduced back in the 1940s and today drug-resistant strains of *S. aureus* and various enterococci pose a global health problem in hospitals. Increasingly, hospital-acquired infections are resistant to the most powerful antibiotics available, such as vancomycin. Indeed, clinically relevant resistance has been noted towards every class of antibiotic in use today (Walsh and Wright, 2005). Because of how antibiotics work, pathogens evolve and inappropriate use of antibiotics there is now an unquestionable crisis of antibiotic resistance. Identification and clinical exploitation of novel antibiotics against which there is no known clinical resistance and which kill bacteria in a completely different way than other clinical agents would represent significant advances in human health care.

I. THE PRESENT INVENTION

The essential FA synthase FbI is targeted by tricolsan and isoniazid (also an anti-*Mycobacterium tuberculosis* agent); both agents are marketed antibacterials. The initiation condensing enzyme, FabH and elongation condensing enzymes FabF and FabB are essential components of bacterial FA synthesis and consequently are highly conserved among key human pathogens (FIG. 1) (Wang et al., 2007). However, no currently approved drugs target Fab F, H or B. Cerulenin inhibits FabF and FabB by alkylating an active site cysteine; the hydrophobic diene tail of cerulenin appears to mimic the growing acyl chain of the natural FabF/B substrate (Campbell and Cronan, 2001). Thiolactomycin and related analogs reversibly bind the malonyl binding site of both FabH and FabF/B (Campbell and Cronan, 2001). However, neither thiolactomycin or cerulenin display activity sufficient for clinical use. In fact, it is a severe therapeutic limitation that there are no clinically useful antibiotics that target the highly attractive FabB/F/H enzymes of bacterial FA synthesis. Inhibitors of FabB/F/H with structures significantly different from cerulenin or thiolactomycin would represent a new antibacterial drug chemotype with far-reaching ramifications.

In May 2006, Merck disclosed the discovery of a novel inhibitor of FabF, the condensing enzyme of fatty acid biosynthesis, using a whole-cell based approach (Wang et al., 2006). The researchers engineered a strain of *Staphylococcus aureus* that can inducibly express antisense RNA of the FabF gene. With the antisense RNA present, the expression of FabF is essentially knocked-down, making this strain hypersensitive to compounds that inhibit FabF. The group illustrated the potential of such a screen in an earlier paper where they reported the rediscovery of all known inhibitors of FabF plus a few more using this novel screen (Young et al., 2006). Platensimycin (PTM), from the producing strain *Streptomyces platensis*, was discovered in an effort that included screening 83,000 producing strains in 3 different fermentation media, for a total of about 250,000 natural product extracts assayed (Wang et al., 2006). Notably, PTM is the product of terpene biosynthesis, NOT polyketide synthesis.

PTM is a potent inhibitor of fatty acid biosynthesis that is effective against a broad range of gram positive pathogens, including methicillin and vancomycin resistant *S. aureus* and enterococci (Wang et al., 2006). The minimal inhibitory concentration was 1 µM and 2.5 µM for *S. aureus* and *Streptococcus pneumoniae*, respectively, and the $IC_{50}$ was less than 50 nM in single enzyme inhibition assays. PTM has a 200-fold greater potency than the next best inhibitor of FabF, cerulenin, making it the most potent inhibitor for the FabF subunit of the type II fatty acid synthase (Wang et al., 2006). Most importantly, PTM is one of only two new classes of antibiotic natural products discovered in nearly 40 years. Its unique structure, coupled with the fact that its mode of action is not seen in clinical antibiotics, safely secures its place as a new antibacterial chemotype. Although it was not very effective against Gram-negative *Escherichia coli*, this was shown to be due to the active efflux of compound through a tolC dependent efflux pump, NOT because of an insensitivity of the target enzymes in these organisms (Wang et al., 2006). Binding assays as well as a solved crystal structure revealed that platensimycin functions by forming stable non-covalent interactions within the malonyl-ACP binding site of FabF (Wang et al., 2006).

Shortly after announcing the discovery of PTM, Merck reported another related molecule named platencin (PN) (Wang et al., 2007; Jayasuriya et al., 2007). Like PTM, platencin is a product of fermentation of *S. platensis* and contains the same dihydroxybenzoic acid component shown to be important for effective noncovalent association with the malonyl-ACP binding domain of FabF (Wang et al., 2006). Like PTM, platencin shows potent, broad-spectrum Gram-positive in vitro activity. Importantly, PN is highly active against key antibiotic resistant bacteria such as methicillin-resistant *Staphylococcus aureus* (MRSA), vancomycin-intermediate *S. aureus*, and vancomycin-resistant Enterococci, linezolid-resistant and macrolide resistant pathogens (Wang et al., 2007). Detailed analysis of bioactivity reveals strikingly similar similarities between PTM and platencin (Wang et al., 2007). However, key mechanistic differences do exist. Of particular note is that platencin inhibits FabH in addition to FabF; PTM does not inhibit FabH to any significant extent (Wang et al., 2007). FabF and FabB play the roles noted in FIG. 1 en route to long chain fatty acid synthesis. In addition to inhibition of both FabF and FabH with potencies on par with PTM, platencin has shown increased antibacterial activity against vancomycin-resistant *E. faecium* and efflux-negative *E. coli* and decreased activity against *S. pneumoniae* when compared to platensimycin (Wang et al., 2007). This is most likely a result of platencin's dual mode of action (i.e., targeting two, as opposed to one enzyme) and the fact that these microorganisms rely to differing extents on either FabF or FabH. Efforts to understand the mechanism of action of these two terpene-based drug candidates will be vastly hastened by their similarities in structure yet different patterns of FA synthase inhibition. That both compounds likely share certain elements of biosynthetic machinery en route to their production in *S. platensis* adds further excitement to the prospects for compound diversification by combinatorial biosynthetic means, as well as, elucidation of resistance proteins.

Thus, the present invention reports the cloning, via a novel PCR strategy, of the entire platensimycin/platencin biosynthetic gene cluster, the sequencing of this roughly 50 kD segment, and the development of an efficient genetic system for the engineering of organisms for the biosynthesis of platensimycin and platencin. The ability to synthesize not only these drugs, but analogs thereof (using combinatorial methods) also is provided. The invention is described in greater detail below.

II. PLATENSIMYCIN AND PLATENCIN

Screening of 250,000 natural product extracts in target-based whole-cell and biochemical assays led to the recovery of a potent and selective small molecule from a strain of *Streptomyces platensis* in a soil sample collected in South Africa. This molecule, called platensimycin ($C_{24}H_{27}NO_7$, molecular mass 441.47), comprises two distinct structural elements connected by an amide bond. Platensimycin shows potent, broad-spectrum Gram-positive activity in vitro and exhibits no cross-resistance to other key antibiotic-resistant bacteria, including methicillin-resistant *S. aureus*, vancomycin-intermediate *S. aureus*, vancomycin-resistant enterococci, and linezolid-resistant and macrolide-resistant pathogens. Platensimycin showed antibacterial activity against efflux-negative *Escherichia coli*, but not against wild-type *E. coli*, indicating that efflux mechanisms limit the effectiveness of platensimycin in *E. coli* and possibly other Gram-negative bacteria. Low mammalian cell toxicity and lack of antifungal activity also suggest that platensimycin acts selectively. Platensimycin showed minimum inhibitory concentration (MIC) values of 0.5 and 1 mg/ml against *S. aureus* and *S. pneumoniae*, respectively.

In whole-cell labeling experiments, platensimycin showed selective inhibition of lipid biosynthesis in *S. aureus* with an $IC_{50}$ of 0.1 µg/ml. Platensimycin did not inhibit DNA, RNA, protein or cell wall biosynthesis at concentrations up to 500 µg/ml. Similar results were obtained with *S. pneumoniae*. Correspondence between MICs and $IC_{50}$ values for the inhibition of cellular lipid biosynthesis indicates that the antibiotic kills bacteria entirely through the inhibition of fatty-acid biosynthesis. Single-enzyme catalytic assays showed that platensimycin is a potent inhibitor of FabF with an $IC_{50}$ of 48 and 160 mM for the *S. aureus* and *E. coli* enzymes, respectively. A weak inhibition of *S. aureus* FabH was observed. It appears that formation of the acyl-enzyme intermediate is essential for platensimycin binding.

Following the report of the discovery of platensimycin, the same group also discovered platencin, another natural product that is chemically- and biologically-related, but different, from platensimycin. Platencin exhibits broad-spectrum Gram-positive antibacterial activity through inhibition of fatty acid biosynthesis, as does platensimycin. It also does not exhibit cross-resistance to key antibiotic resistant strains such as methicillin-resistant *Staphylococcus aureus*, vancomycin-intermediate *S. aureus*, and vancomycin-resistant enterococci. Platencin shows potent in vivo efficacy without any observed toxicity. It targets β-ketoacyl-[acyl carrier protein (ACP)] synthase II (FabF) and III (FabH), as compared to platensimycin that targets only FabF in *S. aureus*.

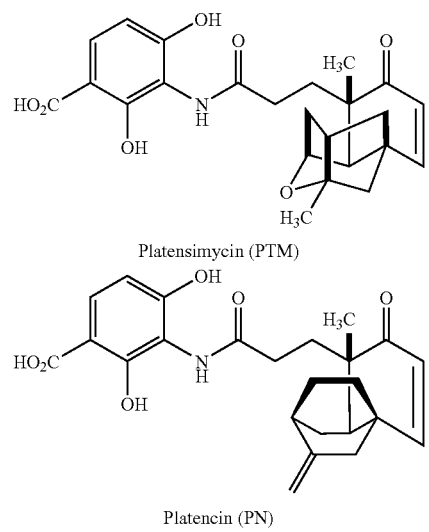

Platensimycin (PTM)

Platencin (PN)

Platencin and platensimycin are both composed of two distinct terpene moieties linked via an amide bond. This may be the first appearance of 3-amino-2,4-dihydroxybenzoic acid in the literature. Significant is the fact that 3,4-aminobenzoic acid has been identified in a number of other natural products. The inventors' amplification of griH represents the first time that enzymes of the pathway described by Suzuki (2006) have been used to identify a gene cluster. The inventors thus envision the same technique (and same primers) might be used to find the gene clusters of manumycin group antibiotics, murayaanthraquinone, and possibly others. The polycyclic moiety of PTM is a $C_{17}$ aliphatic compound that likely comes form terpene biosynthesis (Jayasuriya et al., 2007; Xu et al., 2007; Christianson, 2006). Efforts to elucidate the molecular interactions important to this chemotype's ability to bind FabF have focused on PTM; high resolution structures involving platencin have not yet appeared in the public domain. As revealed in FIGS. 2A-D, both the left and right hand fragments of PTM make significant contacts within the FabF active site (Wang et al., 2006). It also appears that the malonyl-ACP domain binding drugs cerulenin and thiolactomycin overlay very well with PTM; there seem to be some clear analogies to how these three agents bind to and inhibit FabF. Recalling that resistance proteins may share a high degree of structural homology to target proteins, this could be very useful in future efforts to identify resistance proteins, to design new substances with improved activity against native FabF and to produce new agents to which resistant proteins are vulnerable.

A. Cloning and Biosynthesis

Figure 3:
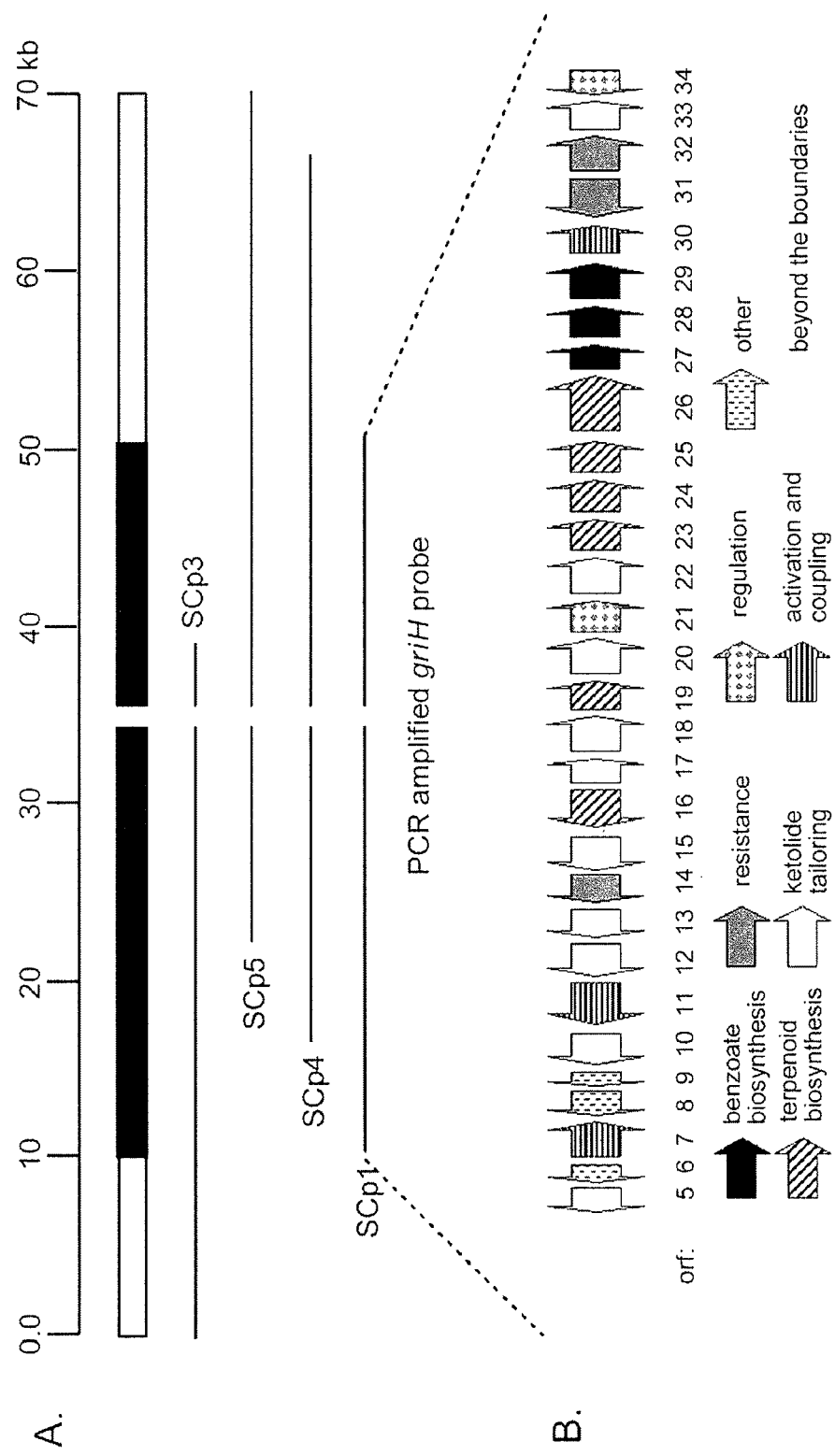
FIGS. 3A-B: Gene cluster cloning.

In certain embodiments of this invention, the platensimycin biosynthetic gene cluster (FIG. 3 and SEQ ID NO:1) will be introduced into a vector or vectors, which in turn is/are introduced into a host cell so as to permit recombinant production of platensimycin and/or platencin. Methods of cloning and expressing large nucleic acids, such as gene clusters, in cells such as Streptomyces are well known to those of skill in the art (Stutzman-Engwall and Hutchinson, 1989; Motamedi and Hutchinson, 1987; Grim et al., 1994; Kao et al., 1994; and Hopwood et al., 1987). In some examples, nucleic acid sequences of well over 100 kb have been introduced into cells, including prokaryotic cells, using vector-based methods (see, for example, Osoegawa et al., 1998; Woon et al., 1998; Huang et al., 1996).

A wide variety of expression vectors and host cells are suitable for the synthesis of platensimycin, platencin or analogs thereof. The choice of vector depends on the sequence(s) that are to be expressed. Any transducible cloning vector can be used as a cloning vector for the nucleic acid constructs of this invention. However, where large clusters are to be expressed, phagemids, cosmids, P1s, YACs, BACs, PACs, HACs or similar cloning vectors can be used for cloning the nucleotide sequences into the host cell. Phagemids, cosmids, and BACs, for example, are advantageous vectors due to the ability to insert and stably propagate therein larger fragments of DNA than in M13 phage and lambda phage, respectively. Phagemids which will find use in this method generally include hybrids between plasmids and filamentous phage cloning vehicles. Cosmids which will find use in this method generally include lambda phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., 1989). The utility of employing such vectors having different marker genes may be exploited to facilitate a determination of successful transduction. In a certain embodiment, Streptomyces vectors are used that include sequences that allow their introduction and maintenance in E. coli. Such Streptomyces/E. coli shuttle vectors have been described (see, for example, Vara et al., 1989; Guilfoile & Hutchinson, 1991).

The gene sequences, or fragments thereof, which collectively encode the platensimycin gene cluster, one or more ORFs, can be inserted into expression vectors, using methods known to those of skill in the art, exemplary methods are described in publications written by Cheng et al., 2002; Tang et al., 2004; and Cheng et al., 2003, which are incorporated herein by reference. Gene sequences which encode the platensimycin gene cluster are provided in SEQ ID NO:1/FIG. 8.

Suitable expression systems for use with the present invention include systems that function in eukaryotic and prokaryotic host cells. However, as explained above, prokaryotic systems are preferred, and in particular, systems compatible with Streptomyces spp. are of particular interest. Control elements for use in such systems include promoters, optionally containing operator sequences, and ribosome binding sites. Exemplary promoters include, but are not limited to bacterial promoters, such as those derived from sugar metabolizing enzymes, such as galactose, lactose (lac) and maltose. Additional examples include promoter sequences derived from biosynthetic enzymes such as tryptophan (trp), the beta-lactamase (bla) promoter system, bacteriophage lambda PL, and T5. In addition, synthetic promoters, such as the tac promoter (U.S. Pat. No. 4,551,433, which is incorporated herein by reference in its entirety), which do not occur in nature also function in bacterial host cells. In Streptomyces, numerous promoters have been described including constitutive promoters, such as ermE and tcmG (Shen and Hutchinson, 1994), as well as controllable promoters such as actI and actIII (Pleper et al., 1995; Pieper et al., 1995; and Wiesmann et al., 1995).

Other regulatory sequences may also be desirable which allow for regulation of expression of the replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, fore example, enhancer sequences.

Selectable markers can also be included in the recombinant expression vectors. A variety of markers are know which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid. Alternatively, several polyketides are naturally colored and this characteristic provides a built-in marker for selecting cells successfully transformed by the present constructs.

Host cells for the recombinant production of platensimycin and platencin, and analogs thereof, can be derived from any organism with the capability of harboring a recombinant 1 nm gene cluster. Thus, the host cells of the present invention can be derived from either prokaryotic or eukaryotic organisms. Particular host cells are those constructed from the actinomycetes, a class of mycelial bacteria that are abundant producers of a number of polyketides and peptides. A particularly useful genus for use with the present system is Streptomyces. Thus, for example, S. verticillus S. ambofaciens, S. avermitilis, S. atroolivaceus, S. azureus, S. cinnamonensis, S. coelicolor, S. curacoi, S. erythraeus, S. fradiae, S. galilaeus, S. glaucescens, S. hygroscopicus, S. lividans, S. parvulus, S. peucetius, S. rimosus, S. roseofulvus, S. thermotolerans, S. violaceoruber, among others, will provide convenient host cells for the subject invention (see, e.g., Hopwood and Sherman, 1990; O'Hagan, 1991), for a description of various polyketide-producing organisms and their natural products).

Other efficient systems for gene expression in either E. coli or Streptomyces species can be used in the present invention. For example, the pET (Novagen, Inc., "pET system Manual" 5th Ed., 1995, Madison, Wis.) or pQE (QIAGEN, Inc. "The QIAexpressionist" 3rd ED., 1997, Santa Clarita, Calif.). The expression efficiency in E. coli for genes from Strepto-

*myces* can be optimized by specific modification at the third positions of the first a few codons of the target gene, taking into account the biased codon usage of streptomycetes (Gramajo et al., 1991). The solubility of the overproduced proteins can be dramatically improved by either co-expression of chaperoning, such as *E. coli* GroEL/S (Wang et al., 1997) or the combination of low incubation temperature (as low as 17° C.), long incubation time (up to 12 hrs after induction), and low or none IPTG induction. The target gene can be expressed either as the native protein or N- or C-terminal fusion proteins. Various pET or pQE vectors for the latter are available that contain different sequences adjacent to the cloning sites. These sequences encode for a variety of peptide "tags" for detection and purification of the target protein. The peptide tags can facilitate isolation of enzymes if difficulty is encountered in the purification of the native proteins. These tags normally do not interfere with the enzyme activities and can be removed if they do become a problem.

B. Purification of Platensimycin, Platencin and Analogs Thereof

Any of a wide variety of chromatographic procedures may be employed to purify anti-infectious compounds according to the present invention. For example, thin layer chromatography, gas chromatography, high performance liquid chromatography, paper chromatography, affinity chromatography or supercritical flow chromatography may be used to effect separation of various chemical species.

Partition chromatography is based on the theory that if two phases are in contact with one another, and if one or both phases constitute a solute, the solute will distribute itself between the two phases. Usually, partition chromatography employs a column, which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatograph are paper chromatograph and thin-layer chromatograph (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography.

Other methods, including crystallization, distillation, and combinations of these with chromatography can be utilized as well.

III. SCREENING TO IDENTIFY ANALOGS OF PLATENSIMYCIN AND PLATENCIN

Although PTM and PN have many attributes that make them good lead compounds for the development of new antibiotics, they lack certain aspects of good drugs. For example, while both compounds display a high degree of in vitro antibacterial activity and very low in vivo toxicities in mouse model studies, they suffer significantly from exceedingly poor pharmacokinetics as evidenced in animal model studies. For PTM, researchers were able to see a $10^4$-$10^5$ fold decrease of S. aureus infection over 24 hrs with no sign of toxicity in a mouse study, however this required a dosage of 100 μg/h delivered intravenously with a continuous pump (Wang et al., 2006). Similarly, PN showed in vivo efficacy in a continuous-infusion (150 μg/h) mouse model of disseminated S. aureus infection with a 3-log reduction of S. aureus cfu in kidney over a 24 h with no evidence of overt toxicity (Wang et al., 2007). Consistent with the in vitro data, infusion of 150 μg/h platencin translated to about the same in vivo effect found with 90 μg/h PTM infusion (Wang et al., 2007). Thus, the inventors will seek improve the pharmacokinetics of this drug class to speed clinical application.

Thus, in a particular embodiment, the present invention provides methods for creating and identifying analogs of platensimycin and platencin. Analog production may rely on natural mutational processes in host bacteria, random but artificial mutational schemes, or site-directed mutational schemes. A particular genetic approach is to produce analogs by introducing tailoring genes from other natural product biosynthetic pathways. Examples of tailoring genes include those that code for enzymes responsible for methylation, acetylation, glycosylation, phosphorylation and related transformations that decorate the basic structural framework of a given molecule (Walsh et al., 2001). Both PTM and PN possess terpene-based skeletons which tailoring enzymes can decorate with various chemical entities.

Alternatively, one may use synthetic chemistry methods to make very specific changes in the structures of PTM or PN, thereby effectively "designing" such new compounds with an eye towards structural attributes that are believed to make them more likely to mimic the positive attributes of PTM and PN, while avoiding their shortcomings. By effect, it is meant that one may assay for effects on lipid formation, or more generally for antibiotic activity.

A. Mutagenesis

Where employed, mutagenesis can be accomplished by a variety of standard, mutagenic procedures. Mutation is the process whereby changes occur in the quantity or structure of an organism. Mutation can involve modification of the nucleotide sequence of a single gene, blocks of genes or whole chromosomes. Changes in single genes may be the consequence of point mutations which involve the removal, addition or substitution of a single nucleotide base within a DNA sequence, or they may be the consequence of changes involving the insertion or deletion of large numbers of nucleotides. The inventors contemplate introduction of mutations into the pathway to provide mutants that produce various biosynthetic intermediates. Isolation of such intermediates may then allow for semi-synthetic modifications to provide new PTM-like agents. One can also envision that feeding such intermediates to other biosynthetic machineries (possibly in organisms other than S. platensis) may provide new "hybrid" natural products.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

i. Random Mutagenesis

Insertional Mutagenesis.

Insertional mutagenesis is based on the inactivation of a gene via insertion of a known DNA fragment. Because it involves the insertion of some type of DNA fragment, the mutations generated are generally loss-of-function, rather than gain-of-function mutations. However, there are several examples of insertions generating gain-of-function mutations (Oppenheimer et al. 1991). Insertion mutagenesis has been very successful in bacteria and Drosophila (Cooley et al. 1988).

Transposable elements in the genome are characterized by being flanked by direct repeats of a short sequence of DNA that has been duplicated during transposition and is called a target site duplication. Virtually all transposable elements whatever their type, and mechanism of transposition, make such duplications at the site of their insertion. In some cases the number of bases duplicated is constant; in other cases it may vary with each transposition event. Most transposable elements have inverted repeat sequences at their termini. These terminal inverted repeats may be anything from a few bases to a few hundred bases long and in many cases they are known to be necessary for transposition.

Prokaryotic transposable elements have been most studied in E. coli and Gram-negative bacteria, but also are present in Gram-positive bacteria. They are generally termed insertion sequences if they are less than about 2 kB long, or transposons if they are longer. Bacteriophages such as mu and D108, which replicate by transposition, make up a third type of transposable element. elements of each type encode at least one polypeptide a transposase, required for their own transposition. Transposons often further include genes coding for function unrelated to transposition, for example, antibiotic resistance genes.

Transposons can be divided into two classes according to their structure. First, compound or composite transposons have copies of an insertion sequence element at each end, usually in an inverted orientation. These transposons require transposases encoded by one of their terminal IS elements. The second class of transposon have terminal repeats of about 30 base pairs and do not contain sequences from IS elements.

Transposition usually is either conservative or replicative, although in some cases it can be both. In replicative transposition, one copy of the transposing element remains at the donor site, and another is inserted at the target site. In conservative transposition, the transposing element is excised from one site and inserted at another.

Transposable elements are an important source of spontaneous mutations, and have influenced the ways in which genes and genomes have evolved. They can inactivate genes by inserting within them, and can cause gross chromosomal rearrangements either directly, through the activity of their transposases, or indirectly, as a result of recombination between copies of an element scattered around the genome. Transposable elements that excise often do so imprecisely and may produce alleles coding for altered gene products if the number of bases added or deleted is a multiple of three.

Transposable elements themselves may evolve in unusual ways. If they were inherited like other DNA sequences, then copies of an element in one species would be more like copies in closely related species than copies in more distant species. This is not always the case, suggesting that transposable elements are occasionally transmitted horizontally from one species to another.

Chemical Mutagenesis.

Chemical mutagenesis offers certain advantages, such as the ability to find a full range of mutant alleles with degrees of phenotypic severity, and is facile and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the O4 position of thymine induced by exposure to n-nitrosoureas results in TA to CG transitions.

A high correlation between mutagenicity and carcinogenity is the underlying assumption behind the Ames test (McCann et al., 1975) which speedily assays for mutants in a bacterial system, together with an added rat liver homogenate, which contains the microsomal cytochrome P450, to provide the metabolic activation of the mutagens where needed.

In vertebrates, several carcinogens have been found to produce mutation in the ras proto-oncogene. N-nitroso-N-methyl urea induces mammary, prostate and other carcinomas in rats with the majority of the tumors showing a G to A transition at the second position in codon 12 of the Ha-ras oncogene. Benzo[a]pyrene-induced skin tumors contain A to T transformation in the second codon of the Ha-ras gene.

Radiation Mutagenesis.

The integrity of biological molecules is degraded by the ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Ionizing radiation causes DNA damage and cell killing, generally proportional to the dose rate. Ionizing radiation has been postulated to induce multiple biological effects by direct interaction with DNA, or through the formation of free radical species leading to DNA damage (Hall, 1988). These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman et al., 1989). Synthesis of cyclin and co-regulated polypeptides is suppressed by ionizing radiation in rat REF52 cells, but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte, et al., 1989).

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an x-radiation. The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art.

In a certain embodiments, an effective expression inducing amount is from about 2 to about 30 Gray (Gy) administered at a rate of from about 0.5 to about 2 Gy/minute. Even more preferably, an effective expression inducing amount of ionizing radiation is from about 5 to about 15 Gy. In other embodiments, doses of 2-9 Gy are used in single doses. An effective dose of ionizing radiation may be from 10 to 100 Gy, with 15 to 75 Gy being preferred, and 20 to 50 Gy being more preferred.

Any suitable means for delivering radiation to a tissue may be employed in the present invention in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

In Vitro Scanning Mutagenesis.

Random mutagenesis also may be introduced using error prone PCR (Cadwell and Joyce, 1992). The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In recent years, techniques for estimating the equilibrium constant for ligand binding using minuscule amounts of protein have been developed (Blackburn et al., 1991; U.S. Pat. Nos. 5,221,605 and 5,238,808). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

Random Mutagenesis by Fragmentation and Reassembly.

A method for generating libraries of displayed polypeptides is described in U.S. Pat. No. 5,380,721. The method comprises obtaining polynucleotide library members, pooling and fragmenting the polynucleotides, and reforming fragments therefrom, performing PCR amplification, thereby homologously recombining the fragments to form a shuffled pool of recombined polynucleotides.

ii. Site-Directed Mutagenesis

Structure-guided site-specific mutagenesis represents a powerful tool for the dissection and engineering of protein-ligand interactions (Wells, 1996, Braisted et al., 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as E. coli polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as E. coli cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996; Zeng et al., 1996; Burton and Barbas, 1994; Yelton et al., 1995; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

B. Screens for Activity

To identify a platensimycin/platencin analog, one generally will determine the anti-bacterial activity in the presence and absence of a test substance, wherein an analog is identified by its structural relation to PTM and/or PN and its ability to alter bacterial growth or lipid synthesis in a manner similar to platensimycin and platencin. For example, a method may generally comprise:

(a) providing a bacterial cell that is susceptible to platensimycin and platencin;

(b) contacting said cell with said test substance; and (c) assessing the toxicity of the test substance on the cell, wherein toxicity to the cell in the presence of the test substance, as compared to that observed in the absence of the test substance, indicates that the test substance is an anti-bacterial agent and a PTM/PN analog. Still further, in certain embodiments, the screening method may comprise assessing the toxicity of the test substance on a cell that is not susceptible to platensimycin or platencin, i.e., a eukaryotic cell, a mammalian cell, a fungal cell, etc., to determine non-specific toxicity.

Assays may be conducted in isolated cells, or in organisms including animals. It will, of course, be understood that all the screening methods of the present invention are useful in themselves notwithstanding the fact that effective candidates may not be found. These assays may be performed at a lab bench by a human operator, via mechanized high through-put screening, or any other manner known in the art. The candidate substance(s) tested may be an individual candidate or one or more of a library of candidates and may be obtained from any source and in any manner known to those of skill in the art.

As used herein the term "candidate substance" or "candidate compound" refers to any compound that is structurally-related to platensimycin or platencin. Such compounds may be identified by rational drug design, which produces structural analogs of biologically active compounds. By creating such analogs, it is possible to fashion drugs which are more active or stable than the natural molecules, which have different susceptibility to alteration or which may affect the function of various other molecules. In one approach, one would generate a three-dimensional structure for platensimycin/platencin or a portion thereof. This could be accomplished by x-ray crystallography, computer modeling or by a combination of both approaches. An alternative approach, involves the random replacement of functional groups throughout platensimycin/platencin, and the resulting effect determined.

IV. METHODS OF TREATMENT

In a particular aspect, the present invention provides methods for the treatment of an infectious disease. Treatment methods will involve administering to an individual having or at risk of a bacterial infection an effective amount of a composition containing PTM, PN or an analog thereof. An effective amount is described, generally, as that amount sufficient to detectably and repeatedly to ameliorate, reduce, minimize or limit the extent of the infection or its symptoms. More specifically, it is envisioned that the treatment with platensimycin and/or platencin or analogs thereof will kill bacteria, inhibit their growth, and/or otherwise reverse or reduce the symptoms of the infection.

A. Bacterial Targets

*Staphylococcus.*

Within the family Micrococcaceae, the human pathogenic genus *Staphylococcus* can be separated from the non-pathogenic genus *Micrococcus* by various tests, including (1) anaerobic acid production from glucose, (2) sensitivity to 200 µg/ml lysostaphin or to 100 µg furazolidone, and (3) production of acid from glycerol in the presence of 0.4 µg/ml erythromycin, all these tests being positive in the case of staphylococci. Further subclassification into the three main species is of considerable clinical importance (i.e., *S. aureus, Staphylococcus epidermidis*, and *Staphylococcus saprophyticus*).

Once the *Staphylococcus* has been differentiated as *Staphylococcus aureus*, it is necessary to determine if the *S. aureus* is methicillin resistant. Older methods such as resistance phenotype, bacteriophage typing, immunoserology, and serotyping of coagulase can be used to type *S. aureus*. More recently, these methods have been replaced by electrophoretic protein typing, multilocus enzyme electrophoresis, and various genetic techniques, including plasmid analysis, restriction endonuclease analysis of chromosomal DNA, restriction fragment length polymorphisms, ribotyping, nucleotide sequence analysis, and many others.

*Bacillus.*

*Bacillus* species are rod-shaped, endospore-forming aerobic or facultatively anaerobic, Gram-positive bacteria; in some species cultures may turn Gram-negative with age. The many species of the genus exhibit a wide range of physiologic abilities that allow them to live in every natural environment. Only one endospore is formed per cell. The spores are resistant to heat, cold, radiation, desiccation, and disinfectants. *Bacillus anthracis* needs oxygen to sporulate; this constraint has important consequences for epidemiology and control. In vivo, *B. anthracis* produces a polypeptide (polyglutamic acid) capsule that protects it from phagocytosis. The genera *Bacillus* and *Clostridium* constitute the family Bacillaceae. Species are identified by using morphologic and biochemical criteria.

The virulence factors of *B. anthracis* are its capsule and three-component toxin, both encoded on plasmids. *B. cereus* produces numerous enzymes and aggressins. The principal virulence factors are a necrotizing enterotoxin and a potent hemolysin (cereolysin). Emetic food poisoning probably results from the release of emetic factors from specific foods by bacterial enzymes.

*Mycobacterium.*

Both leprosy and tuberculosis, caused by *Mycobacterium leprae* and *Mycobacterium tuberculosis* respectively, have plagued mankind for centuries. With the emergence of antibiotic resistant strains of tuberculosis, research into *Mycobacteria* has become all the more important in combating these modern mutants of ancient pathogens.

Both the genomes of *Mycobacterium tuberculosis* and *Mycobacterium leprae* have been sequenced with hopes of gaining further understanding of how to defeat the infamously successful pathogens. The genome of *M. tuberculosis* is 4,411,522 base pairs long with 3,924 predicted protein-coding sequences, and a relatively high G+C content of 65.6%. At 4.4 Mbp, *M. tuberculosis* is one of the largest known bacterial genomes, coming in just short of *E. coli*, and a distant third to *Streptomyces coelicolor*.

The genome of *Mycobacterium leprae* is 3,268,203 base pairs long, with only 1,604 predicted protein-coding regions, and a G+C content of about 57.8%. Only 49.5% of the *M. leprae* genome contains open reading frames (protein-coding regions), the rest of the genome is comprised of pseudogenes, which are inactive reading frames with recognizable and functional counterparts in *M. tuberculosis* (27%), and regions that do not appear to be coding at all, and may be gene remnants mutated beyond recognition (23.5%). Of the genome of *M. tuberculosis*, 90.8% of the genome contains protein-coding sequences with only 6 pseudogenes, compared to the 1,116 pseudogenes on the *M. leprae* genome.

*Pseudomonas.*

The genus *Pseudomonas* is characterized by Gram-negative rods that utilize glucose oxidatively. Members are classified into five groups based on ribosomal RNA homology. These bacteria are resistant to most antibiotics and are capable of surviving in very harsh conditions tolerated by very few other organisms. They also are known to produce a coating that helps protect the bacterium from outside agents. *Pseudomonas* is often found in hospitals and clinics and, not surprisingly, is a major cause of nosocomal infections. It often targets immunocompromised individuals, such as burn victims and individuals on respirators or with indwelling catheters. Infection sites are varied and include the urinary tract, blood, lungs, and pharynx. However, because it is non-invasive, it tends not to be found in healthy individuals.

*Pseudomonas aeruginosa* is the most common member of its genus, distinguished from other species of *Pseudomonas* by its ability to grow at 42° C., produce bluish (pyocyanin) and greenish pigments, and exhibit a characteristic fruity odor. The pathogenicity involves several toxins and chemicals that the bacterium secretes upon infection. The presence of a lipopolysaccharide layer serves to protect the organism as well as aid in cell adherence to host tissues. Lipases and exotoxins secreted by the organism then proceed to destroy host cell tissue, leading to complications often associated with infection. *P. aeruginosa* prefers moist environments, and will grow on almost any laboratory medium. *Pseudomonas* infections are usually treated with a combination of antibiotics, e.g., an anti-pseudomonal penicillin and an aminoglycoside.

Other Bacteria.

In addition to the bacteria discussed above, the inventors also contemplate treating other bacteria. Such bacteria include *Escherichia coli, Streptococcus pneumoniae, Streptococcus pyogenes, Streptococcus agalactiae, Streptococcus viridans, Enterococcus faecalis, Enterococcus faecium, Clostridium botulinum, Clostridium perfringens, Clostridium tetani, Clostridium difficile, Listeria monocytogenes, Legionella pneumophila, Francisella tularensis, Pasteurella multocida, Brucella abortive, Brucella suis, Brucella melitensis, Bordetella pertussis, Salmonella* sp., *Shigella* sp., *Eschericia coli, Vibrio* sp., *Klebsiella* sp., *Aeromonas* sp., *Plesiomonas* sp., *Rickettsiae* sp., *Chlamydiae* sp., *Ehrlichia* sp., *Mycoplasma* sp., *Helicobacter* sp., *Campylobacter* sp., and *Haemophilus* sp.

B. Dosages

In certain embodiments, the platensimycin, platencin or analog thereof is administered to a subject. An effective amount of platensimycin or platencin that may be administered to a cell includes a dose of about −0.1 µM to about 100 µM. More specifically, doses of platensimycin or platencin to be administered are from about 0.1 µM to about 1 µM; about 1 µM to about 5 µM; about 5 µM to about 10 µM; about 10 µM to about 15 µM; about 15 µM to about 20 µM; about 20 µM to about 30 µM; about 30 µM to about 40 µM; about 40 µM to about 50 µM; about 50 µM to about 60 µM; about 60 µM to about 70 µM; about 70 µM to about 80 µM; about 80 µM to about 90 µM; and about 90 µM to about 100 µM. Of course, all of these amounts are exemplary, and any amount in-between these points is also expected to be of use in the invention.

In another embodiment of the invention, the dose range of the platensimycin, platencin or analogs thereof will be measured by body weight, for example, about 0.5 mg/kg body weight to about 500 mg/kg body weight. Those of skill will recognize the utility of a variety of dosage range, for example, 1 mg/kg body weight to 450 mg/kg body weight, 2 mg/kg body weight to 400 mg/kg body weighty, 3 mg/kg body weight to 350 mg/kg body weighty, 4 mg/kg body weight to 300 mg/kg body weight, 5 mg/kg body weight to 250 mg/kg body weighty, 6 mg/kg body weight to 200 mg/kg body weight, 7 mg/kg body weight to 150 mg/kg body weighty, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for platensimycin, platencin or analogs thereof.

The treatments may include various "unit doses." Unit dose is defined as containing a predetermined-quantity of the therapeutic composition (platensimycin, platencin or its analogs thereof) calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

As is well known in the art, a specific dose level of active compounds such as platensimycin, platencin or analogs thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

C. Formulations and Routes for Administration

Pharmaceutical compositions of the present invention comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

D. Combined Therapy

In the context of the present invention, it is contemplated that the platensimycin, platencin or analogs thereof may be used in combination with an additional antibacterial agent to more effectively treat infections.

When an additional therapeutic agent is administered, as long as the dose of the additional therapeutic agent does not exceed previously quoted toxicity levels, the effective amounts of the additional therapeutic agent may simply be defined as that amount effective to inhibit the growth or kill the bacteria when administered to an animal in combination with the platensimycin, platencin or analog thereof. This may be easily determined by monitoring the animal or patient and measuring those physical and biochemical parameters of health and disease that are indicative of the success of a given treatment. Such methods are routine in animal testing and clinical practice.

To kill or slow the growth of bacteria using the methods and compositions of the present invention, one can contact the bacteria with platensimycin, platencin or analog thereof in combination with an additional therapeutic agent. These compositions would be provided in a combined amount effective to inhibit bacterial cell growth and kill the bacterium. This process may involve contacting the cells with platensimycin, platencin or analog thereof in combination with an additional therapeutic agent or factor(s) at the same time. This may be achieved by contacting the cell with a single composition or pharmacological formulation that includes both agents, or by contacting the cell with two distinct compositions or formulations, at the same time, wherein one composition includes platensimycin, platencin or analog thereof and the other includes the additional agent.

Alternatively, treatment with platensimycin, platencin or analog thereof may precede or follow the additional agent treatment by intervals ranging from minutes to weeks. In embodiments where the additional agent is administered separately to the patient, one would generally ensure that a significant period of time did not expire between the time of each delivery, such that the agent would still be able to exert an advantageously combined effect on the cell. In such instances, it is contemplated that one would contact the cell with both modalities within about 12-24 hr of each other and, more preferably, within about 6-12 hr of each other, with a delay time of only about 12 hr being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either platensimycin, platencin or analog thereof in combination with an additional therapeutic agent such as anticancer agent will be desired. Various combinations may be employed, where platensimycin, platencin or analog thereof is "A" and the additional antibiotic agent is "B", as exemplified below:

A/B/A B/A/B B/B/A A/A/B B/A/A A/B/B B/B/B/A
B/B/A/B

A/A/B/B A/B/A/B A/B/B/A B/B/A/A B/A/B/A B/A/A/B
B/B/B/A

A/A/A/B B/A/A/A A/B/A/A A/A/B/A A/B/B/B B/A/B/B
B/B/A/B

Classes of antibiotics that may be used in conjunction with compounds of the present invention include, but are not limited to, macrolides (e.g., erythromycin), penicillins (e.g., nafcillin), cephalosporins (e.g., cefazolin), carbepenems (e.g., imipenem, aztreonam), other beta-lactam antibiotics, beta-lactam inhibitors (e.g., sulbactam), oxalines (e.g., linezolid), ATP synthase inhibitors (e.g. diarylquinoline compounds, R207910), aminoglycosides (e.g., gentamicin), chloramphenicol, sulfonamides (e.g., sulfamethoxazole), glycopeptides (e.g., vancomycin), quinolones (e.g., ciprofloxacin), tetracyclines (e.g., minocycline), fusidic acid, trimethoprim, metronidazole, clindamycin, mupirocin, polyenes (e.g., amphotericin B), rifamycins (e.g., rifampin), and azoles (e.g., fluconazole).

Examples of specific antibiotics that may be used include, but are not limited to, nafcillin, methicillin, oxacillin, cloxacillin, dicloxacillin, ampicillin, amoxicillin, carbenicillin, ticarcillin, mezlocillin, piperacillin, erythromycin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, levofloxacin, grepafloxacin, norfloxacin, nalidixic acid, sparfloxacin, pefloxacin, amifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, R207910 and nystatin.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Production of Platensimycin and Platencin by *S. Platensis* MA7327 and MA7339

Two *S. platensis* strains—MA7327 the original PTM producer (Wang et al., 2006; Singh et al., 2006) and MA7339 the original PTN producer (Wang et al., 2007; Jayasuriya et al., 2007)—were provided by Merck. PTM and PTN productions from these strains under the reported conditions have been re-established in the inventors' lab with comparable yields (i.e., ~1-4 mg/L for PTM and ~1 mg/L for PTN) (Wang et al., 2006; Singh et al., 2006; Wang et al., 2007; Jayasuriya et al., 2007). An HPLC method for PTM and PTN analysis has also been developed. Recognizing the biosynthetic parallel between PTM and PTN (see FIGS. 5A-D), the inventors were interested in examining if the PTM producer could produce PTN or vice versa by varying the fermentation conditions. Remarkably, while the MA7339 strain produces PTN exclusively under all conditions tested, the MA7327 strain produces PTM exclusively in the PTM medium as reported (Wang et al., 2006; Singh et al., 2006), but produces both PTM and PTN in almost 1:1 ratio in the PTN medium reported for the MA7339 strain (Pearson, 2006; Barton, 2006). On the basis of these observations, the inventors now propose that MA7339 is an exclusive PTN producer but MA7327 is a PTM and PTN dual producer. They further propose that the difference in metabolite profiles between the two strains result from the specificity and promiscuity of their respective ent-kaurene synthases (FIGS. 6A-D). The ent-kaurene synthases in the two strains represent a rare occasion of evolution caught in action. Comparative characterization of the ent-kaurene synthases from the two strains therefore provides an excellent opportunity to investigate how terpenoid cyclases are evolved to dictate specific product outcome.

Biosynthetic Origin of PTM by Feeding Experiments with Isotope-Labeled Precursors in *S. platensis* MA7327.

Inspection of the structures of PTM and PTN has led to the proposal that the 3-amino-2,4-dihydroxybenzoate moiety is most likely derived a C4 unit from Krebs cycle and a C3 unit from glycolysis via 3,4-AHBA as a key intermediate (Gould et al., 1996; Hu and Floss, 2004; Petricek et al., 2006; Suzuki et al., 2006), while the ketolide moieties are of diterpene origin via ent-copalyl diphosphate (ent-CPP) as a key intermediate, diverging from which into PTM and PTN results from product promiscuity of the ent-kaurene synthases (Davis and Croteau, 2000; Hanson, 2005; Kuzuyama and Seto, 2003; Dairi, 2005; Christianson, 2006; Tudzynski, 2005; Toyomasu et al., 2007; Xu et al., 2007a; Xu et al., 2007b; Mohan et al., 1996; Xu et al., 2004; Wilderman et al., 2004; Prisic et al., 2004; Hayashi et al., 2006; Xu et al., 2007c; Roy et al., 2007; Prisic et al., 2007). This has been now supported by results from feeding experiments with isotope-labeled precursors in *S. platensis* MA7327. A battery of precursors, including [1-$^{13}$C]-, [2-$^{13}$C]-, [1,2-$^{13}$C$_2$]acetate, [2-$^{13}$C]-, [3-$^{13}$C]-, [2,3-$^{13}$C$_2$]pyruvate, and [2-$^{13}$C]glycerol, were efficiently and specifically incorporated into PTM. The resultant labeling patterns unambiguously established the biosynthetic origin of PTM (Herath et al., 2007). Close examination of the labeling patterns of the ketolide moiety of PTM from $^{13}$C-labeled pyruvate and glycerol also revealed that IPP and DMAPP for PTM are biosynthesized via the MEP pathway in *S. platensis* MA7327.

Strategies to Clone the PTM/PTN Biosynthetic Gene Cluster from *S. platensis* MA7327.

There are few general strategies available to clone terpenoid biosynthetic gene clusters from actinomycetes or other organisms (Davis and Croteau; 2000; Kuzuyama and Seto, 2003; Dairi, 2005). Recognizing that the biosynthesis of the 3-amino-2,4-dihydroxybenzoate moiety of PTM is unique, invoking a novel pathway, the inventors decided to develop a PCR strategy to clone genes encoding enzymes that catalyze key steps of this pathway. Since the function of GriH in catalyzing the formation of 3-amino-4-hydroxybenzoic acid from the metabolites of Kreb cycle and glycolysis was firmly established in grixazone biosynthesis (Suzuki et al., 2006), the inventors reasoned that grih could serve as a specific probe for this pathway. Blast search of GriH (accession no. BAF36650) against the public protein database resulted in a few homologs, but none of them with an established function, a finding that is consistent with the functional assignment of GriH as an unprecedented 3-amino-4-hydroxybenzoic acid synthase. However, the inventors were interested in two homologs from the *Frankia* sp CcI3 genome, Francci3_4026 (accession no. YP_483283 annotated as a DHNA-like aldolase) and Francci3_2069 (accession no. YP_48117 annotated as a hypothetic protein), which showed high sequence homology to GriH. They selected two conserved regions (TKIPLEI and PINEFC) of GriH to design degenerate primers, taking into consideration of the high GC codon bias of actinomycetes, and developed a PCR strategy to clone a gene for this specific step, thereby accessing the 3-amino-4-hydroxybenzoic acid biosynthetic pathway. A distinct product with the expected size of 750 bp was readily amplified from *S. platensis* MA7327. DNA sequencing of a random pool of the PCR products yielded a single product, the deduced gene product of which showed 83% identity/89% similarity to GriH. These findings demonstrated the high specificity of the PCR primers and the effectiveness of this strategy in cloning an essential gene encoding 3-amino-4-hydroxybenzoic acid biosynthesis. This strategy therefore should be applicable to clone biosynthetic gene clusters of other 3-amino-4-hydroxybenzoate-derived natural products.

Using the PCR amplified grih homolog as a probe, the inventors localized a 70-kb DNA region, covered by four overlapping cosmids, from *S. platensis* MA7327 that harbors the PTM/PTN biosynthetic gene cluster (FIG. 3A) (Manallack et al., 2008). They have sequenced 40-kb of this locus, revealing 36 open reading frames (ORFs) (FIG. 3B). Pending experimental confirmation, the boundaries of the PTM/PTN gene cluster have been assigned to be at ORF7 (upstream) and ORF35 (downstream), respectively, on the basis of bioinformatics analysis. Among the genes within the PTM/PTN cluster are: (i) three ORFs (orf27, orf28, orf29) encoding 3-amino-2,4-dihydroxybenzoic acid biosynthesis, (ii) three ORFs (orf24, orf25, orf26) encoding IPP and DMAPP biosynthesis by the MEP pathway and three ORFs (orf16, orf19, orf23) encoding ent-kaurene and ent-atiserene biosynthesis from the isoprene precursors en route to the ketolide moieties of PTM and PTN, (iii) six ORFs (orf15, orf17, orf18, orf20, orf22, orf33) encoding the conversion of nascent diterpene intermediates into the ultimate ketolide structures found in PTM and PTN, (iv) two ORFs (orf11, orf30) encoding activation and final coupling of the aminobenzoate and ketolide moieties into PTM and PTM, (v) three ORFs (orf9, orf21, orf34) encoding pathway-specific regulators, (vi) three ORFs (orf14, orf31, orf32) encoding resistance, and (vii) four additional ORFs (orf8, orf10, orf12, orf13) encoding other enzyme functions whose role in PTM and PTN biosynthesis cannot be assigned on the basis of bioinformatics (Table 1).

TABLE 1

Deduced functions of ORFs in the PTM/PTN biosynthetic gene cluster from *S. platensis* MA7327

| Gene | No. Amino Acids | Protein homolog | Homology (% identity/% similarity) | Proposed function |
|---|---|---|---|---|
| orf1-orf5 | | | | ORFs beyond the upstream boundary |
| orf6 | 254 | DitI (AAD21071) | 40/53 | Short chain dehydrogenase |
| orf7 | 434 | PaaK (P76085) | 29/45 | Ligase |
| orf8 | 263 | RHA1_ro10300 (YP_708647) | 33/47 | Unknown |
| orf9 | 141 | FRAAL2637 (CAJ61283) | 53/69 | Regulatory (DNA binding protein) |
| orf10 | 386 | PhlC (AAB48108) | 25/41 | Unknown |
| orf11 | 486 | Fcs (CAC18323) | 33/44 | Long-chain fatty acid CoA ligase |
| orf12 | 356 | BarH (AAN32982) | 32/48 | Hydrolase |
| orf13 | 286 | UfaA2 (NP_827047) | 55/69 | Dehydratase |
| orf14 | 311 | Neut_1128 (YP_747348) | 26/42 | Prenyltransferase (active sites mutated) |

TABLE 1-continued

Deduced functions of ORFs in the PTM/PTN biosynthetic gene cluster from S. platensis MA7327

| Gene | No. Amino Acids | Protein homolog | Homology (% identity/% similarity) | Proposed function |
|---|---|---|---|---|
| orf15 | 440 | HctG (AAY42339) | 30/50 | P-450 oxygenase |
| orf16 | 533 | ent-Cdps (BAD86797) | 45/58 | ent-Copalyl synthase |
| orf17 | 285 | SAML0622 (CAJ89608) | 32/44 | Dioxygenase |
| orf18 | 380 | Orf34 (ABO15870) | 49/67 | Long-chain acyl CoA dehydrogenase |
| orf19 | 309 | KSB (Q39548) | 25/48 | ent-Kaurene synthase |
| orf20 | 430 | Cyp230 (AAT45303) | 53/65 | P-450 oxygenase |
| orf21 | 355 | MVA_2666 (YP_881857) | 33/45 | Regulatory (hypothetic kinase) |
| orf22 | 389 | TblC (AAO63153) | 27/43 | Dioxygenase |
| orf23 | 348 | Ggdps (BDA07816) | 66/77 | Geranylgeranyl diphosphate synthase |
| orf24 | 363 | LytB (AAC78334) | 51/66 | HMBDP reductase (MEP pathway) |
| orf25 | 385 | PlaT5 (ABB69755) | 85/92 | HMBDP synthase (MEP pathway) |
| orf26 | 587 | PlaT6 (ABB69756) | 62/71 | DXP synthase (MEP pathway) |
| orf27 | 277 | GriI (BAF36651) | 64/78 | DHNA-like aldolase |
| orf28 | 368 | GriH (BAF36650) | 76/87 | 3-amino-4-hydroxybenzoic acid synthase |
| orf29 | 396 | MhbM (AAW63416) | 32/49 | Flavin-dependent benzoate hydroxylase |
| orf30 | 291 | TubG (CAF05656) | 34/44 | Amide synthase (N-acetyl transferase) |
| orf31 | 474 | PhlA (AAY86548) | 28/41 | β-Ketoacyl-ACP synthase |
| orf32 | 414 | AcaB (CAA59498) | 34/51 | Acetyl CoA acetyltransferase |
| orf33 | 301 | ORF27 (BAD66689) | 47/62 | Oxidoreductase |
| orf34 | 238 | Francci3_2979 (ABD12336) | 50/61 | Transcriptional repressor |
| orf35-orf36 | | | | ORFs beyond the downstream boundary |

Development of a Genetic System for S. platensis MA7237 and Confirmation of the Cloned Locus Encoding PTM and PTN Biosynthesis.

The inventors have developed an efficient genetic system for in vivo manipulation of PTM/PTN biosynthesis in S. platensis MA7327 via E. coli-S. platensis conjugation. S. platensis MA7327 grows optimally between 28° C. and 30° C., is highly sensitive to apramycin (Apr), erythromycin (Em), kanamycin (Kan), and thiostrepton (Thi) with complete inhibition of growth at 25 μg/mL, 10 μg/mL, 25 μg/mL, and 10 μg/mL, respectively, and is resistant to trimethoprim and nalidixic acid with no growth inhibition observed at 100 μg/mL. Although S. platensis protoplasts can be readily prepared and regenerated with high frequency, introduction of either replicative or integrative plasmid into S. platensis via protoplast-mediated transformation has not been successful (Kieser et al., 2000). Conjugation between E. coli ET12567 (pUZ8002) (Kieser et al., 2000) and S. platensis MA7237 occurred with high frequency on modified ISP-4 agar freshly supplemented with 10 mM MgCl$_2$ (Liu and Shen, 2000). The exconjugant frequencies for interactive plasmids such as pSET152 (Bierman et al., 1992) were approximately $10^{-4}$ to $10^{-5}$. Taking advantage of homologous recombination to introduce gene replacement mutations into S. platensis chromosome, the inventors have also demonstrated the overall frequencies of exconjugation and homologous recombination for nonreplicating plasmids such as pOJ260 with S. platensis MA7327 insert were on the order of $10^{-7}$ to $10^{-8}$.

Figure 4:
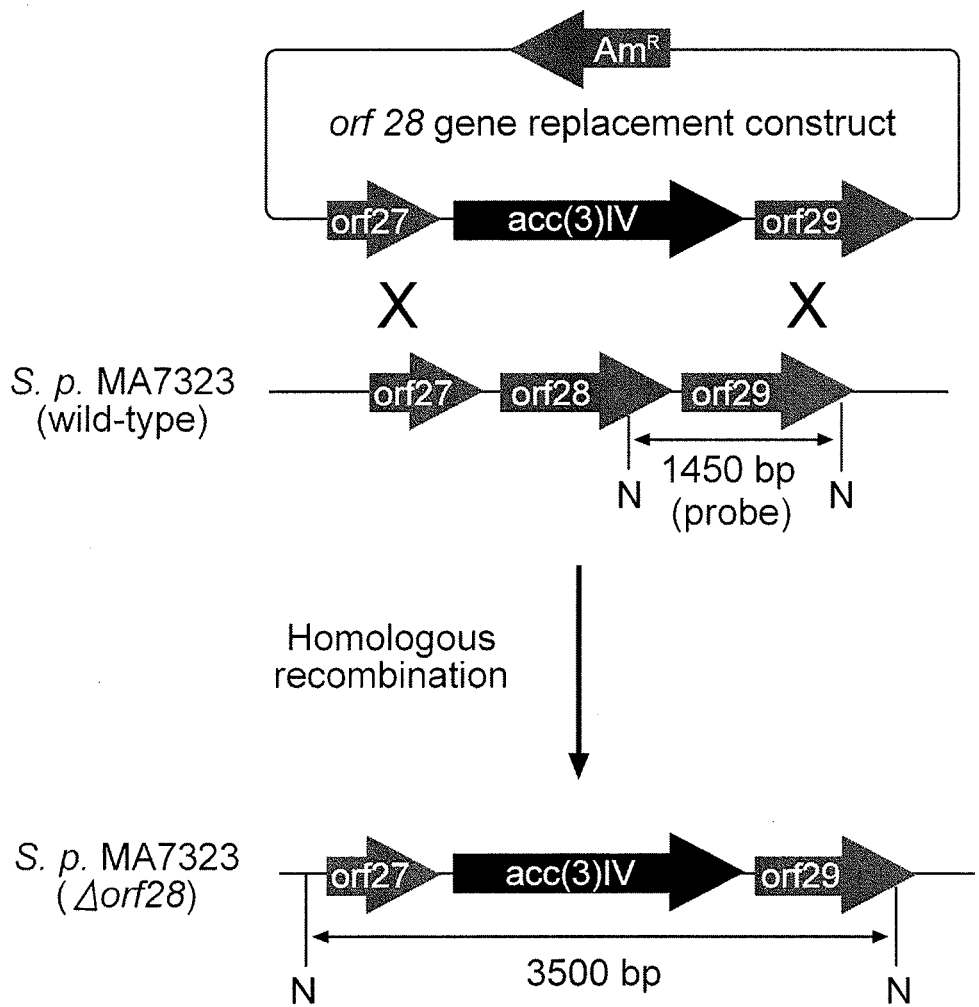
FIGS. 4A-D (9): Inactivation of orf28 in *S. platensis* MA7327 by gene replacement and characterization of the resultant Δorf18 mutant strain.
Figure 4:
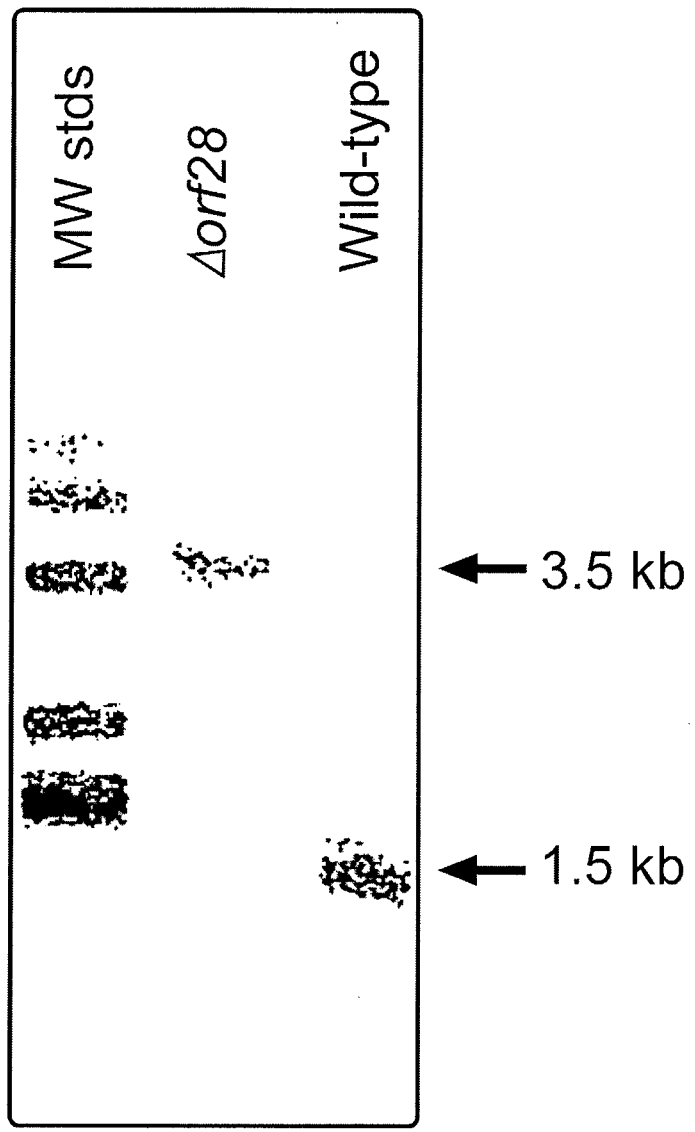
Figure 4:
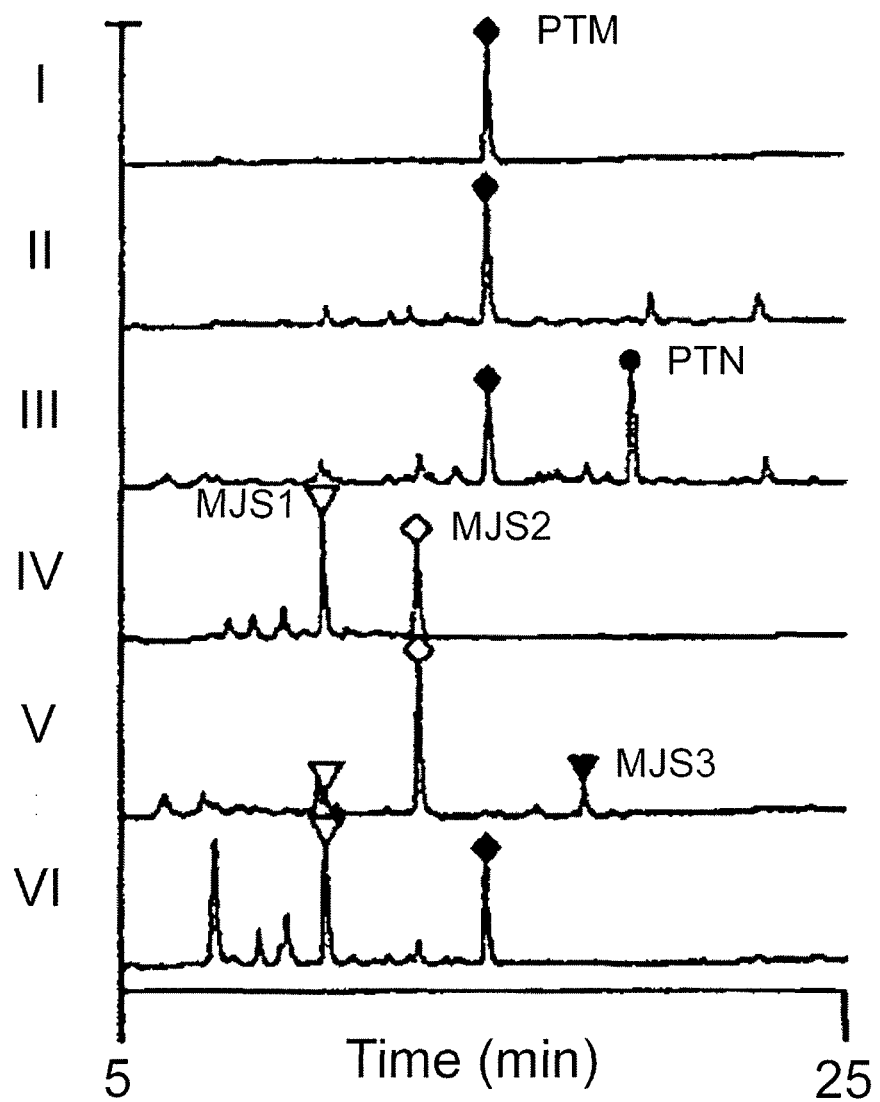

To demonstrate the feasibility of manipulating PTM biosynthesis in S. platensis MA7327 in vivo using the established conjugation protocol, the inventors inactivated the orf28 by a gene replacement strategy as depicted in FIGS. 4A-D. To inactivate orf28, it was first replaced by an aac(3)IV resistance cassette (Apr$^R$) via gene replacement by the REDIRECT method (Gust et al., 2003). The Δorf28::aac(3)IV mutant was then isolated in S. platensis MA7327 by allelic exchange via homologous recombination, selected for the Amp$^S$ and Apr$^R$ phenotype (FIG. 4A). The genotype of the mutant strain was confirmed by Southern analysis. While the wild-type strain showed a distinct band at 1.5 kb, this fragment was shifted to 3.5 kb in the mutant strain (FIG. 4B), as would be expected when replacing orf28 with the Δorf28:: aac(3)IV allele by a double-crossover homologous recombination event (FIG. 4A). The Δorf28 mutant strain was fermentated under conditions optimized for PTM and PTN production. Since orf28 encodes the 3-amino-4-hydroxybenzoate synthase, an essential enzyme for the biosynthesis of the 3-amino-2,4-dihydroxybenzoate moiety of PTM and PTN, the inventors predicted that inactivation of orf28 should completely abolish PTM and PTN production. HPLC analysis of the fermentations of Δorf28 mutant indeed showed complete abolishment of (i) PTM under the conditions optimized for PTM production and (ii) both PTM and PTN under the conditions optimized for PTM and PTN production, respectively (FIG. 4C).

Figure 5:
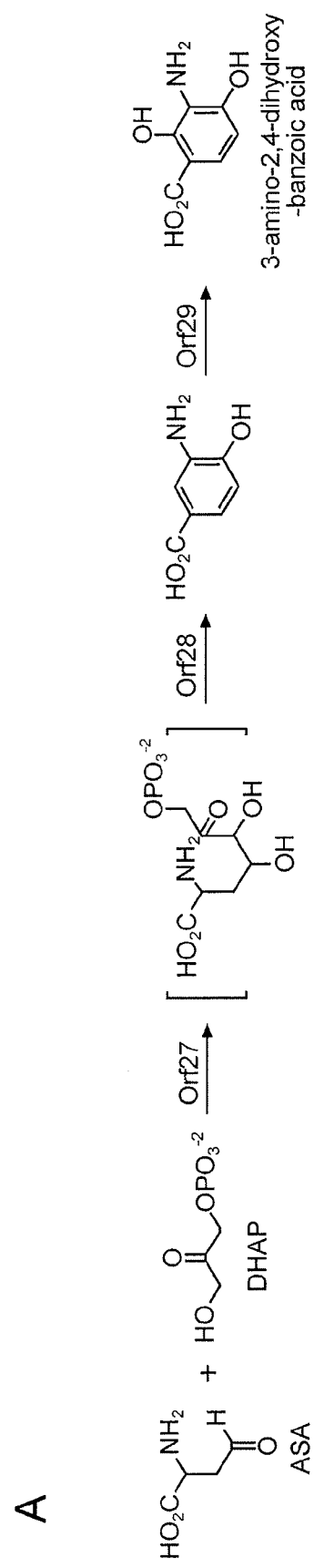
FIGS. 5A-D (10): A proposed pathway for PTM and PTN biosynthesis in *S. platensis* MA7237.
Figure 5:
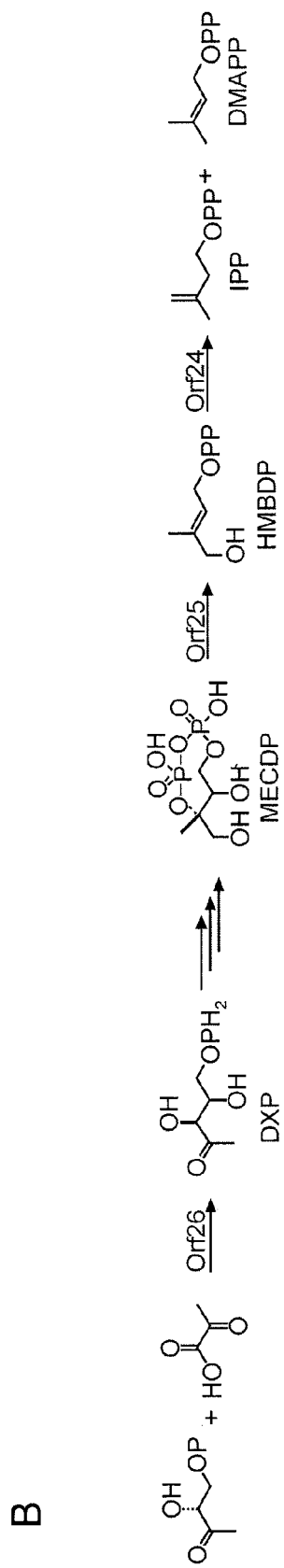
Figure 5:
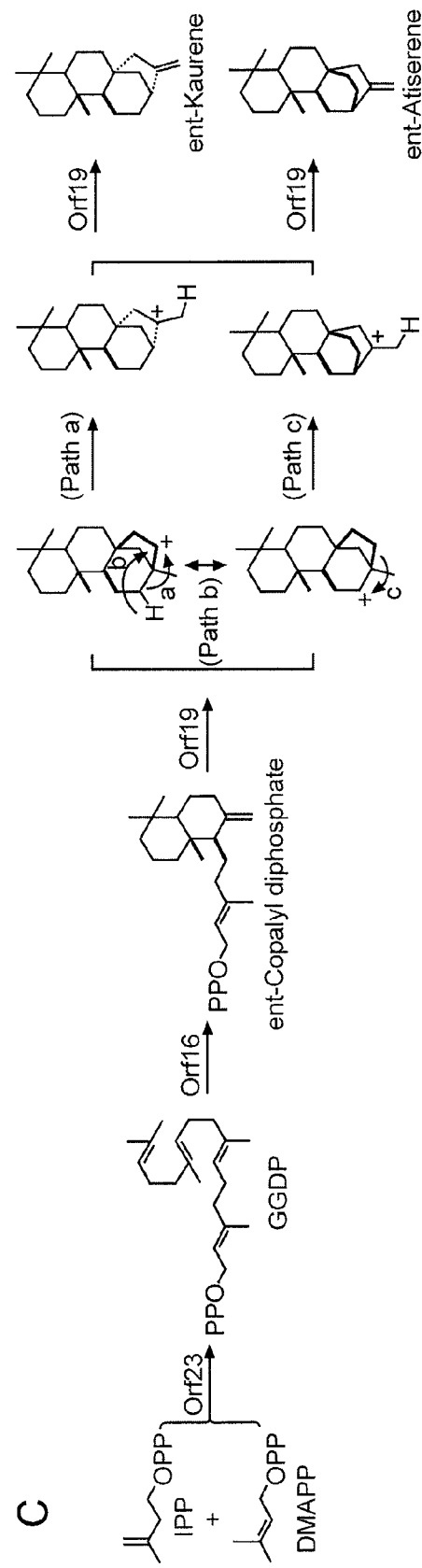
Figure 5:
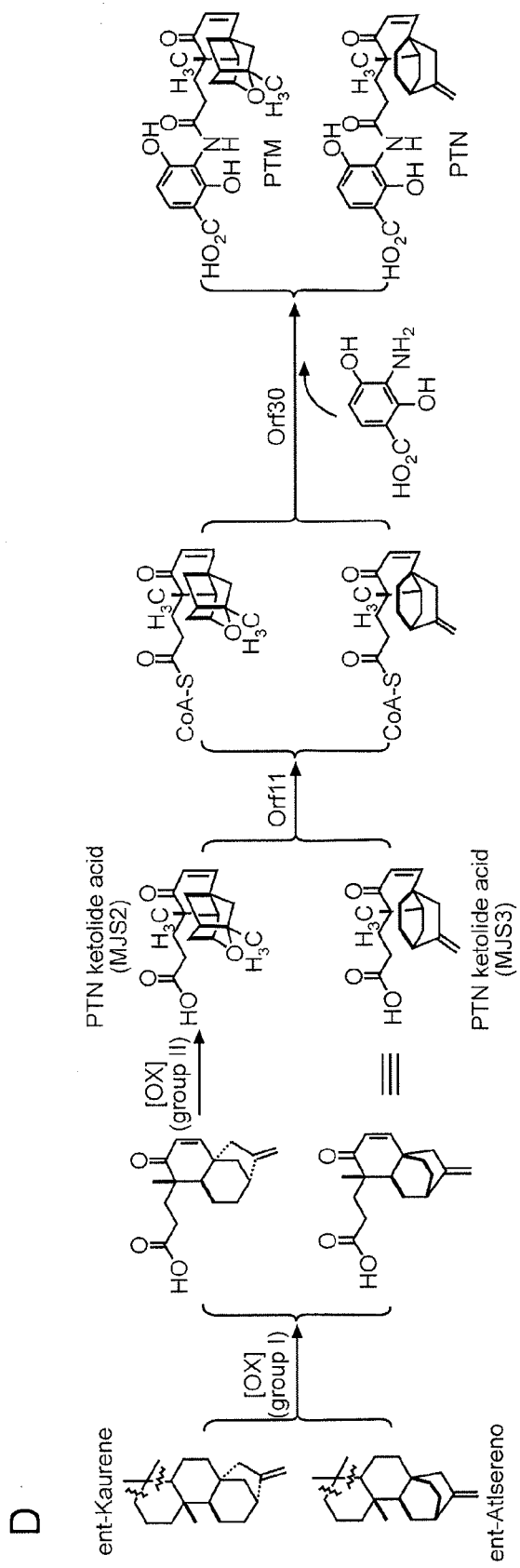

Remarkably, the Δorf28 mutant accumulated three distinct products, MJS1, MJS2, and MJS3 (FIG. 4D). While MJS1 and MJS2 were produced in almost a 1:1 ratio and MJS3 was not detected (FIG. 4C, panel IV), under the conditions optimized for PTM production, MJS2 was the predominant product with both MJS1 and MJS3 produced in low abundance, under the conditions optimized for PTN production (FIG. 4C, panel V). MJS1, MJS2 and MJS3 have now all been isolated and their structures elucidated on the basis of extensive 1D and 2D (COSY, TOCSY, HMQC, and gHMBC) $^1$H, $^{13}$C NMR and APCI-MS analysis. MJS2 is the ketolide moiety of PTM produced as a free acid. MJS1 has the same structure as MJS2 except for an extra hydroxyl group at C-14, most likely resulting from overoxidation of MJS2 by an adventitious oxygenase; MJS1 is therefore a likely shunt metabolite. MJS3 is the ketolide moiety of PTN produced as a free acid. The structures of MJS1, MJS2, and MJS3 are exactly what would be expected from a mutant strain of the S. platensis MA7327 PTM/PTN dual producer, such as Δorf28, whose biosynthetic pathway to the 3-amino-2,4-benzoate moiety has been blocked (FIG. 5D). Isolation of these compounds also suggests a convergent strategy for PTM and PTN biosynthesis with the coupling of the fully modified ketolide and 3-amino-2,4-dihydroxybenzoate moieties most likely as the final step. This was further supported by fermenting the Δorf28 mutant strain in the medium optimized for PTM production supplemented with exogenously added 3,4-AHBA. PTM production was indeed restored with concomitant consumption of MJS2; no apparent difference was observed for MJS1, suggesting MJS1, as a shunt metabolite, may not be a good substrate for the final coupling enzyme (FIG. 4C).

The significance of these experiments is multifaceted. It demonstrates the feasibility to manipulate PTM and PTN biosynthesis in *S. platensis* MA7327 in vivo, thereby permitting us to apply all in vivo recombinant DNA technologies available to characterize PTM and PTN biosynthesis and to engineer the PTM and PTN biosynthetic machinery for novel analogs. It establishes unambiguously that the inventors have cloned the PTM/PTN biosynthetic gene cluster and PTM/PTN production in *S. platensis* MA7327 is controlled by the same biosynthetic machinery. It opens up numerous possibilities to generate PTM and PTN analogs by either precursor-directed biosynthesis—the chemical complementation of PTM production in the Δorf28 mutant by 3,4-AHBA serves as a proof of principle for this strategy—or combination of organic synthesis and biosynthesis—such as chemically coupling MJS1, MJS2, and MJS3 with a battery of aminobenzoates. It is also not difficult to envisage applying the same strategies to clone, characterize, and manipulate the PTN biosynthetic machinery from *S. platensis* MA7339 for comparative studies. Overlap between studying PTM and PTN biosynthesis in MA7237 and PTN biosynthesis in MA7339 will be judiciously kept at minimum.

Figure 12:
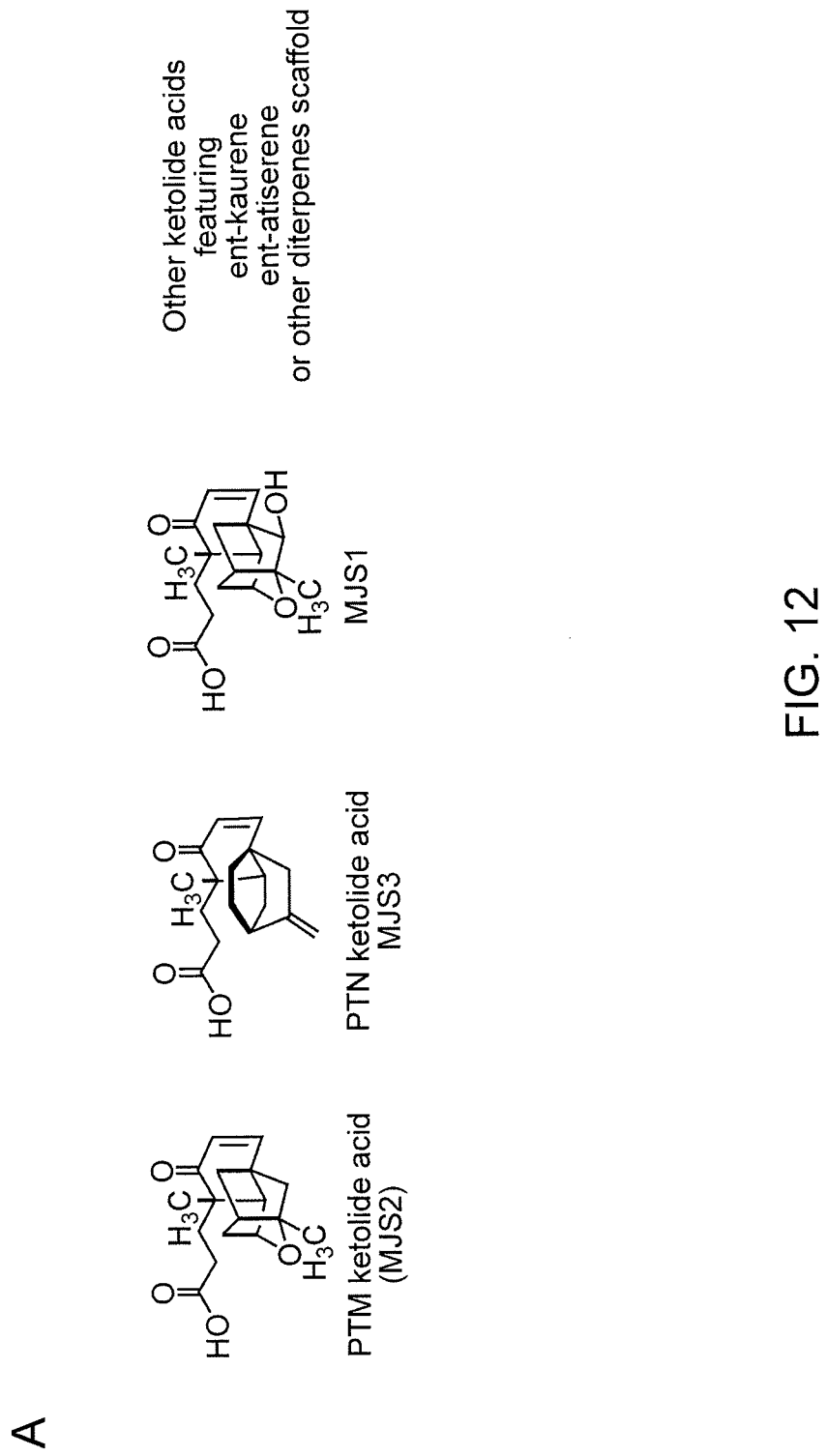
FIGS. 12A-D. Design, strategies, and selected ketolide acid and aminobenzoate building blocks for construction of PTM and PTN analogs.
Figure 12:
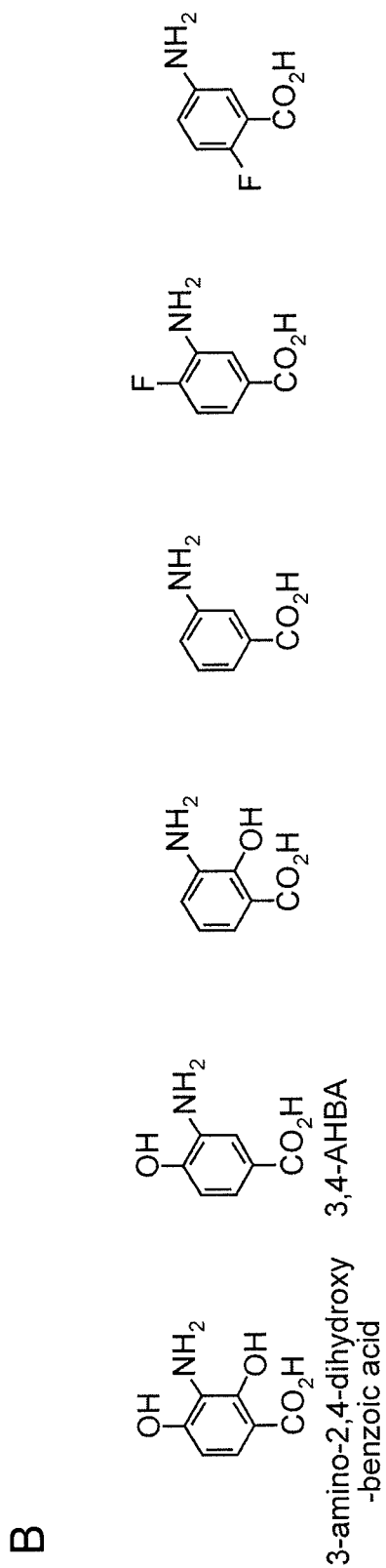
Figure 12:
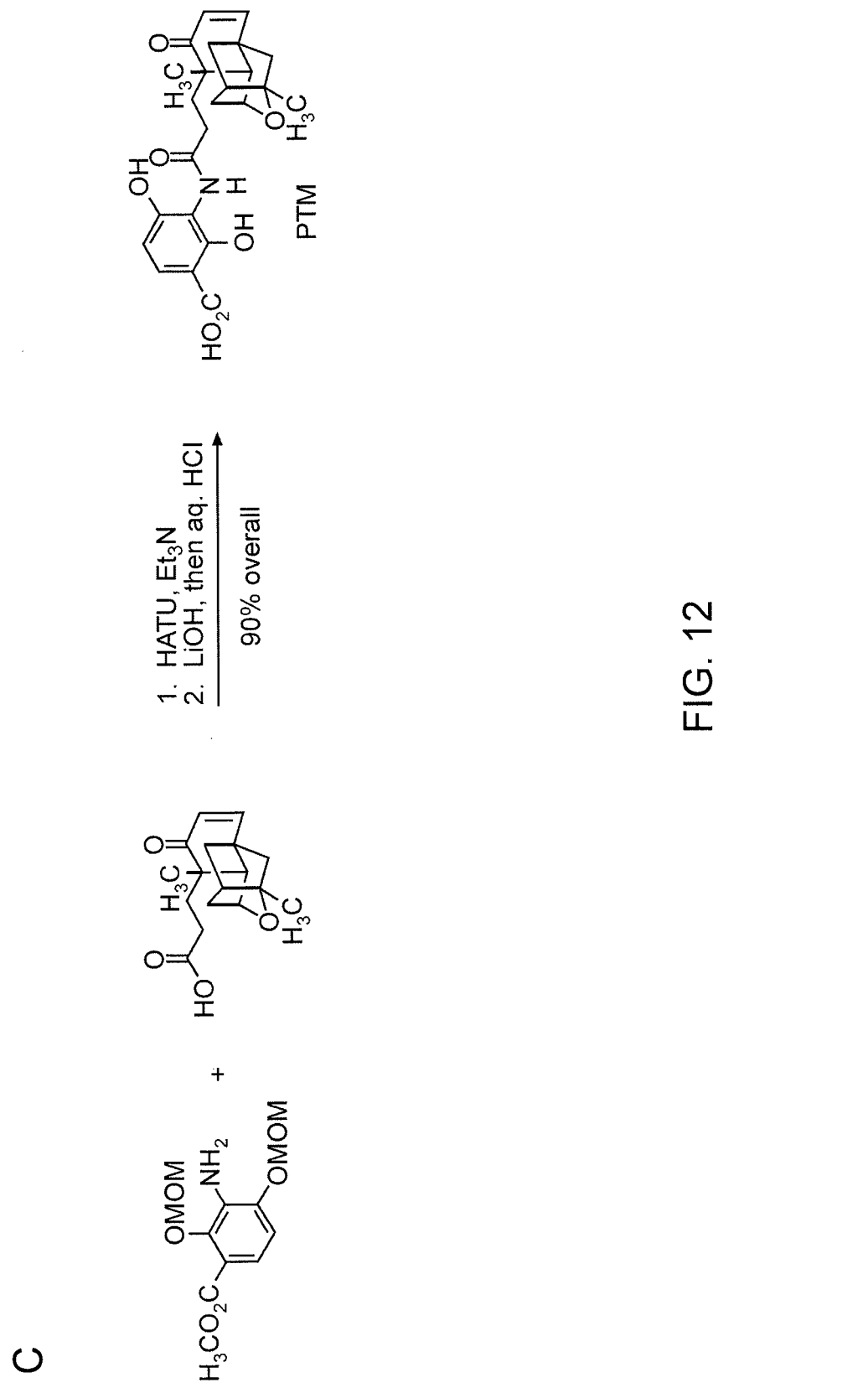
Figure 12:
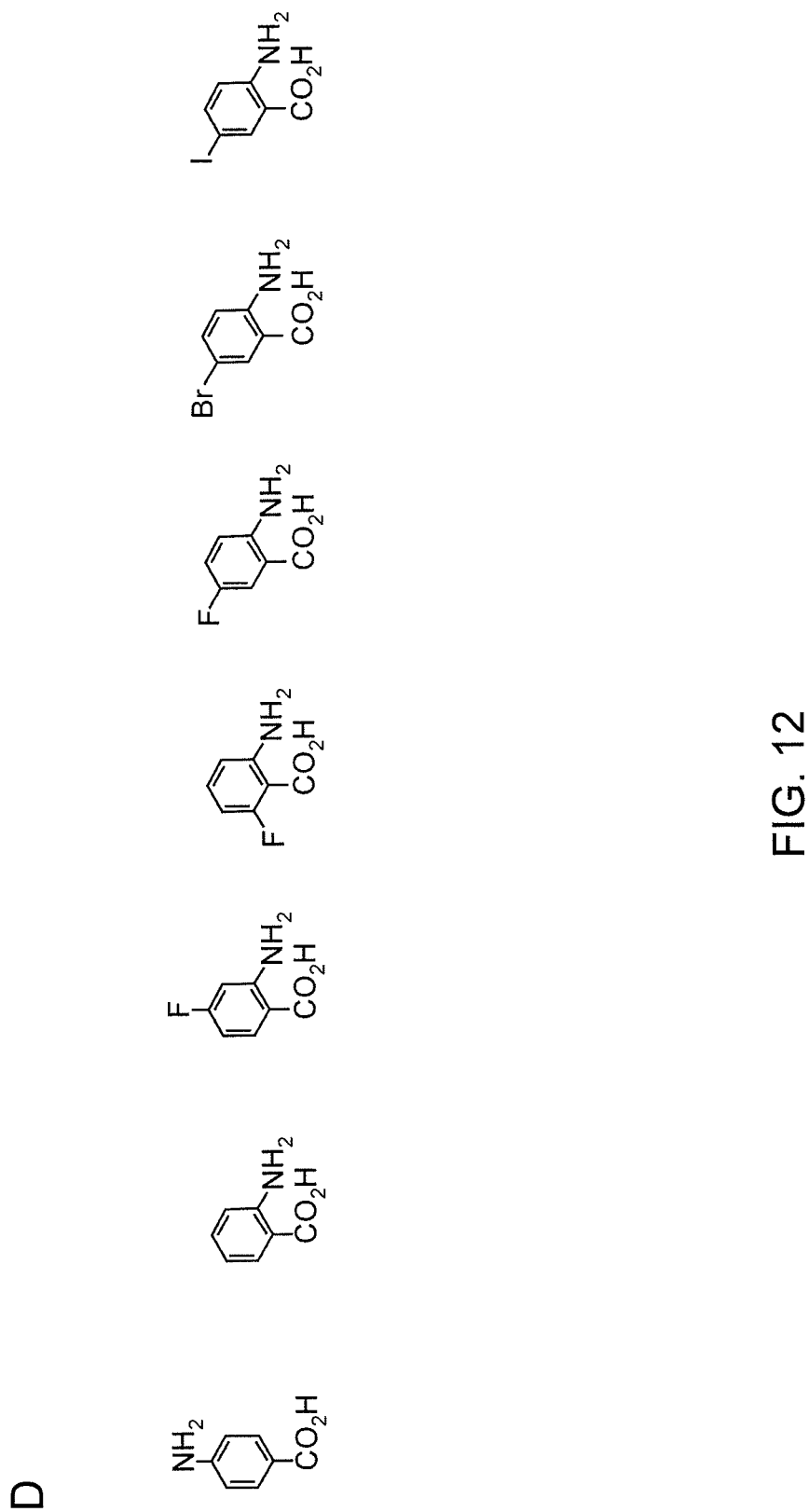

As discussed, the inventors have already isolated the PTM and PTN ketolide acids (i.e., MJS2 and MJS3). Both ketolide acids can also be prepared from hydrolysis of PTM and PTN, respectively. Additional ketolide acids from mutant strains can be produced, as exemplified by MJS1, MJS2, and MJS3 from the Δorf28 mutant (FIG. 12A). A set of substituted 3-aminobenzoates, all commercially available, have been selected, featuring various HO- or F-substitution at 2-, 4-, or 6-positions (FIG. 12B). To prepare PTM and PTN analogs by the precursor-directed biosynthesis strategy, the 3-aminobenzoates will be fed to mutant strains whose biosynthesis of 3-amino-2,4-dihydroxybenzoic acid has been deleted. Incorporation of the exogenously added 3-aminobenzoates by the rest of the PTM or PTN biosynthetic machinery will lead to the production of novel analogs. Complementary to precursor-directed biosynthesis, the inventors can prepare the analogs by direct coupling of the ketolide acids with selected 3-aminobenzoates using standard synthetic methods. A fully protected variant of 3-amino-2,4-dihydroxybenzoic acid has been efficiently coupled with the PTM ketolide acid followed by a mild deprotection step to afford PTM in an excellent overall yield of 90% (FIG. 12C). The inventors will follow the same procedure to couple the various ketolide acids and the selected 3-aminobenzoates, protected in the form of MOM ether and methyl ester if necessary, for the synthesis of a focused, PTM and PTN scaffold-based library.

Complementary to analogs that keep the relative geometry of the 3-aminobenzoate, the PTM and PTN ketolides, and the propionamide (FIGS. 12A-B), the inventors will attempt to make analogs that deviate much further from the PTM and PTN scaffolds. They recognize that the substrate specificity of Orf11 and Orf30 could be a limiting factor for the precursor-directed approach due to the significant structural deviation of the selected precursors from the natural substrates. Therefore, they will apply the organic synthesis strategy. For the ketolide moiety, they will include not only PTM and PTN ketolide acids shown in FIG. 12A, but also metabolites, other than those derived from ent-kaurene and ent-atiserene resulting from engineering of the Orf19 enzymes. For instance, it is known that Orf19 homologs from higher organisms convert ent-CPP to a myriad of diterpenoid scaffolds. Such diterpenoids represent excellent candidates for coupling to 3-aminobenzoates, presumably but not necessarily, closely related to the aminobenzoate endogenous to PTM and PTN. For the aminobenzoate moiety, they will include not only the 3-aminobenzoates shown in FIG. 12B but also 2- or 4-aminobenzoates (all commercially available) (FIG. 12D). Again, they have biased priority of aminobenzoate candidates to F, Br, and I substituted phenyl systems due to their unique properties in proven drugs. Combinatorial coupling between the ketolide acids and the aminobenzoates, should afford another library of PTM and PTN analogs with expanded structural diversity.

Proposed Pathway for PTM and PTN Biosynthesis in *S. platensis* MA7237 and MA7339.

On the basis of the PTM and PTN structures, previous knowledge of 3-aminobenzoate-containing natural product biosynthesis, as well as, terpenoid biosynthesis in general, and the deduced functions of genes identified within the PTM/PTN cluster in *S. platensis* MA7237, the inventor can now propose a pathway to account for both PTM and PTN biosynthesis in great details (FIGS. 6A-D).

Figure 6:
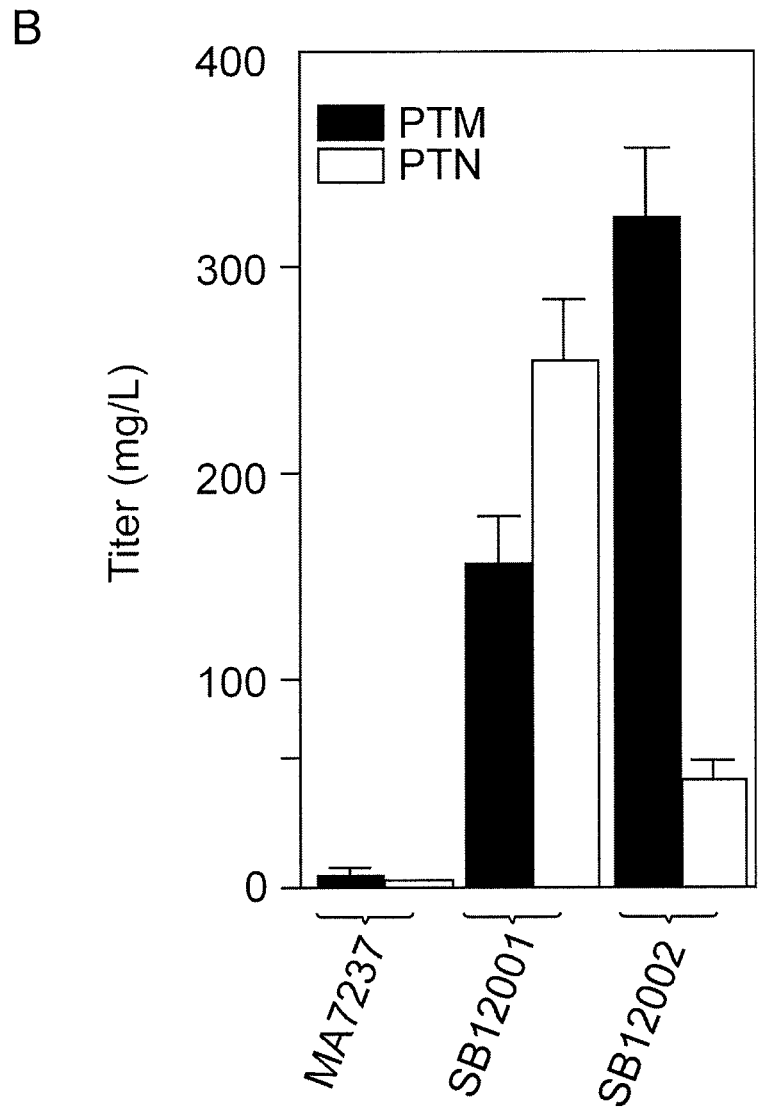
FIGS. 6A-C: Engineering of *S. platensis*.

The inventors have identified three ORFs for the biosynthesis of the 3-amino-2,4-dihydroxybenzoate moiety of PTM. Orf27 and Orf28 catalyze the formation of 3,4-AHBA from a C4 unit of Krebs cycle and a C3 unit of glycolysis as has been predicted previously, and the inventors also favor aspartate semialdehyde (ASA) and dihydroxyacetone phosphate (DHAP) as the two metabolites from Krebs cycle and glycolysis, respectively (Gould et al., 1996; Hu and Floss, 2004; Petricek et al., 2006; Suzuki et al., 2006). Orf29, a member of the salicylic acid hydroxylase family (Zhao et al., 2005), then regiospecifically hydroxylates the C-2 position of 3,4-AHBA to afford 3-amino-4,5-dihydroxybenzoic acid for both PTM and PTN biosynthesis (FIG. 6A).

Both the MV and MEP pathways are known for secondary metabolite biosynthesis in *Streptomyces* (Kuzuyama and Seto, 2003; Dairi, 2005; Kawasaki et al., 2003). *S. platensis* MA7237 apparently employs the MEP pathway for PTM and PTN biosynthesis, as evidenced by the identification of Orf24, Orf25, Orf26—three of the seven enzymes known for IPP and DMAPP biosynthesis via the MEP pathway—within the PTM/PTN cluster (FIG. 6B). It is quite common for genes encoding the MEP pathway to be scattered throughout the microbial genome since this pathway is considered as primary metabolism, supplying the IPP and DMAPP precursors for all metabolic needs (Kuzuyama and Seto, 2003; Dairi, 2005; Kawasaki et al., 2003). The biosynthesis of the ketolide moieties of PTM and PTN starts with Orf23, which is predicted to be a geranylgeranyl diphosphate (GGDP) synthase and catalyzes the synthesis of GGDP from IPP and DMAPP. Homologs of Orf23 have been identified from several other terpenoid pathways in *Streptomyces* (Kuzuyama and Seto, 2003; Durr et al., 2006; Kawasaki et al., 2006). Orf16, an ent-CPP synthase characterized with the DXDD motif for the class II terpenoid synthases, catalyzes the formation of ent-CPP. Similar enzymes are also known in *Streptomyces* (Hornung et al., 2007). Orf19 is an ent-kaurene synthase, characterized with the DDXXD motif for the class I terpenoid synthases (Davis and Croteau, 2000; Kuzuyama and Seto, 2003; Dairi, 2005; Kawasaki et al., 2003; Tudzynski et al., 2005; Toyomasu et al., 2007; Xu et al., 2007a; Prisic et al., 2007), and, to the inventors' knowledge, Orf19 represents the first ent-kaurene synthase identified from bacteria. They propose Orf19 catalyzes the regiospecific cyclization of ent-CPP to afford a carbocation, which undergoes either a direct 1,3-carbon shift followed by deprotonation to yield ent-kaurene en route to PTM (FIG. 6C, path a) or a sequential 1,3-hydride shift and 1,3-carbon shift followed by a similar deprotonation step to yield ent-atiserene (FIG. 6C, path b/c). Catalytic specificity and product promiscuity for ent-kaurene synthase from higher organisms have been noted previously but little is known about their mechanism (Tudzynski et al., 2005; Xu et al., 2007a; Xu et al., 2007b). The inventors propose that it is the product promiscuity of Orf19 in *S. platensis* MA7327 and its homolog in *S. platensis* MA7339 that determine MA7327 as a PTM/PTN dual producer, but MA7339 as an exclusive PTN producer. The two ent-kaurene synthases from MA7327 and MA7339 represent a rare occasion of enzyme evolution caught in action. Comparative studies of these enzymes therefore provide an outstanding opportunity to investigate the molecular mechanism of how ent-kaurene synthase control and dictate product outcome.

While the bioinformatics data alone may fall short of predicting the precise timing of conversion of ent-kaurene to PTM and ent-atiserene to PTN, isolation and structural elucidation of MJS2 and establishment of its intermediacy in PTM biosynthesis, as well as, the isolation of MJS3 provide strong circumstantial evidence supporting a convergent model for PTM and PTN biosynthesis, with ketolide acids (i.e., MJS2 and MJS3) as the penultimate intermediates. There are six ORFs—Orf15, Orf17, Orf18, Orf20, Orf22, Orf33—predicted to be oxidoreductases, and they serve as logical candidates for these steps (FIG. 6D).

The six oxidoreductases could be further divided into two groups. Group I enzymes display relaxed substrate specificity and can oxidatively process both ent-kaurene and ent-atiserene to furnish the cyclohexenone moiety with the propionic acid side chain common to both PTM and PTN. Group II enzymes are specific only to ent-kaurene-derived intermediates en route to PTM. Hydroxylation at C-10 followed by ring closure with C-15 affords the characteristic ether linkage found in PTM. In contrast, the corresponding ent-atiserene-derived intermediates presumably are poor substrates for these enzymes. Direct coupling of the ent-atiserene-derived acid intermediate (i.e, MJG3) without further modification at its exocyclic double bond with the aminobenzoate moiety would afford PTN (FIG. 6D). Comparative studies of these enzymes in *S. platensis* MA7237 and MA 7339 will allow differentiation of their roles in PTM and PTN biosynthesis. The group II enzymes should be absent or dysfunctional in the PTN cluster from *S. platensis* MA7339 since it is an exclusive PTN producer.

Finally, Orf11 activates both the PTM and PTN ketolide acids as CoA esters, setting the stage for the final coupling with the aminobenzoic acid moiety. Orf30 catalyzes the final coupling reactions, completing the biosynthesis of PTM and PTN (FIG. 6D). CoA ligases similar to Orf11 and amide synthases similar to Orf30 are known for natural product biosynthesis in *Streptomyces* (August et al., 1998; Floss and Yu, 1999; Du et al., 2000; Kwon et al. 2002; Cooke et al., 2007; Steffensky et al., 2000a; Steffensky et al., 2000b; Wang et al., 2000; Pojer et al., 2002; Galm et al., 2002). The fact that Orf11 activates both the PTM and PTN ketolide acids and Orf30 catalyzes amide bond formation for both PTM and PTN indicates intrinisic substrate promiscuity of these enzymes, a property that could be further exploited for PTM and PTN analog production by the directed-biosynthesis method (Eustaquio et al., 2005; Eustaquio et al., 2003; Xu et al., 2004; Li and Heide, 2005; Anderle et al., 2007).

Regulation of PTM and PTN Biosynthesis in *S. platensis* MA7327.

Three ORFs—Orf34, Orf21, and Orf9—are predicted to play regulatory roles in PTM and PTN production. Orf34 is homologous to members of the GntR family of transcriptional regulators. More than 1,300 members of the GntR family are known, and they share a common helix-turn-helix motif for binding DNA (Hillerich and Westpheling, 2006). GntR members characterized so far appear to behave as transcriptional repressors. The inventors propose that Orf34 acts similarly as a negative regulator for the PTM/PTN pathway in MA7237. Inactivation of orf34 should therefore afford a recombinant strain with an improved PTM and PTN titer. The second gene product predicted to be involved in regulation of PTM production is Orf21, which contains conserved domains indicative of kinase activity. Lastly, orf9 encodes a putative DNA binding protein. Both Orf21 and Orf9 could have positive regulatory effects on the PTM/PTN pathway, and overexpression of these genes may improve PTM and PTN production in *S. platensis* MA7327 (Hopwood, 1999; Demain and Vaishnav, 2004; Bibb, 2005; Takano, 2006; Cundliffe, 2006).

Mechanisms of PTM and PTN Resistance in *S. platensis* MA7327.

Bioinformatics analysis of the genes within the cloned PTM/PTN cluster has been remarkably informative in helping us formulate mechanistic hypothesis of self-resistance to PTM and PTN in *S. platensis* MA7327. While the inventors cannot predict a priori if the fatty acid synthase complex in *S. platensis* MA7327 or MA7339 has acquired mutations to provide PTM and PTN resistance, they have identified three ORFs—Orf31, Orf32, and Orf14—within the PTM/PTN cluster that serve as potential candidates to confer PTM and PTN resistance in three independent mechanisms. Orf31 shows significant homology to members of the FabB/F family of $\beta$-ketoacyl-ACP synthases (Campbell and Cronan, 2001). The inventors propose that Orf31 is a variant of FabF that is resistant to the inhibitory effect of PTM and PTN. During the early vegetative growth of *S. platensis* MA7327, fatty acid biosynthesis, as in all bacteria, is controlled by the type II fatty acid synthase, including the essential FabB, FabF, and FabH subunits. As growth slows and enters the stationary phase, the PTM and PTN biosynthetic machinery starts to produce PTM and PTN with the concomitant expression of orf31. Orf31, produced on demand, will then take over the role of FabB/F when PTM and PTN production is in full force. Thus, Orf31, in supporting fatty acid biosynthesis, ensures self-resistance to PTM and PTN in *S. platensis* MA7237.

Orf32 belongs to the family of acetyl CoA acetyltransferases, and this family of enzymes catalyzes the condensation of two molecules of acetyl CoA to form acetoacetyl CoA (El-Mansi et al., 2006). Strikingly, this is functionally equivalent to FabH, the target of PTN, which catalyzes the condensation between acetyl CoA and malonyl-ACP to afford acetacetyl-ACP to initiate fatty acid biosynthesis (Campbell and Cronan, 2001). One could then imagine that Orf32, in fact, is a variant of a condensing enzyme that has acquired the ability to synthesize acetoacetyl-ACP in mechanistic analogy to FabH. Since there is little sequence homology between Orf32 and FabH, Orf32 will not be sensitive to PTN inhibition. As a result, Orf32 will take over the role of FabH for fatty acid biosynthesis when *S. platensis* MA7327 starts to produce PTN, thereby conferring self-resistance to PTN. It would be decisive and rewarding to compare and contrast the resistance mechanisms between the *S. platensis* MA7327 and MA7339 strains, given the fact that MA7327 is a PTM/PTN dual producer whereas MA7339 is an exclusive PTN producer.

In contrast to Orf31 and Orf32, both of which likely provide self-resistance to PTM and PTN in *S. platensis* MA7327 via the strategy of the target replacement (Cundliffe, 1989; Cundliffe, 1992), Orf14 could potentially provide PTM and PTN self-resistance by drug sequestration. Orf14 shows significant homology to members of the prenyltransferase family of enzymes, such as GGDP synthase, and these enzymes catalyze the condensation of isoprene units to make terpenoids (Davis and Croteau, 2000; Kuzuyama and Seto, 2003; Dairi, 2005; Christianson, 2006). However, Orf14 cannot be functional as a prenyltransferase since it lacks the characteristic active site residues. Should Orf14 retain and evolve its affinity towards the ancestral terpenoid substrates into specific binding to PTM and PTN, Orf14 could then sequester PTM and PTN from the S. platensis MA7327 fermentation, thereby conferring self-resistance to PTM and PTN. Pending experimental confirmation, it is remarkable to identify three potential mechanisms for PTM and PTN resistance on the basis of bioinformatics analysis of the PTM and PTN gene cluster from S. platensis MA7327 alone, underscoring once again the power of microbial genomics in advancing studies of secondary metabolism (Khosla and Keasling, 2003; Clardy and Walsh, 2005; Walsh, 2004; Weissman and Leadlay, 2005; Baltz, 2006a; Kohen and Carter, 2005; Galm and Shen, 2006; Van Lanen and Shen, 2006; Baltz, 2006b; Floss, 2006). It is common for antibiotic producers to evolve multiple resistance mechanisms to ensure self-protections (Cundliffe, 1989; Cundliffe, 1992; D'Costa et al., 2006).

Taken together, these preliminary studies: (i) confirm that the PTM/PTN biosynthetic gene cluster has been cloned and sequenced from S. platensis MA7327 and application of the same strategy ensures the access to the PTN biosynthetic gene cluster from S. platensis MA7339, (ii) establish a unified pathway for PTM and PTN production featuring novel chemistry and enzymology for 3-amino-2,4-dihydroxybenzoic acid biosynthesis, the first ent-kaurene synthase of bacterial origin, as well as numerous novel enzymes to account for the formation of the unprecedented ketolide scallfords found in PTM and PTN, (iii) enable the inventors to formulate ever firmer hypotheses, on which the current application is based, extending into the mechanisms for PTM and PTN biosynthesis, regulation, and self-resistance, and (iv) demonstrate the feasibility of carrying out the proposed studies on PTM and PTN biosynthesis and resistance and on engineering the PTM and PTN biosynthetic machinery for titer improvement and analog generation with the ultimate goal of developing PTM and PTN into a new class of clinically useful antibacterial drugs.

Engineered S. platensis SB12001 and SB12002 Strains Overproducing PTM and PTN.

The inventors have predicted that Orf34 is a member of the GntR family of transcriptional repressors and inactivation of orf34 in the wild-type MA7327 strain should afford recombinant strains with improved PTM and PTN titers. Two S. platensis recombinant strains, SB12001 and SB12002, whose orf34 has been inactivated by a gene replacement with the aac(3)IV apramycin resistance cassette, have been isolated and their genotype confirmed by Southern analysis. HPLC analysis confirmed dramatic improvement of both PTM and PTN titers by these strains. Surprisingly, the two overproducing strains were found to have distinct phenotypes, with SB12002 routinely producing more PTM and SB12001 routinely favoring PTN production (FIG. 5B). As the targeted orf34 replacement in these strains has been shown to be identical by Southern analysis, this titer difference can best be explained by a fortuitous genetic variation introduced during the isolation of these mutant strains. Under the optimized production conditions, SB12002 produces PTM with a yield of 330±40 mg/L and SB12001 produces PTN with a yield of 230±50 mg/L, respectively. These titers represent up to 165-fold improvement of PTM production and 230-fold improvement of PTN production over the titers reported initially by Merck from the wild-type S. platensis MA7327 strain (FIG. 6B). Merck recently also reported PTM titer of 52 mg/L with the wild-type MA7327 strain in a fermentation tank with an improved medium (Nicolaou et al., 2008). Application of the newly developed fermentation process to the engineered PTM or PTN overproducer concervivably will further improve PTM or PTN titers.

In conclusion, the inventors have solved the problem of limited supply of PTM and PTN by fermentation, and the engineered PTM and PTN overproducers will greatly facilitate the effort to generate PTM and PTN analogs by combinatorial biosynthesis methods.

Investigation of PTM and PTN-Self Resistance-Mechanism.

Having large quantity (multiple grams) of PTM and PTN in hand from the overproducers, the inventors systematically examined the sensitivity of a battery of Streptomyces towards PTM or PTN. Remarkably, they have identified strains that are sensitive to both PTM and PTN, as exemplified by Streptomyces avermitilis, or PTN but not PTM, as exemplified by Streptomyces albus J1074 (FIG. 6C). The differential sensitivity of the organisms tested towards PTM and PTN is consistent with the established mode of action for PTM and PTN (i.e., PTM as a FabB/F inhibitor while PTN as a FabB/F and FabH dual inhibitor)—targeting two essential proteins should lead to lower resistance potential than targeting only one. The inventors have predicted Orf31 (a homolog of FabB/F) and Orf32 (a homolog of FabH) within the cloned PTM/PTN cluster to confer PTM and PTN resistance to S. platensis MA 7327. The inventors can now test these hypotheses directly by cloning orf31, orf32, or both into S. avermitilis and S. albus to investigate their resistance to PTM, PTN or both. These results now set the outstanding stage to investigate PTM and PTN resistance mechanism and to understand PTM and PTN resistance within the producers. His will allow the inventors to predict, understand, and thereby combat future PTM and PTN resistance in clinical settings.

In Vivo and In Vitro Characterization of the PTM and PTN Biosynthetic Machinery.

In addition to the Δorf28 (FIGS. 4A-D) and Δorf34 mutants (FIG. 6B), the inventors have now also isolated and confirmed the genotype and phenotype of the following gene mutants: (i) Δorf33, Δorf34, Δorf35, Δorf36 establishing the downstream boundary to be between orf34 and orf35; (ii) Δorf5, Δorf7, Δorf11 revealing the upstream boundary to be between orf5 and orf6 (FIGS. 3A-B; Table 1); and (iii) Δorf20 abolishing PTM production only but having no effect on PTN production and supporting its assignment as a group II oxidoreductase (FIGS. 5A-D). Complementary to these in vivo efforts, Orf16 (ent-copalyl synthase), Orf19 (ent-kaurene synthase), and Orf29 (flavin-dependent benzoate hydroxylase) (Table 1) have also been overproduced in E. coli. Taken together, these results further demonstrate the feasibility of the proposed studies, ensuring the successful completion of functional characterization of the PTM and PTN biosynthetic machinery by in vivo and in vitro methods.

Example 2

Materials and Methods

Antibiotic Production Conditions.

500 µl of dense cultures grown in R2YE (sucrose 103 g/L, $K_2SO_4$ 0.25 g/L, $MgCl_2 \cdot 6H_2O$ 10.12 g/L, dextrose 10 g/L, Difco Casaminoacids 0.1 g/L, Difco yeast extract 5 g/L, TES 5.73 g/L, adjust to pH7.0, autoclave, then add 6 ml of 1 M NaOH, 10 ml of 0.5% $KH_2PO_4$, 20 ml of 1 M $CaCl_2$, 15 ml of 20% proline, and 2 ml of trace elements per liter of medium)

were used to inoculate 50 ml ISM-3 seed medium (Difco yeast extract 15 g/L, Difco malt extract 10 g/L, MgSO$_4$ 0.244 g/L, FeCl$_3$.6H$_2$O 0.3 g/L, dextrose 20 g/L, pH 7.0) in 250 ml baffled flasks. Seed cultures were grown at 28° C., 250 rpm in incubated shakers for 48 hours. 500 µl seed culture was used to inoculate 50 ml production medium (SLY: Stadex 60K dextrin 40 g/L, lactose 40 g/L, Difco yeast extract 5 g/L, pH7.0; SLYM: SLY with MOPS sodium salt 20 g/L pH 7.3; PCNM: yeast extract 6 g/L, malt extract 15 g/l, dextrose 6 g/L, MOPS sodium salt 20 g/L, pH 7.4, autoclave then add 5 ml trace elements) in 250 ml flasks supplemented with 1.5 g Amberlite XAD-16 resin. Production cultures were incubated for 8 days at 28° C., 250 rpm prior to harvest.

Titer Determination.

Harvested resin and mycelia fragments from 50 ml cultures were separated from broth by centrifugation and washed three times with dH$_2$O, Next, the resin was extracted with 4×6 ml acetone to recover >99% of PMN/PCN (data not shown). Acetone was removed under reduced pressure and crude extract was resuspended in methanol prior to analysis on a Waters 510 HPLC system with photodiode array detector (Waters, Milford, Mass.) using an Apollo C$_{18}$ column (5 µm, 4.6×250 mm, Grace Davison Discovery Sciences, Deerfield, Ill.) and a 20 minute solvent gradient (1 ml/min) from 15% acetonitrile in H$_2$O, 0.1% formic acid to 90% acetonitrile in H$_2$O, 0.1% formic acid. Peak area at 240 nm was used to quantify PMN and PCN based on standard calibration curves.

An Engineered *Streptomyces platensis* Overproducing Antibiotics Platensimycin and Platencin.

The discovery of platensimycin (PMN) and platencin (PCN) as an entirely new class of antibacterial antibiotics with a mode of action not exploited by current drugs represents an important step in the fight against antibiotic resistance (Wang et al., 2006; Wang et al., 2007). Both compounds are potent and selective inhibitors of bacterial (type II) fatty acid synthesis. PMN specifically targets the elongation β-ketoacyl-ACP synthase (KAS), FabF (Wang et al., 2006), while PCN has a dual mode of action, targeting both FabF and the initiation KAS, FabH (Wang et al., 2007). Both natural products are effective against a broad spectrum of Gram-positive pathogens, including methicillin-resistant *Staphylococcus aureus* (MRSA) and vancomycin-resistant enterococci (VRE) (Wang et al., 2007). Although PMN has been proven effective in clearing *S. aureus* infection from a mouse model, the high doses and suboptimal delivery system required highlights the need for further structure refinement prior to clinical trials. Multiple total syntheses of both compounds as well as numerous analogs underscore the excitement generated by these compounds as leads for novel antiinfectives (Nicolaou et al., 2008; Nicolaou et al., 2007a; Nicolaou et al., 2007b; Nicolaou et al., 2007c).

PMN was isolated with a yield of 2-4 mg/L from *S. platensis* MA7327 (Singh et al., 2006), and PCN was isolated from *S. platensis* MA7339 with a yield of 1 mg/L (Jayasuriya et al., 2007). Subsequent titer improvement in the producing strain has led to a recent report of *S. platensis* MA7237 producing PMN with yields up to 56 mg/L (Herath et al., 2008). No such improvement of PCN titer has been reported to date. Strains capable of producing higher yields of PMN, PCN, or both will facilitate the development of these promising leads into clinical agents. Towards this end, the inventors have developed a genetic system for the original producing strain, *S. platensis* MA7237, and exploited the regulatory mechanism to engineer *S. platensis* strains capable of overproducing both PMN and PCN in titers of 323 mg/L and 255 mg/L, respectively.

First, the inventors obtained *S. platensis* MA7237 and confirmed its ability to produce PMN at slightly above the reported levels (10.1 mg/L) in production medium SLY (supplementary materials). They subsequently confirmed the ability of this strain to produce both PMN and PCN in equal amounts (~1 mg/L) when grown in reported PCN production conditions. This titer is on par with levels seen in the reported PCN producer, MA7339 (Jayasuriya et al., 2007). While a rigorous medium optimization was not performed, it was found that the addition of Amberlite XAD16 resin to the production cultures led to significant increases in titer as well as a more efficient and environmentally conscious isolation (Table 2). Thus, resin was included in all subsequent fermentations.

TABLE 2

| | MA7237 without resin | MA7237 | SB12001 | SB12002 |
|---|---|---|---|---|
| | PMN Titer (mg/L) per *S. platensis* strain | | | |
| SLY | 4.45 | 27.5 | 154 | 324 |
| | 8.08 | 16.9 | 133 | 331 |
| | 10.6 | 27.4 | 144 | 275 |
| | 10.3 | 8.04 | 162 | 353 |
| | 14.6 | 6.79 | 192 | 330 |
| | 12.7 | 9.10 | | |
| | | 8.70 | | |
| | | 19.6 | | |
| | | 12.3 | | |
| | 10.1 ± 3.56 | 15.1 ± 8.16 | 157 ± 22.4 | 323 ± 28.8 |
| SLYM | 0.172 | 1.33 | 69.6 | 209 |
| | 0.342 | 0.42 | 71.0 | 137 |
| | 0.252 | 1.20 | 75.0 | 221 |
| | 4.52 | 1.71 | 70.1 | 249 |
| | | | 64.7 | 195 |
| | | | 38.7 | |
| | | | 44.3 | |
| | 1.32 ± 2.13 | 1.16 ± 0.542 | 61.9 ± 14.4 | 202 ± 41.5 |
| PCNM | 0.714 | 2.12 | 46.9 | 131 |
| | 2.50 | 2.08 | 38.9 | 112 |
| | 1.73 | | | |
| | 1.65 ± 0.896 | 2.10 | 42.9 | 122 |
| | PCN Titer (mg/L) per *S. platensis* strain | | | |
| SLY | 0.118 | 2.50 | 288 | 64.2 |
| | 0.235 | 2.47 | 223 | 42.1 |
| | 0.285 | 2.00 | 244 | 47.5 |
| | 0.137 | 1.90 | 234 | 42.1 |
| | | 3.63 | 285 | 42.5 |
| | | | | 58.3 |
| | | | | 61.8 |
| | | | | 51.9 |
| | 0.194 ± 0.0796 | 2.50 ± 0.687 | 255 ± 29.9 | 51.3 ± 9.16 |
| SLYM | 0.187 | 0.777 | 234 | 55.4 |
| | 0.127 | 0.260 | 272 | 54.2 |
| | 0.559 | 0.600 | 213 | 50.4 |
| | | 0.801 | 246 | 65.0 |
| | | 1.34 | 245 | 50.0 |
| | | | | 59.0 |
| | 0.291 ± 0.234 | 0.756 ± 0.392 | 242 ± 21.4 | 55.7 ± 5.66 |
| PCNM | 0.742 | 0.850 | 101 | 27.5 |
| | 1.68 | 0.658 | 143 | 30.3 |
| | 1.16 | | | |
| | 1.19 ± .470 | 0.754 | 122 | 28.9 |

PMN/PCN production by wild-type and engineered strains in various media. Titers (mg/L) for *S. platensis* MA7237, SB12001, and SB12002 are reported in three media: SLY, PCNM (reported platencin production medium) and SLYM (buffered production medium). Averages are shown in bold face and standard deviation is included for data points with three or more independent trials. The largest yields PCN and PMN are obtained in SLY medium and buffering the medium serves to increase the ratio of PCN:PMN at the expense of total titer. Although PCNM was the best medium for PCN production in the wildtype strain, the engineered strains produced more in SLY.

Having confirmed production of both compounds, the inventors next set out to identify the locus of the biosynthetic gene cluster(s) responsible for producing these compounds. A PCR-based approach was used with primers designed to amplify a fragment of the gene 3-amino-4-hydroxybenzoic acid synthase, thought to be involved in the biosynthesis of the 3-amino-2,4-dihydroxybenzoic acid moiety of PMN/PCN (Herath et al., 2007). Using total S. platensis MA7237 DNA as a template, only a single DNA fragment was amplified. This suggests that PMN and PCN share at least a portion of their biosynthetic machinery. Although a complete sequencing and analysis of the surrounding gene cluster is underway, preliminary sequencing revealed orf34 (Genbank Accession # EU805802), a putative transcriptional repressor, in the cloned locus. ORF34 shows sequence similarity to the GntR family of transcriptional regulators (SI 2), leading the inventors to postulate that it may be involved in the regulation of PMN/PCN production and that inactivation of ORF34 could lead to altered production levels of PMN, PCN, or both.

Thirdly, the inventors developed a genetic system for S. platensis MA7237 to enable a detailed characterization of antibiotic production in this native producer. Plasmid DNA was introduced via intergenic conjugation, with Escherichia coli S17-1 as the donor strain, and use of φC31-mediated site-specific integration vectors such as pSET152 (Bierman et al., 1992) resulted in approximately 1 exconjugate per $10^5$ S. platensis spores. When homologous recombination was required, the frequency of exconjugates dropped to $\sim 10^{-8}$. The sensitivity of S. platensis MA7237 to the antibiotics apramycin, thiostrepton, erythromycin, and kanamycin was verified to establish a list of possible selection markers for genetic recombination.

Figure 7:
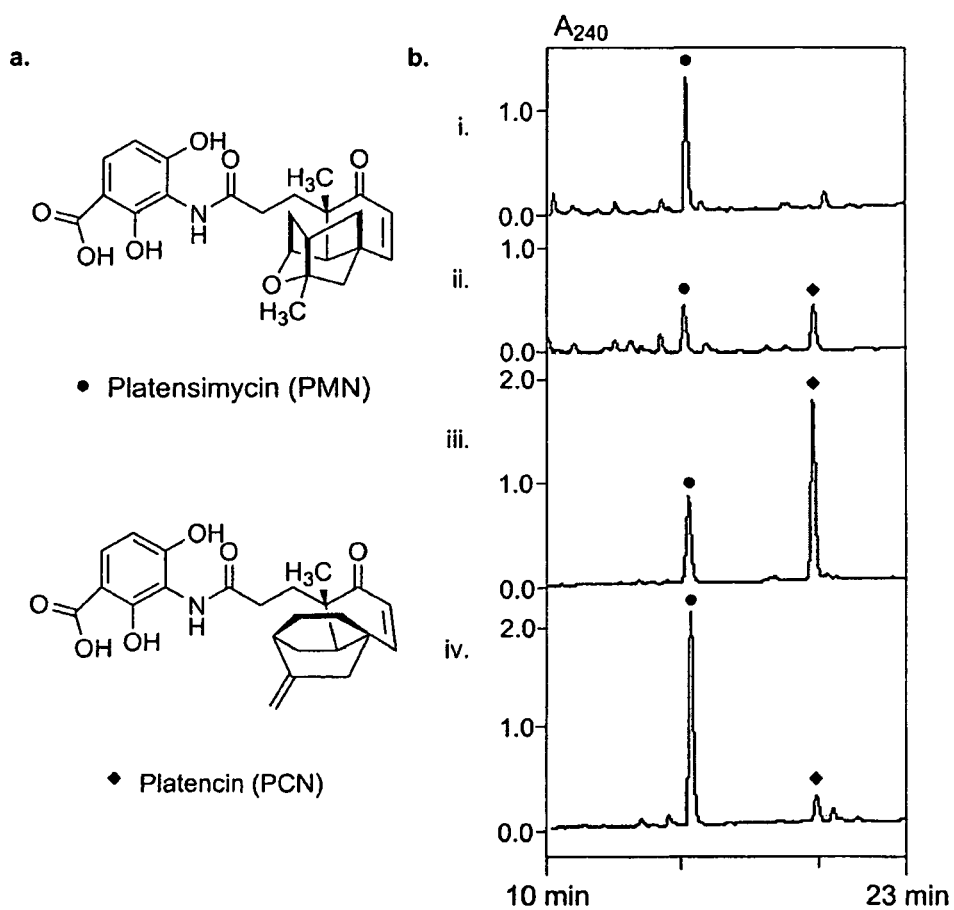
FIGS. 7A-B: Production of PMN and PCN by *S. platensis* MA7237, SB12001, and SB12002.
Figure 8:
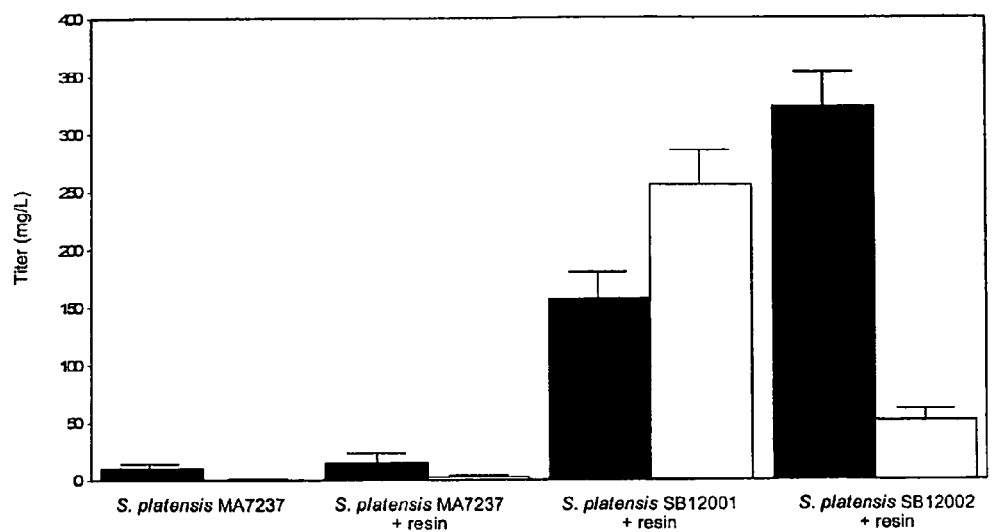
FIG. 8: Production of PMN (solid black) and PCN (solid white) by wild-type and engineered strains. Error bars denote one standard deviation from the statistical mean, calculated from at least 3 independent trials.
Figure 9:
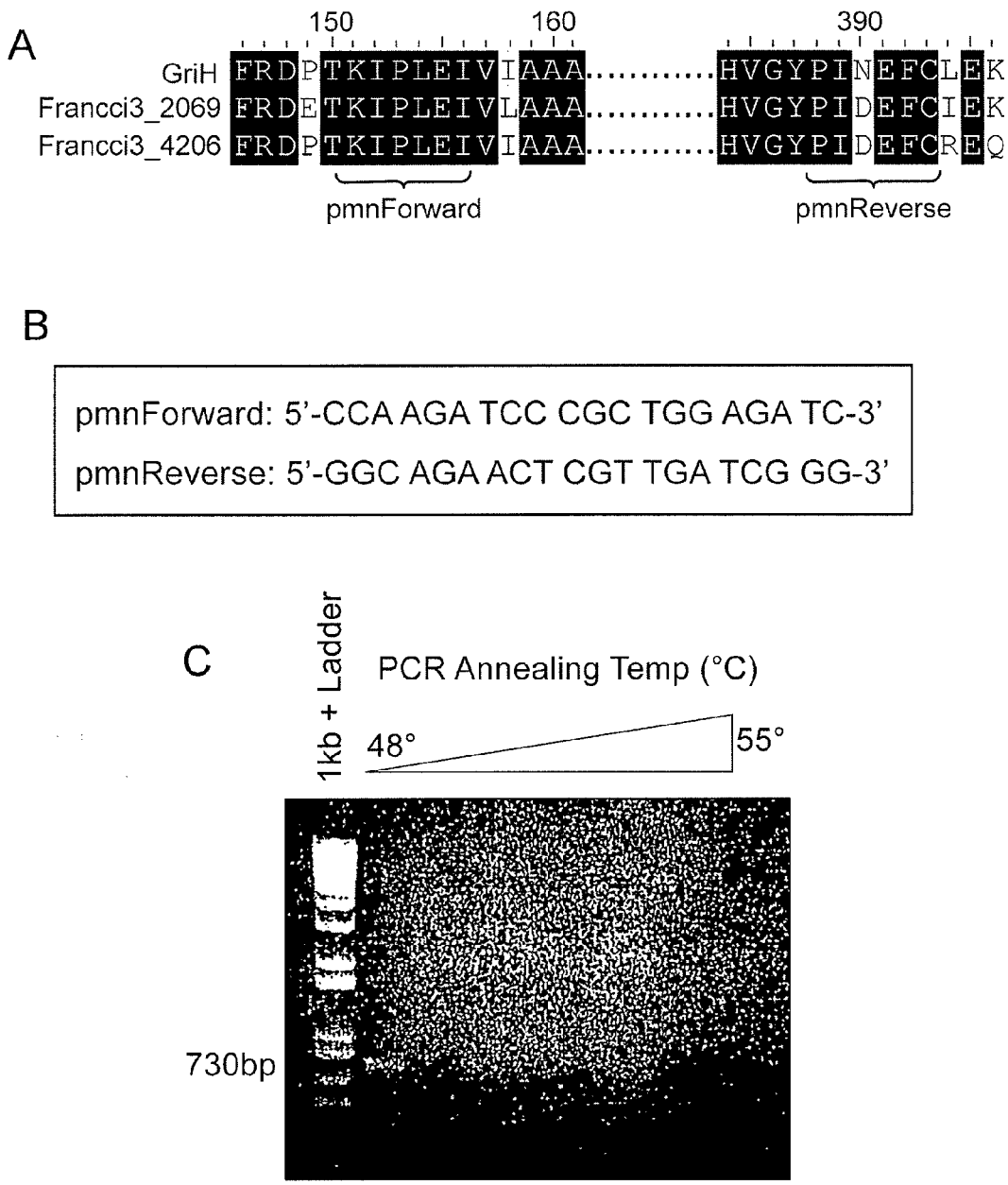
FIGS. 9A-C: Primer design for amplification of 3-amino-4-hydroxybenzoic acid (AHBA) synthase from *S. platensis* MA7237 genomic DNA.
Figure 10:
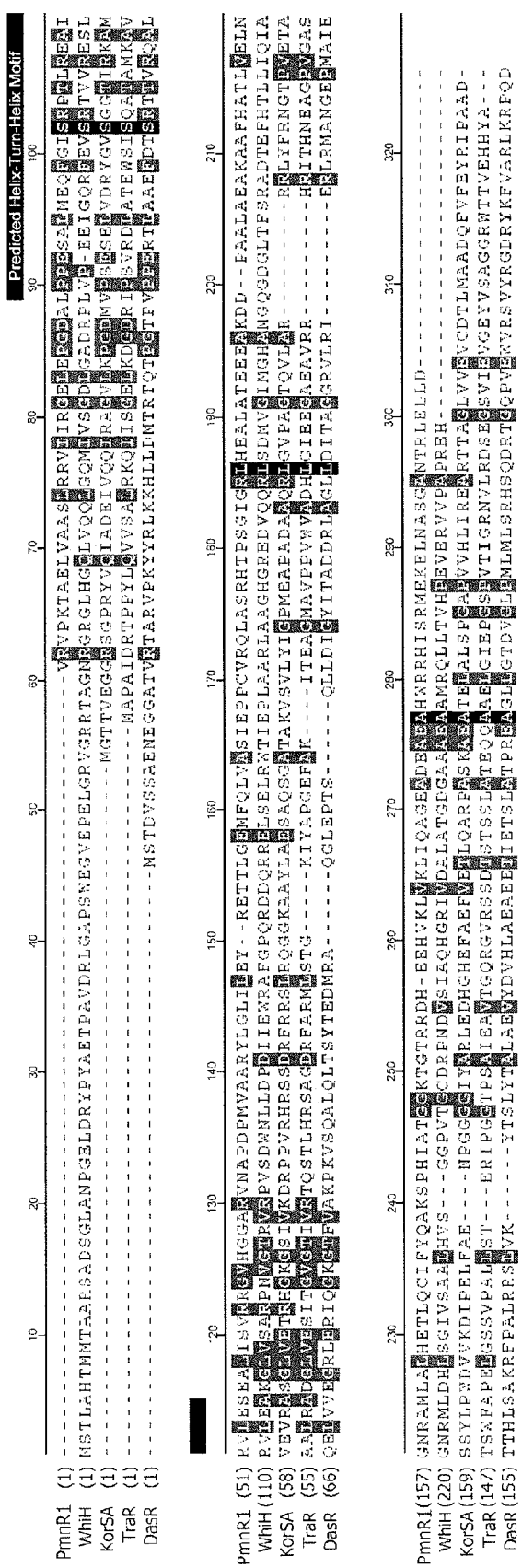
FIG. 10: Primary sequence alignment of ORF34 with other characterized GntR family transcriptional regulators from the genus *Streptomyces*, including WhiH and DasR from *S. coelicolor* A3(2), KorSA from *S. ambofaciens*, and TraR from *S. ghanaensis*. The sequence encoding a predicted helix-turn-helix DNA binding motif is noted with a black bar.
Figure 11:
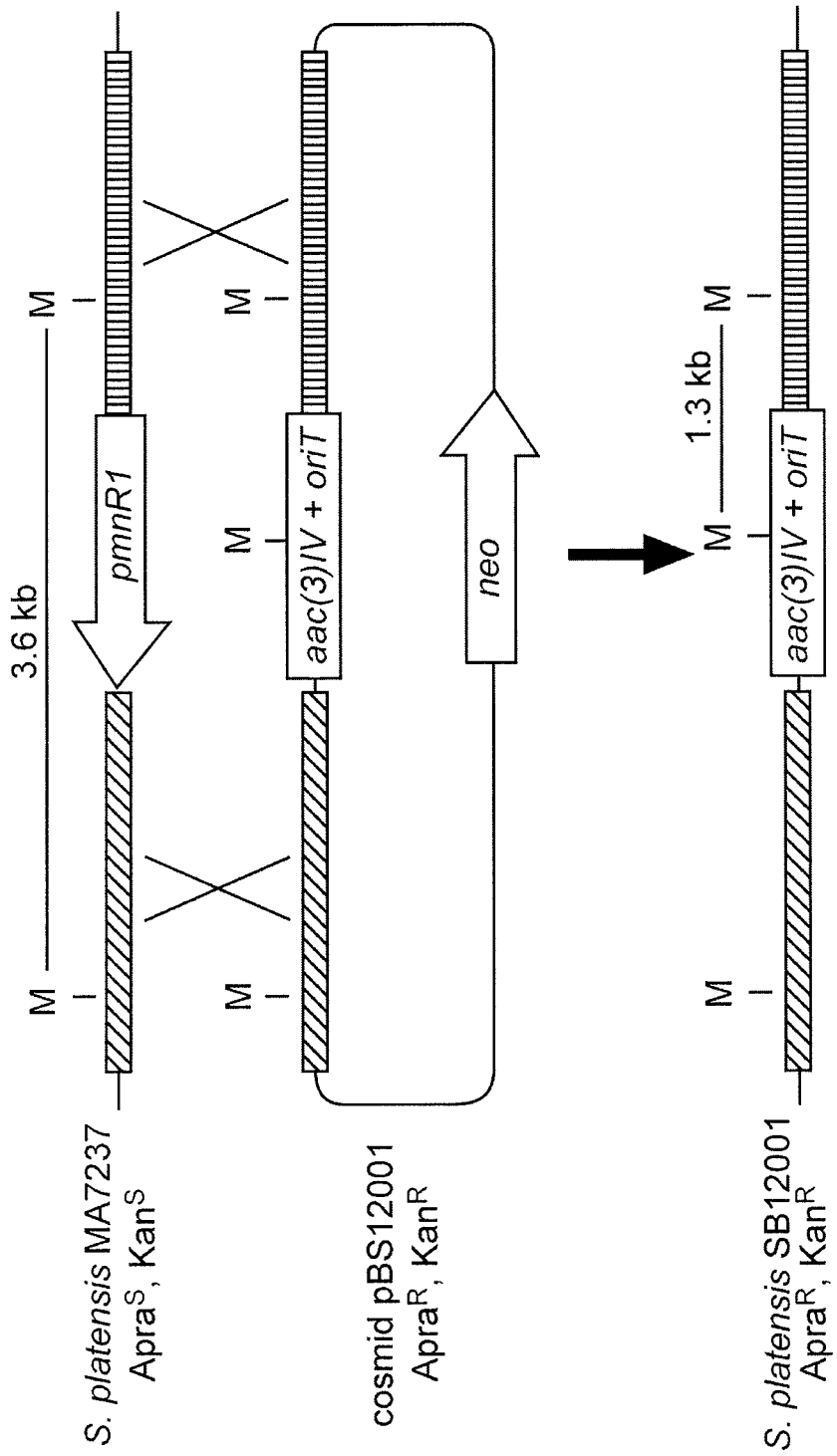
FIGS. 11A-B: Replacement of orf34 with the apramycin resistance gene, aac(3)IV, via homologous recombination.
Figure 11:
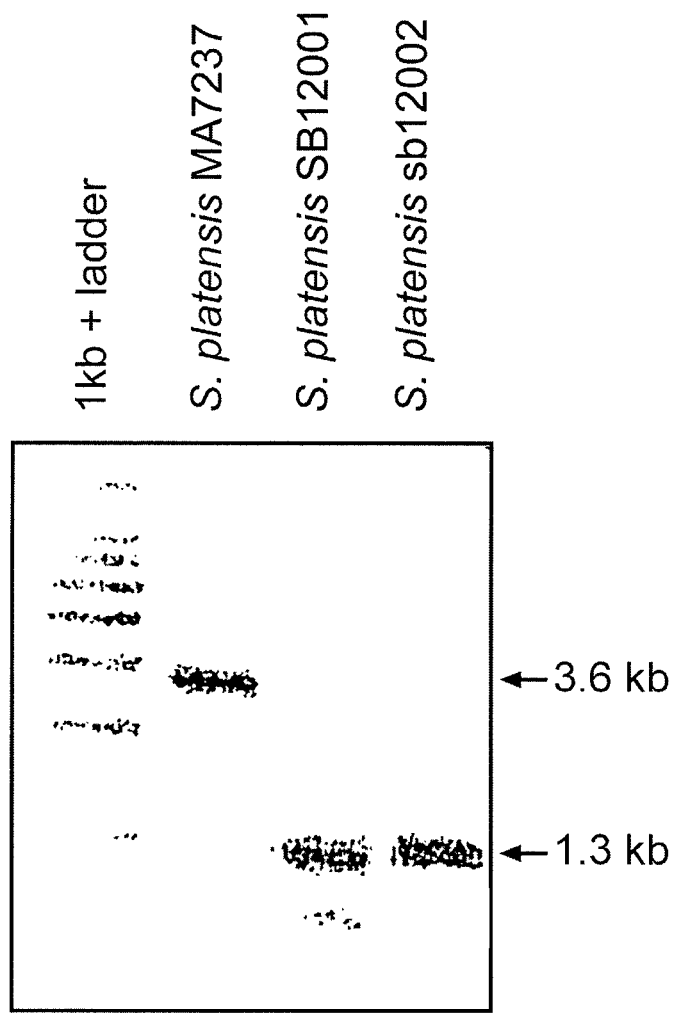

This genetic system was used to replace orf34 with the apramycin resistance cassette, aac(3)IV, using REDIRECT Technology (Gust et al., 2003). Two exconjugants, S. platensis SB12001 and SB12002, were isolated and the genotype confirmed by southern analysis (FIG. 11). HPLC analysis of the crude extract produced by culturing these mutant strains in standard production conditions showed significant improvement of both PMN and PCN titers (FIG. 7). Surprisingly, the two overproducing strains were found to have distinct chemical profiles, with S. platensis SB12002 routinely producing more PMN and S. platensis SB12001 routinely favoring PCN production. As the induced mutation in these strains has been shown to be identical by southern analysis, this titer difference can best be explained by a fortuitous genetic variation that existed between the two S. platensis MA7237 parent cells that received DNA during the original conjugation. In SLY medium, S. platensis SB12002 produces PMN with a yield of 323 mg/L and S. platensis SB12001 produces PCN with a yield of 255 mg/L (FIG. 8).

These experiments do not define the biosynthetic relationship between PMN and PCN, nor do they speak to the direct mechanism by which ORF34 regulates antibiotic production. However, these data vividly demonstrate the effectiveness of rational genetic manipulation of the natural biosynthetic pathway as a means to enhance the titer of important drug leads. This process stands in contrast to the lengthy, empirical strain improvement programs that have been traditionally implemented for the generation of overproducing strains (Demain, 1981).

In summary, the inventors have developed and implemented a strategy for genetic manipulation of PMN/PCN producer, S. platensis MA7237, to achieve significantly improved PMN/PCN production. The new strains S. platensis SB12002 and S. platensis SB12001 produce PMN and PCN with yields of 323 mg/L and 255 mg/L, respectively. These titers are ~100-fold greater than the original yields reported for the native producing strains, making the production and isolation of large amounts of these compounds vastly more efficient. These findings underscore once again the effectiveness of judicious application of metabolic pathway engineering principles for titer improvement. The overproducing strains reported here provide a solution to the concerns of PMN and PCN availability and should greatly facilitate the development of these promising lead compounds into clinical antibacterial agents.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

X. REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 4,551,433
U.S. Pat. No. 5,220,007
U.S. Pat. No. 5,221,605
U.S. Pat. No. 5,238,808
U.S. Pat. No. 5,284,760
U.S. Pat. No. 5,354,670
U.S. Pat. No. 5,366,878
U.S. Pat. No. 5,380,721
U.S. Pat. No. 5,389,514
U.S. Pat. No. 5,635,377
U.S. Pat. No. 5,789,166
U.S. Pat. No. 5,798,208
U.S. Pat. No. 5,830,650
Anderle et al., Chem. Biol., 14:955-967, 2007.
August et al., Chem. Biol., 5:69-79, 1998.
Baltz, Nat. Biotechnol., 24:1533-1540, 2006a.
Baltz, SIM News, 56:148-160, 2006b.
Barton, Nat. Rev. Drug Discov., 5:539. 2006.
Bibb, Curr. Opinion Microbiol., 8:208-215, 2005.
Bierman et al., Gene, 116:43-49, 1992.
Blackburn et al., J. Lipid. Res., 32(12):1911-1918, 1991.
Boothman et al., Cancer Res., 49(11):2871-2878, 1989.
Borek, Carcinog. Compr. Surv., 10:303-316, 1985.
Braisted and Wells, Proc. Natl. Acad. Sci. USA, 93(12):5688-5692, 1996.
Burks et al., Proc. Natl. Acad. Sci. USA, 94(2):412-417, 1997.
Burton and Barbas, Adv. Immunol., 57:191-280, 1994.
Cadwell and Joyce, PCR Methods Appl., 2(1):28-33, 1992.
Campbell et al., Annu. Rev. Microbiol., 55:305-332, 2001.
Cheng et al., J. Bacteriol., 184:7013-7024, 2002.
Cheng et al., Proc. Natl. Acad. Sci. USA, 100(6):3149-3154, 2003.
Christianson, Chem. Rev., 106:3412-3442, 2006.
Clardy and Walsh, Nature, 432:7-15, 2004.
Cooke et al., J. Am. Chem. Soc., 129:7728-7729, 2007.

Cooley et al., *Science*, 239(4844):1121-1128, 1988.
Cundliffe, *Ann. Rev. Microbiol.*, 43:207-233, 1989.
Cundliffe, In: *Self-protection mechanisms in antibiotic producers" in Secondary metabolites: their function and evolution*, Wiley, 199-214, Chichester, 1992.
Cundliffe, *J. Ind. Microbiol. Biotechnol.*, 33:500-506, 2006.
Cunningham and Wells, *Science*, 244(4908):1081-1085, 1989.
D'Costa et al., *Science*, 311:374-377, 2006.
Dairi, *J. Antibiot. (Tokyo)*, 58:227-243, 2005.
Davis and Croteau, *Topics Curr. Chem.*, 209:53-95, 2000.
Demain and Vaishnav, *SIM News*, 54:104-113, 2004.
Demain, *Science*, 214:987-995, 1981.
Du et al., *Chem. Biol.*, 7:623-642, 2000.
Durr et al., *Chem. Biol.*, 13:365-377, 2006.
El-Mansi et al., *Curr. Opinion Microbiol.*, 9:173-9, 2006.
Eustaquio et al., *Appl. Environ. Microbiol.*, 71:2452-2459, 2005.
Eustaquio et al., *Chem. Biol.*, 10:279-288, 2003.
Floss et al., *Curr. Opinion Chem. Biol.*, 3:592-597, 1999.
Floss, *J. Biotechnol.*, 124:242-257, 2006.
Galm and Shen, *Exp. Opinion Drug Dis.*, 1:409-437, 2006.
Galm et al., *Arch. Microbiol.*, 178:102-114, 2002.
Gould et al., *J. Am. Chem. Soc.*, 118:9228-9232, 1996.
Gramajo et al., *J. Bacteriol.*, 173:6475-6483, 1991.
Grim et al., *Gene*, 151:1-10, 1994.
Guilfoile & Hutchinson, *Proc. Natl. Acad. Sci. USA*, 88:8553-8557, 1991.
Gust et al., *Proc. Natl. Acad. Sci.*, 100:1541-1546, 2003.
Hall, *Genetics*, 120(4):887-897, 1988.
Hanson, *Nat. Prod. Rep.*, 23:875-885, 2005.
Hayashi et al., *FEBS Lett.*, 580:6175-6181, 2006.
Herath et al., *J. Am. Chem. Soc.*, 129:15422-15423, 2007.
Herath et al., *Org. Lett.*, 10:1699-1702, 2008.
Hillerich and Westpheling, *J. Bacteriol.*, 188:7477-7487, 2006.
Hilton et al., *J. Appl. Bacteriol.*, 81(6):575-584, 1996.
Hopwood and Sherman, *Ann. Rev. Geneet.*, 24:37-66, 1990.
Hopwood et al., *Meth. Enzymol.*, 153:116-166, 1987.
Hopwood, *Microbiology*, 145:2183-2202.
Hopwood, *Mol. Microbiol.*, 63:937-940, 2007.
Hornung et al., *Chem. BioChem.*, 8:757-766, 2007.
Hu and Floss, *J. Am. Chem. Soc.*, 126:3837-3844, 2004.
Huang et al., *Nucl. Acids Res.*, 24:4202-4209, 1996.
Jayasuriya et al., *Angew. Chem. Int. Ed Engl.*, 46:4684-4688, 2007.
Jayasuriya et al., *Angew. Chem. Int. Ed.*, 46:1-6, 2007.
Kao et al., *Science*, 265:509-512, 1994.
Kawasaki et al., *J. Antibiot.*, 56:957-966, 2003.
Kawasaki et al., *J. Bacteriol.*, 188:1236-1244, 2006.
Khosla and Keasling, *Nat. Rev. Drug Discov.*, 2:1019-1025, 2003.
Kieser et al., In: *Practical Streptomyces genetics*, The John Innes Foundation:Norwich, UK, 2000.
Kohen and Carter, *Nat. Rev. Drug Discov.*, 4:208-220, 2005.
Kuzuyama and Seto, *Nat. Prod. Rep.*, 20:171-183, 2003.
Kwon et al., *Science*, 297:1327-1330, 2002.
Lambert and Borek, *J. Natl. Cancer Inst.*, 80(18):1492-1497, 1988.
Li and Heide, *Curr. Med. Chem.*, 12:419-427, 2005.
Liu and Shen, *Antimicrob. Agents Chemother.*, 44:382-392, 2000.
Manallack et al., *Curr. Med. Chem.*, 15:705-710, 2008.
McCann et al., *Proc. Natl. Acad. Sci. USA*, 72(3):979-983, 1975.
Mohan et al., *Arch. Biochem. Biophys.*, 330:33-47, 1996.
Motamedi and Hutchinson, *Proc. Natl. Acad. Sci. USA*, 84:4445-4449, 1987.
Nicolaou et al., *Angew. Chem. Int. Ed Engl.*, 46:3942-3945, 2007a.
Nicolaou et al., *Angew. Chem. Int. Ed Engl.*, 46:4712-4714, 2007b.
Nicolaou et al. *J. Am. Chem. Soc.*, 129:14850-14851, 2007c.
Nicolaou et al., *Angew. Chem. Int. Ed Engl.*, 47:1780-1783, 2008.
Nicolaou et al., *Angew. Chem. Int. Ed.*, 47:944-946, 2008.
O'Hagan, In: *The Polyketide Metabolites*, Ellis Horwood Ltd., 1991.
Oppenheimer et al., *Cell*, 67(3):483-493, 1991.
Osoegawa et al., *Genomics*, 52:1-8, 1998.
Pearson, *Nature*, 441:260-261, 2006.
Petrickova et al., *J. Bacteriol.*, 188:5113-5123, 2006.
Pieper et al., *J. Am. Chem. Soc.*, 117:11373-11374, 1995.
Pleper et al., *Nature*, 378:263-266, 1995.
Pojer et al., *Microbiology*, 148:3901-3911, 2002.
Prisic et al., *Chem. BioChem.*, 8:869-874, 2007.
Prisic et al., *Plant Physiol.*, 136:4228-4236, 2004.
Remington's Pharmaceutical Sciences, 18th Ed. Mack Printing Company, 1289-1329, 1990.
Roy et al., *J. Am. Chem. Soc.*, 129, 2007.
Sambrook et al., Molecular Cloning: A Laboratory Manual, Cold Springs Lab., New York, 1989.
Shen and Hutchinson, *J. Biol. Chem.*, 269:30726-30733, 1994.
Singh et al. *J. Am. Chem. Soc.*, 128:11916-11920, 2006.
Steffensky et al., *Antimicrob. Agents Chemother.*, 44:1214-1222, 2000a.
Steffensky et al., *J. Biol. Chem.*, 275:21754-21760.140, 2000b.
Stutzman-Engwall and Hutchinson, *Proc. Natl. Acad. Sci. USA*, 86:3135-3139, 1989.
Suzuki et al., *J. Biol. Chem.*, 281:36944-36951, 2006.
Takano, *Curr. Opinion Microbiol.*, 9:1-8, 2006.
Tang et al., *Chem. Biol.*, 11:33-45, 2004.
Toyomasu et al., *Proc. Natl. Acad. Sci. USA*, 104:3084-3088, 2007.
Tudzynski, *Appl. Microbiol. Biotechnol.*, 66:597-611, 2005.
Van Lanen and Shen, *Drug Disc. Today: Technol.*, 3:285-292, 2006.
Vara et al., *J. Bacteriol.*, 171:5872-5881, 1989.
Walsh and Wright, *Chem. Rev.*, 105:391-393, 2005.
Walsh et al., *Curr. Op. Chem. Biol.*, 5:525-534, 2001.
Walsh, *Nat. Chem. Biol.*, 1:122-124, 2005.
Wang et al., *Antimicrob. Agents Chemother.*, 44:3040-3048, 2000.
Wang et al., *Nature*, 441:358-360, 2006.
Wang et al., *Proc. Natl. Acad. Sci. USA*, 104:7612-7616, 2007.
Warren et al., *Biochemisrty*, 35(27):8855-8862, 1996.
Weissman and Leadlay, *Nat. Rev. Microbiol.*, 3:925-936, 2005.
Wells et al., *J. Leukoc. Biol.*, 59(1):53-60, 1996.
Wiesmann et al., *Chem. Biol.*, 2:583-589, 1995.
Wilderman et al., *Plant Physiol.*, 135:2098-2105, 2004.
Witte et al., *Cancer Res.*, 49(18):5066-5072, 1989.
Woon et al., *Genomics*, 50:306-316, 1998.
Xu et al., *Chem. Biol.*, 11:655-622, 2004.
Xu et al., *Proc. Natl. Acad. Sci. USA*, 104:7397-7401, 2007a.
Xu et al., *Phytochemistry*, 68:312-326, 2007b.
Xu et al., *Phtyochemistry*, 68:312-326, 2007c.
Xu et al., *Plant J.*, 39:309-318, 2004.
Yelton et al., *J. Immunol.*, 155(4):1994-2004, 1995.
Yoshikuni et al., Nature, 440:1078-1082, 2006.
Young et al., *Antimicrobl. Agents Chemother.*, 50:519-526, 2006.
Zeng et al., *Biochemistry*, 35(40):13157-13164, 1996.
Zhao et al., *Microbiol. Res.*, 160:307-313, 2005.

What is claimed is:

1. A non-natural vector comprising all the genes encoded by SEQ ID NO:1.

2. The non-natural vector of claim 1, wherein said vector is a bacterial artificial chromosome.

3. A host cell comprising a polynucleotide, wherein said polynucleotide comprises 1000 or more bases of SEQ ID NO:1, said host cell not being a *Streptomyces platensis* cell.

4. The host cell of claim 3, wherein said polynucleotide comprises 5000, 10,000, 15,000, 20,000, 25,000, 30,000, 35,000, or all of SEQ ID NO:1.

5. The host cell of claim 3, wherein said host cell is an *Escherichia coli* cell.

6. A host cell comprising a polynucleotide in one or more non-natural vectors, wherein said polynucleotide comprises 1000 or more bases of SEQ ID NO:1.

7. The host cell of claim 6, wherein said vector is a bacterial artificial chromosome.

8. The host cell of claim 6, wherein said polynucleotide comprises 5000, 10,000, 15,000, 20,000, 25,000, 30,000, 35,000, or all of SEQ ID NO:1.

9. The host cell of claim 6, wherein said host cell is a *Streptomyces platensis* or *Escherichia coli* cell.

10. The host cell of claim 6, wherein said host cell comprises at least one heterologous tailoring gene.

11. The host cell of claim 10, wherein said heterologous tailoring gene encodes for an enzyme is selected from the group consisting of a methylation enzyme, an acetylation enzyme, a glycosylation enzyme, and a phosphorylation enzyme.

* * * * *

UNITED STATES PATENT AND TRADEMARK OFFICE
CERTIFICATE OF CORRECTION

PATENT NO. : 8,652,838 B2  
APPLICATION NO. : 12/179406  
DATED : February 18, 2014  
INVENTOR(S) : Ben Shen and Michael J. Smanski Page 1 of 1

It is certified that error appears in the above-identified patent and that said Letters Patent is hereby corrected as shown below:

In the Claims:

In claim 4, column 83, line 24, after the word all, insert --bases--.

In claim 8, column 84, line 18, after the word all, insert --bases--.

In claim 11, column 84, line 24, after the word enzyme, delete the word "is".

Signed and Sealed this  
Ninth Day of September, 2014

Michelle K. Lee  
*Deputy Director of the United States Patent and Trademark Office*